(12) United States Patent
Santerre et al.

(10) Patent No.: US 8,445,016 B2
(45) Date of Patent: May 21, 2013

(54) GRAFTED POLYMERS AND USES THEREOF

(75) Inventors: J. Paul Santerre, Whitby (CA); Roseita Esfand, Mississauga (CA); Meilin Yang, Mississauga (CA)

(73) Assignee: Interface Biologics, Inc., Toronto, Ontario (CA)

( * ) Notice: Subject to any disclaimer, the term of this patent is extended or adjusted under 35 U.S.C. 154(b) by 791 days.

(21) Appl. No.: 12/226,162

(22) PCT Filed: Apr. 13, 2007

(86) PCT No.: PCT/IB2007/002819
§ 371 (c)(1),
(2), (4) Date: Nov. 19, 2009

(87) PCT Pub. No.: WO2007/148230
PCT Pub. Date: Dec. 27, 2007

(65) Prior Publication Data
US 2010/0055068 A1 Mar. 4, 2010

Related U.S. Application Data

(60) Provisional application No. 60/792,169, filed on Apr. 14, 2006.

(51) Int. Cl.
*A61K 9/14* (2006.01)
(52) U.S. Cl.
USPC ........ 424/486; 424/405; 424/487; 514/772.1; 514/772.3
(58) Field of Classification Search
USPC ............. 424/405, 486, 487; 514/772.1, 772.3
See application file for complete search history.

(56) References Cited

U.S. PATENT DOCUMENTS 6,770,725 B2 * 8/2004 Santerre .......................... 528/29
2005/0129656 A1 6/2005 Goupil et al.

FOREIGN PATENT DOCUMENTS

| WO | WO 98/10805 | 3/1998 |
| WO | WO 02/098477 | 12/2002 |
| WO | WO 2005/110485 | 11/2005 |
| WO | WO 2007/004067 | 1/2007 |

OTHER PUBLICATIONS

Betti, M., et al.; Free Radical Biology & Medicine, 2006, vol. 41, p. 464-472.*
New Zealand Examination Report pertaining to Patent Application No. 572566, dated May 21, 2010.
Hester et al., "ATRP of Amphiphilic Graft Copolymers Based on PVDF and Their Use as Membrane Additives," *Macromolecules*, 35(20):7652-7661, 2002.
Park et al., "Synthesis and Characterization of SPUU-PEO-Heparin Graft Copolymers," *Journal of Polymer Science: Part A: Polymer Chemistry*, 29(12):1725-1737, 1991.
International Preliminary Report on Patentability corresponding to International Application No. PCT/IB2007/002819, issued Oct. 14, 2008.
International Search Report corresponding to International Application No. PCT/IB2007/002819, mailed Feb. 29, 2008.
Written Opinion of the International Searching Authority Corresponding to International Application No. PCT/IB2007/002819, mailed Feb. 29, 2008.
Extended European Search Report from European Patent Application No. 07845232.3, dated Jun. 22, 2010.
Office Action in corresponding Japanese Patent Application No. 2009-504859, mailed Mar. 27, 2012.

* cited by examiner

*Primary Examiner* — Robert Jones, Jr.
(74) *Attorney, Agent, or Firm* — Clark & Elbing LLP; Kristina Bieker-Brady

(57) ABSTRACT

The invention features grafted polymer systems for use in medical devices and/or for the delivery of active agents. The grafted polymers include at least one transport moiety, a linear backbone segment, and a pendant segment.

8 Claims, 14 Drawing Sheets

GPC analysis of (compound 33) and its precursors.

Release of ibuprofen from a (compound 39) (DMF) / Chronothane film in PBS, 37 °C.

Release of hydrocortisone from a (compound 40) / Carbothane film in PBS, 37 °C.

Release of dexamethasone from a (compound 41) / Chronothane film in PBS, 37 °C.

SEM of stent coated with (compound 41).

Release of paclitaxel from a (compound 42) / Carbothane film in PBS with Tween, 37 °C.

Release of cisplatin from (compound 43) in water at 37 °C.

Solution coating of (compound 44) on a non-electropolished stainless steel coupon imaged using a microscope.

Release of methotrexate from a (compound 45) / Carbothàne film in PBS, 37 °C.

Release of ascorbic acid (vitamin C) from a (compound 46) / Chronothane film in PBS, 37 °C.

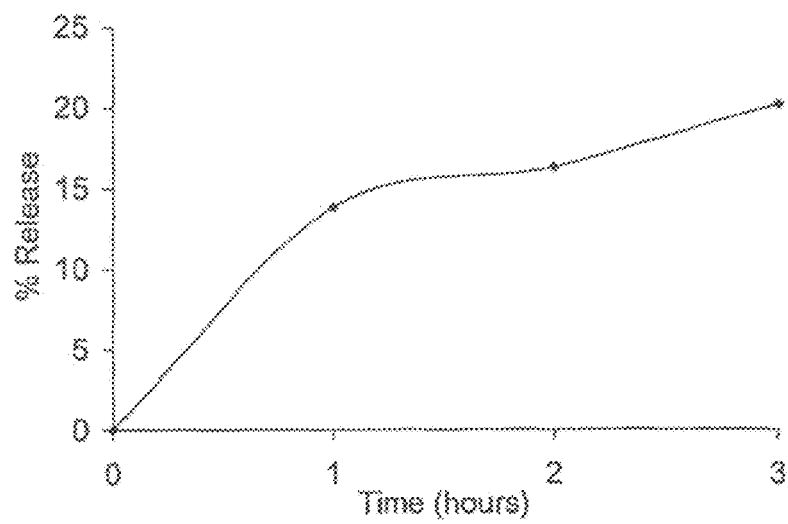
FIGURE 11:
Release of salicylic acid from a (compound 47) (DMF) / Carbothane film in PBS, 37°C.
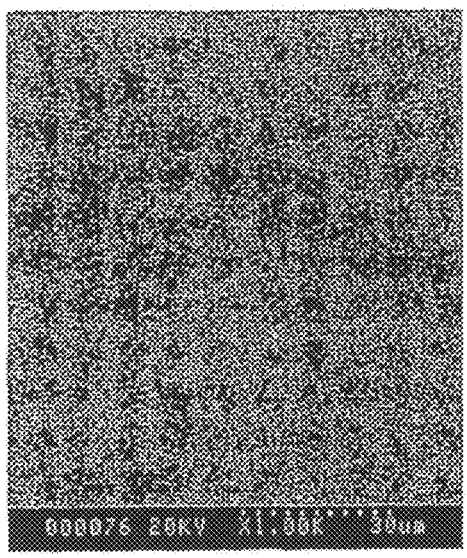
FIGURE 12: SEM of
(Compound 47) (MeOH) / Carbothane.
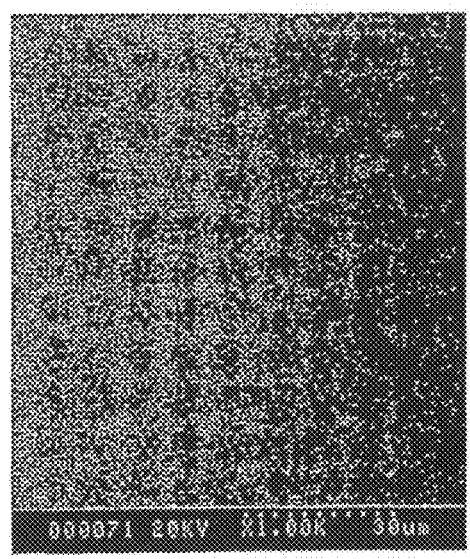
FIGURE 13: SEM of
(Compound 47) (DMF) / Carbothane.

Release of chlorhexidine from a (compound 48) / Carbothane film in water, 37 °C.

Release of oxybutynin from a (compound 49) / Chronothane film in artificial urine, 37 °C.

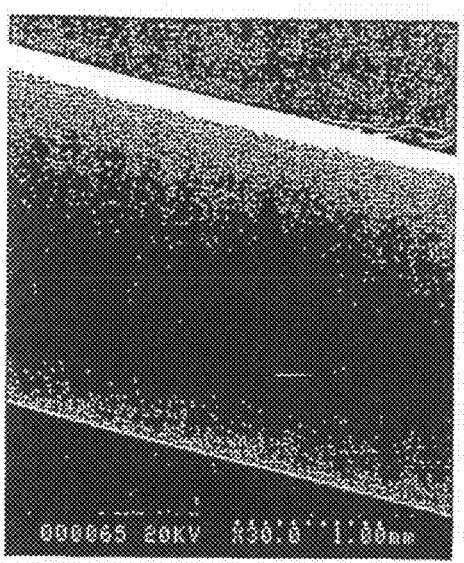
FIGURE 16: SEM of Carbothane catheter catheter (control).
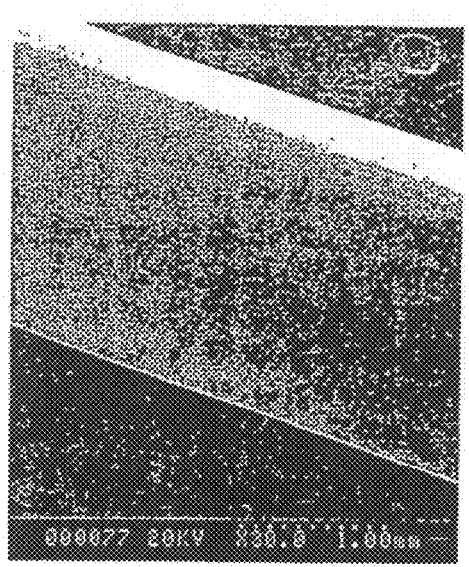
FIGURE 17: SEM of Carbothane dipcoated with (compound 49).
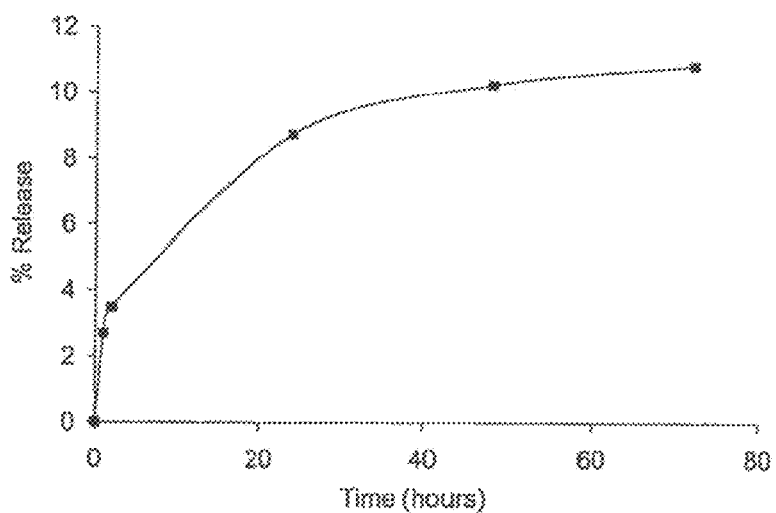
FIGURE 18:
Release of vitamin K1 from a (compound 50) (DMF) / Carbothane film in PBS with Tween, 37 °C.

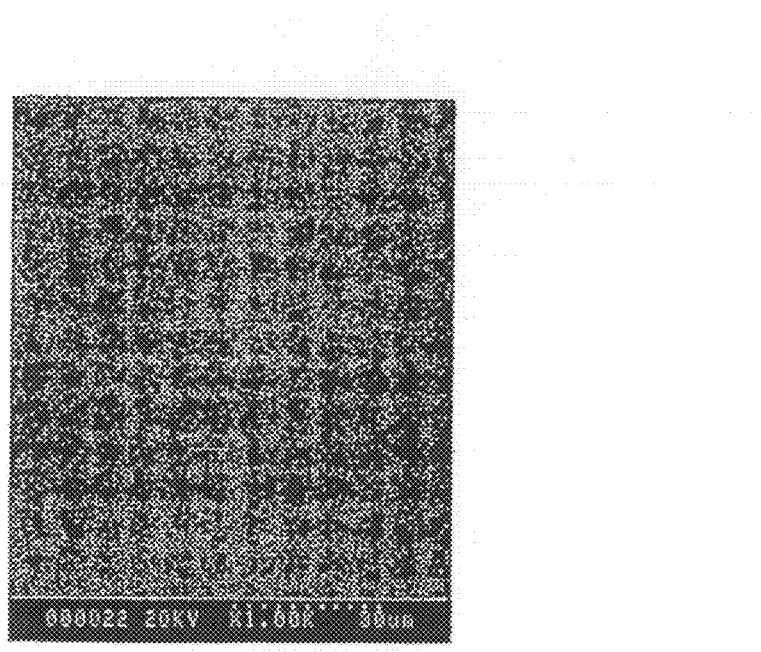
FIGURE 19: SEM of a (compound 52) / Carbothane film.
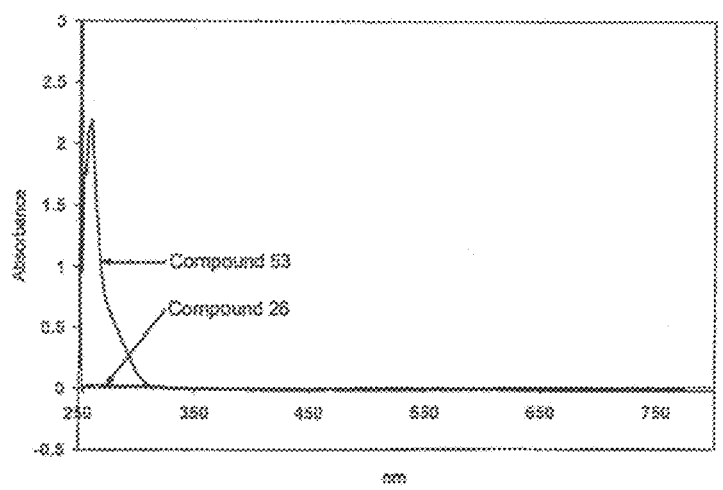
FIGURE 20
UV/VIS profile of (compound 26) and (compound 53). Both compounds were dissolved in DMSO.

Chemical structure of paclitaxel. Numbers on the diagram are referenced in the proton NMR analysis of (compound 53). The drug is conjugated to (compound 26) via the C2' hydroxyl, leading to a shift in the C2' signal from 4.68 ppm to 5.44 ppm.

Comparison of the GPC UV profiles of (compound 23) and (compound 54).

UV/VIS profile of (compound 23) and (compound 54). Both compounds were dissolved in DMSO.

Repeat segment of HEMA in (compound 55), indicating NMR assignments.

Schematic of dendron structures derived from (compound 2) G1 and G2 refer to dendron generations.

Friction coefficient analysis of Tecoflex films blended with (compounds 22, 59, and 27).

Compounded pellets of Carbothane with (compound 22) and (compound 27).

Extruded hollow tubing with pellets from Carbothane compounded with (compound 22) and (compound 27).

GRAFTED POLYMERS AND USES THEREOF

CROSS-REFERENCE TO RELATED APPLICATIONS

This application is the U.S. National Stage of International Application No. PCT/IB2007/002819, filed Apr. 13, 2007, and claims the benefit of U.S. Provisional Application No. 60/792,169, filed Apr. 14, 2006, each of which is incorporated herein by reference.

BACKGROUND OF THE INVENTION

The invention relates to grafted polymers.

Synthetic approaches used to enhance biocompatibility of polymers used in medical devices include bulk and surface modification of polymers. Bulk modification is mainly achieved by modifying the chemical composition throughout the polymer. In contrast, surface modification is generally achieved by surface derivation of a polymeric article. Surface modification offers one major advantage above bulk modification in that surface modification retains the material's mechanical characteristics, which are intimately related to the chemical composition of the polymer, and selectively alters the interfacial characteristics at the polymer surface.

Polymers are synthesized by polycondensation or by addition polymerization. Grafting reactions are most commonly used methods to incorporate a plurality of structures consisting of polycondensates and polyvinyls, or their combination, into one molecule. Energy initiated grafting, such as plasma grafting, UV grafting and radiation grafting, produce substances with complex structures. To date, the grafting by chemical initiated free radical polymerization can only be used for selected vinyl monomers, such as hydroxyethyl methacrylate, having a hydroxyl group which is able to covalently bond to the main chain in order to provide the initial graft site. The resulting structures of the products are polydispersed and difficult to reproduce precisely, in terms of the chain length (i.e. the introduction of a well defined number of moieties via monomer assembly).

Polymeric delivery platforms can be used to control the rate and period of drug delivery (i.e., time-release medications) and target specific areas of the body for treatment. Different polymer platforms can be employed to fulfill the goal of controlled delivery of an active agent. The three main mechanisms by which a pharmaceutical compound can be released from a polymeric delivery platform are diffusion, degradation and swelling. It is also possible to covalently attach the pharmaceutically active compound to the polymer active functional groups. This method has the advantage of the drug being targeted to the microenvironment where the therapeutic effect of the drug is required. For example if the system is designed for delivery to a tumor environment then a pH dependent release mechanism is applicable. The covalent bond between a polymer and drug can be designed to respond to hydrolysis under acidic conditions. Localized diseases are generally treated with pharmaceuticals delivered systemically. This mode of delivery is often hindered by safety, effectiveness and efficiency issues. For example systemic delivery of chemotherapeutic agents often results in side effects. The design of targeted and localized drug delivery platforms should provide better therapeutic efficacy. The system can be designed in the form of a small implant at the site of the diseased area to provide controlled release of pharmaceuticals for a prescribed period of time. In the area of cardiovascular diseases, stenting have become an acceptable therapy/implant for treating complex and unstable coronary artery lesions. The increased neointima hyperplasia and in stent restenosis remain problematic with bare metal stent procedures. The systemic administration of drugs, have failed to resolve the problem due to concentration below therapeutic effect at the target site. Accordingly endovascular stents have become the best platforms for local drug delivery in coronary arterial lesions. The use of polymers in this area has brought unique structure activity requirements in the chemical composition design. Vascular compatibility and drug release profiles remain as some of the most important and challenging parameters in the rational design of polymers in this area. A variety of stable and biodegradable polymers, with potential for drug delivery applications is currently available in the market. It is the specific properties required for a particular application that continuously drives the development of new polymers. The ideal parameters for local drug delivery are dictated by clinical considerations and there is no single polymer that can fulfill these requirements for an array of diseases.

There exists a need for copolymer systems which can be designed to provide the necessary multiple and repeated functional groups on polymers that endow the polymers with variability in both bulk and surface properties to match the needs described above. There is also a need to achieve the synthesis of such materials in a manner that tightly controls the extent of the multiplicity in function, given the unique properties and dose dependence of the functional groups, in terms of their influence on physical properties of the materials (i.e. achieving desired surface hardness, lubricity and hydrophilicity, without compromising brittleness and swelling character), or their effect on and bioreactive properties (i.e. achieving therapeutic action on cells and tissues, without compromising toxicity or desired enzymatic interactions) for a given application. The present invention addresses these technical difficulties and offers advantages over the prior art.

SUMMARY OF THE INVENTION

The invention provides grafted polymers for use in articles, such as medical devices. The grafted polymers of the invention optionally include one or more active agents. When used in medical applications, the grafted polymers of the invention can be designed to provide surface properties that offset inflammatory responses and reduce thrombosis, and control the migration and release of active agents. For any given application, the grafted polymer of the invention can be designed to provide physical surface properties that compensate for poor lubricity, surface hardness, and hydrophilicity, among others. The grafted polymers of the invention permit greater control over critical parameters that define medical implant or device comparability.

In a first aspect, the invention features a grafted polymer including (i) a transport moiety, (ii) a linear backbone segment including a polycondensate, and (iii) a pendant segment including a polyolefin or a dendron, wherein the pendent segment is covalently tethered to the linear segment and the transport moiety is covalently tethered to either the pendent segment or the linear segment.

In a second aspect, the invention features a grafted polymer including (i) a transport moiety, (ii) a linear backbone segment, and (iii) a pendant segment including at least three oligomeric arms, wherein the pendent segment is covalently tethered to the linear segment and the transport moiety is covalently tethered to either the pendent segment or the linear segment.

In a third aspect, the invention features a grafted polymer including (i) a transport moiety, (ii) a linear backbone segment, and (iii) a pendant segment including (a) a polycondensate, a polyolefin, or combinations thereof, and (b) two or more active agents, two or more complexing moieties, a repeating hydrophilic segment, or combinations thereof, wherein the pendent segment is covalently tethered to said linear segment and said transport moiety is covalently tethered to either the pendent segment or the linear segment.

In a fourth aspect, the invention features a grafted polymer including (i) a transport moiety, (ii) a linear backbone segment, and (iii) a pendant segment including a hydrophilic polymer, wherein the pendent segment is covalently tethered to the linear segment and the transport moiety is covalently tethered to either the pendent segment or the linear segment.

In any of the above aspects, the grafted polymer can include a pendent segment including a polyolefin selected from polyacrylic acid, polymethacrylic acid, poly(hydroxyethylmethacrylate), poly(hydroxyethylacrylate), poly(methylalkylsulfoxide methacrylate), poly(methylalkylsulfoxide acrylate), polyacrylamide, poly(methacrylamide), poly(dimethylacrylamide), poly(N-isopropyl-acrylamide), poly(vinyl alcohol), poly(vinyl pyrrolidone), poly(N-vinyl caprolactam), and copolymers thereof. In certain embodiments, the pendant segment has a molecular weight of at least 100 Da, 200 Da, 300 Da, 400 Da, 500 Da, 600 Da, 700 Da, 800 Da, 900 Da, 1000 Da, 1500 Da, or even 2000 Da.

In another embodiment of the above aspects, the grafted polymer has the properties of a base polymer.

Desirably, the grafted polymer of the invention includes one or more complexing moieties, and one or more active agents, wherein the complexing moiety is covalently tethered to the pendant segment, and wherein the complexing moiety is complexed with the active agent. In certain embodiments, the pendant complexing moiety provides two or more functional groups capable of forming non-covalent interactions with the active agent.

In another embodiment, the grafted polymer of the invention includes one or more active agents covalently tethered to the pendant segment.

The active agent can be selected from, without limitation, proteins, peptides, carbohydrates, antibiotics, antiproliferative agents, rapamycin macrolides, analgesics, anesthetics, antiangiogenic agents, antithrombotic agents, vasoactive agents, anticoagulants, immunomodulators, cytotoxic agents, antiviral agents, antibodies, neurotransmitters, psychoactive drugs, oligonucleotides, proteins, vitamins, lipids, and prodrugs thereof.

In certain embodiments, the transport moiety is selected from polydimethylsiloxanes, hydrocarbons, fluorocarbons, polyfluoroalkyls, fluorinated polyethers, polyalkylene oxides, and combinations thereof. Desirably, the transport moiety is a polyfluoroalkyl. Polyfluoroalkyls useful in the methods and compositions of the invention include, without limitation, radicals of the general formula $CF_3(CF_2)_rCH_2CH_2$, wherein r is 2-20, and $CF_3(CF_2)_s(CH_2CH_2O)_\chi$ wherein $\chi$ is 1-10 and s is 1-20.

In another embodiment of the above aspects, the grafted polymer has a linear backbone segment which is an oligomeric segment of not fewer than 20 repeating units.

For any grafted polymer of the invention, the linear backbone segment can include, without limitation, polyurethane, polyurea, polyamides, polyaklylene oxide, polycarbonate, polyester, polylactone, polysilicone, polyethersulfone, polyolefin, polyvinyl derivative, polypeptide, polysaccharide, polysiloxane, polydimethylsiloxane, polyethylene-butylene, polyisobutylene, polybutadiene, polypropylene oxide, polyethylene oxide, polytetramethyleneoxide, or polyethylenebutylene segments.

For any grafted polymer of the invention, the pendent segment can include, without limitation, from polyacrylic acid, polymethacrylic acid, poly(hydroxyethylmethacrylate), poly(hydroxyethylacrylate), poly(methylalkylsulfoxide methacrylate), poly(methylalkylsulfoxide acrylate), polyacrylamide, poly(methacrylamide), poly(dimethylacrylamide), poly(N-isopropyl-acrylamide), poly(vinyl alcohol), poly(vinyl pyrrolidone), poly(N-vinyl caprolactam), and copolymers thereof.

The invention also features a grafted polymer described by the formula:

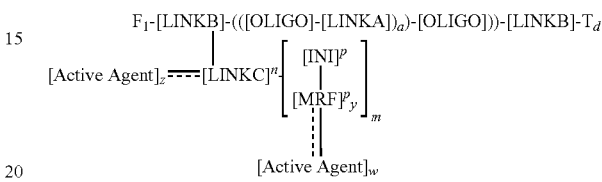

wherein [OLIGO] is an oligomeric polymeric segment; [LINKA] is a first coupling segment linking at least two [OLIGO] groups to form (([OLIGO]-[LINKA])$_a$-[OLIGO])) having a theoretical molecular weight of less than 15,000 Da;

T is a terminal group; $F_T$ is a polyfluoroorgano group; [MRF] is a polyolefin; [INI] is a functional group having the capacity to initiate ATRP, atom transfer radical addition (ATRA), or atom transfer radical cyclization (ATRC); [LINKB] is a second coupling segment linking (([OLIGO]-[LINKA])$_a$-[OLIGO])) to $F_T$, to T, and/or to [LINKC]; [LINKC] is a third coupling segment linking [LINKB] to [INI] or, in the absence of [INI], [LINKC] is a dendron of n generations; [Active Agent] is one or more active agents either complexed or covalently tethered to [LINKC] or to [MRF]; a and d are integers greater than 0, n is an integer from 1 to 150; p is an integer from 1 to 20; and m, p, y, and w are 0 or an integer from 1 to 20; with the provisos that m$\leq$n, w$\leq$y, when m, p, y, and w are 0, then n is an integer from 2 to 150, when z$\geq$1, then m=0, and when m$\geq$1, then z=0.

In certain embodiments (([OLIGO]-[LINKA])$_a$-[OLIGO])) includes a polycondensate selected from polyurethane, polyurea, polyamides, polyaklylene oxide, polycarbonate, polyester, polylactone, polysilicone, polyethersulfone, polypeptide, polysaccharide, polysiloxane, polydimethylsiloxane, polypropylene oxide, polyethylene oxide, polytetramethyleneoxide, and combinations thereof.

In other certain embodiments [MRF] is selected from polyacrylic acid, polymethacrylic acid, poly(hydroxyethylmethacrylate), poly(hydroxyethylacrylate), poly(methylalkylsulfoxide methacrylate), poly(methylalkylsulfoxide acrylate), polyacrylamide, poly(methacrylamide), poly(dimethylacrylamide), poly(N-isopropyl-acrylamide), poly(vinyl alcohol), poly(vinyl pyrrolidone), poly(N-vinyl caprolactam), and copolymers thereof.

In some embodiments $F_T$ is a polyfluoroalkyl of the general formula $CF_3(CF_2)_rCH_2CH_2$— wherein r is 2-20, and $CF_3(CF_2)_s(CH_2CH_2O)_\chi$ wherein $\chi$ is 1-10 and s is 1-20. Desirably, $F_T$ has a molecular weight of between 100-1,500 Da. In certain embodiments $F_T$ can include from about 0.01 to 50, 0.01 to 40, 0.01 to 30, 0.01 to 20, 0.01 to 10, 0.01 to 5, 0.1 to 50, 0.1 to 40, 0.1 to 30, 0.1 to 20, 0.1 to 10, 0.1 to 5, 1 to 50, 1 to 40, 1 to 30, 1 to 20, 1 to 10, 1 to 5, 5 to 50, 5 to 40, 5 to 30, 5 to 20, or even 5 to 10 weight % of the grafted polymer.

Desirably, the active agent is selected from proteins, peptides, carbohydrates, antibiotics, antiproliferative agents, rapamycin macrolides, analgesics, anesthetics, antiangiogenic agents, antithrombotic agents, vasoactive agents, anticoagulants, immunomodulators, cytotoxic agents, antiviral agents, antibodies, neurotransmitters, psychoactive drugs, oligonucleotides, proteins, vitamins, lipids, and prodrugs thereof.

In certain embodiments ((([OLIGO]-[LINKA])$_a$)-[OLIGO])) has an absolute molecular weight of greater than 10 kDa, 12 kDa, 14 kDa, 16 kDa, 20 kDa, 24 kDa, 28 kDa, 35 kDa, 50 kDa, 75 kDa, or even 100 kDa. In these instances, the grafted polymer may be designed to have the properties of a base polymer.

In other embodiments ((([OLIGO]-[LINKA])$_a$)-[OLIGO])) has an absolute molecular weight of less than 10 kDa. In these instances, the grafted polymer may be added to a base polymer for the purpose of modifying the properties of the base polymer.

In another aspect, the invention features an admixture including a grafted polymer of the invention admixed with a base polymer.

For any admixture of the invention, the admixture can include from 0.1 to 10 weight % grafted polymer of the invention. Desirably the admixture is between 0.01 and 15, 0.01 and 10, 0.1 and 5, 1 and 15, 1 and 10, or 1 and 5 weight % grafted polymer.

Exemplary base polymers for use in the admixtures of the invention include, without limitation, polyurethanes, polysulfones, polycarbonates, polysaccharide, polyethylene, polypropylene, polystyrene, poly(acrylonitrile-butadienestyrene), polybutadiene, polyisoprene, polyanhydride, polydioxane, polyacetal, polyoxalate, polyorthoester, polyiminocarbonate, polyesterurethane, polyphosphoester, poly(ϵ-docalactone), poly(ϵ-caprolactone), poly(B-propiolactone), polymalic acid, polyethyleneglycol, poly(β-hydroxybutyrate), styrenebutadiene-styrene block copolymers, styrene-iso-prenestyrene block copolymers, poly-R-methylpentene, polyisobutylene, polymethyl-methacrylate, polyvinylacetate-polyacrylonitrile, polyvinyl chloride, polyethylene terephthalate, cellulose and its esters and derivatives, polyamides, polyester-polyethers, styrene-isoprenes, styrene butadienes, thermoplastic polyolefins, styrene-saturated olefins, polyester-polyester, ethylene-vinyl acetate ethylene-ethyl acrylate, ionomers, thermoplastic polydienes, and combinations thereof.

The invention also features a shaped article formed from a grafted polymer of the invention.

The invention further features a shaped article formed from an admixture of a base polymer and a grafted polymer of the invention.

The article of the invention can be an implantable medical device, such as a cardiac-assist device, a catheter, a stent, a prosthetic implant, an artificial sphincter, or a drug delivery device.

In another aspect, the invention features a composition for delivery of an active agent including a grafted polymer of the invention, wherein the composition is formulated as a cream, gel, or lotion, e.g., for topical application in the absence of, during, or following a medical procedure.

The invention further features a composition for controlling the proliferation of pests (e.g., insects or weeds) including a grafted polymer of the invention including a pesticide (e.g., an insecticide) or herbicide.

The invention also features a composition for reducing microbial growth on a surface including a grafted polymer of the invention and an antimicrobial agent.

In another aspect, the invention features a method of reducing inflammation at a site in a mammal in need thereof. The method includes implanting an article of the invention at the site, wherein the grafted polymer of the invention includes an anti-inflammatory agent which is released from the surface of the article in an amount sufficient to reduce inflammation. Useful anti-inflammatory agents include, without limitation, naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid (salsalate), fenoprofen, flurbiprofen, ketoprofen, meclofenamate sodium, meloxicam, oxaprozin, sulindac, tolmetin, algestone, amcinonide, beclomethasone, betamethasone, budesonide, clobetasol, corticosterone, cortisone, dexamethasone, flucloronide, hydrocortisone, prednisolone, and triamcinolone, or combinations of these and other active agents.

In a related aspect, the invention features a method of reducing restenosis at a site in a mammal in need thereof. The method includes implanting an article of the invention at the site, wherein the grafted polymer of the invention includes an anti-proliferative agent which is released from the surface of the article in an amount sufficient to reduce restenosis. Useful anti-proliferative agents include, without limitation, rapamycin, CCI-779, Everolimus, ABT-578, mechlorethamine, cyclophosphamide, iosfamide, melphalan, chlorambucil, uracil mustard, estramustine, mitomycin C, AZQ, thiotepa, busulfan, hepsulfam, carmustine, lomustine, semustine, streptozocin, dacarbazine, cisplatin, carboplatin, procarbazine, methotrexate, trimetrexate, fluouracil, floxuridine, cytarabine, fludarabine, capecitabine, azacitidine, thioguanine, mercaptopurine, allopurine, cladribine, gemcitabine, pentostatin, vinblastine, vincristine, etoposide, teniposide, topotecan, irinotecan, camptothecin, 9-aminocamptothecin, paclitaxel, docetaxel, daunorubicin, doxorubicin, dactinomycin, idarubincin, plicamycin, mitomycin, amsacrine, bleomycin, aminoglutethimide, anastrozole, finasteride, ketoconazole, tamoxifen, flutamide, leuprolide, goserelin, Gleevec™, leflunomide, SU5416, SU6668, PTK787 (Novartis), Iressa™ (AstraZeneca), Tarceva™, trastuzumab, Erbitux™, PKI166, GW2016, EKB-509, EKB-569, MDX-H210, 2C4, MDX-447, ABX-EGF, CI-1033, Avastin™, IMC-1C11, ZD4190, ZD6474, CEP-701, CEP-751, MLN518, PKC412, 13-cis-retinoic acid, isotretinoin, retinyl palmitate, 4-(hydroxycarbophenyl)retinamide, misonidazole, nitracrine, mitoxantrone, hydroxyurea, L-asparaginase, interferon alfa, AP23573, Cerivastatin, Troglitazone, CRx-026, DHA-paclitaxel, Taxoprexin, TPI-287, Sphingosine-based lipids, and mitotane.

The invention also features a method of reducing pain at a site in a mammal in need thereof. The method includes implanting an article of the invention at the site, wherein the grafted polymer of the invention includes an analgesic or anesthetic agent which is released from the surface of the article in an amount sufficient to reduce pain. Useful analgesic agents include, without limitation, morphine, codeine, heroin, ethylmorphine, O-carboxymethylmorphine, O-acetylmorphine, hydrocodone, hydromorphone, oxymorphone, oxycodone, dihydrocodeine, thebaine, metopon, ethorphine, acetorphine, diprenorphine, buprenorphine, phenomorphan, levorphanol, ethoheptazine, ketobemidone, dihydroetorphine, and dihydroacetorphine. Useful anesthetic agents include, without limitation, cocaine, procaine, lidocaine, prilocalne, mepivicaine, bupivicaine, articaine, tetracaine, chloroprocaine, etidocaine, and ropavacaine.

The invention further features a method of relaxing muscle at a site in a mammal in need thereof. The method includes implanting an article of the invention at the site, wherein the grafted polymer of the invention includes an antispasmodic agent which is released from the surface of the article in an amount sufficient to relax muscle. Useful antispasmodic agents include, without limitation, atropine, belladonna, bentyl, cystospaz, detrol (tolterodine), dicyclomine, ditropan, donnatol, donnazyme, fasudil, flexeril, glycopyrrolate, homatropine, hyoscyamine, levsin, levsinex, librax, malcotran, novartin, oxyphencyclimine, oxybutynin, pamine, tolterodine, tiquizium, prozapine, and pinaverium.

In all of the above embodiments and aspects, the active agent may be provided as a prodrug, e.g., a amide or ester of the active agent.

The invention also features a method for synthesizing a grafted polymer of the invention by (a) mixing a first polymer with a vinyl monomer and (b) initiating atom transfer radical polymerization reaction of the first polymer and the vinyl monomer, wherein the first polymer includes a linear backbone segment covalently tethered to (i) a transport moiety and (ii) a functional group capable of initiating atom transfer radical polymerization with a the vinyl monomer and wherein step (b) is performed in the present of an active compound.

The invention further features a shaped article of the invention including a ligand having affinity for a target biological material.

The invention also features a method for the separation, isolation, or purification of a biological material by (a) contacting a sample containing the biological material with an article of the invention including a ligand having affinity for the biological material to cause the biological material to adhere to the article; and (b) affecting the separation, isolation, or purification of the biological material by separating the article from the sample following step (a).

In a related aspect, the invention features a method for detecting the presence or absence of a biological material in a sample by (a) providing an article of the invention including a ligand having affinity for the biological material; (b) contacting the sample with the article of step (a); and (c) following step (b), determining whether the biological material is adhered to said article.

In certain embodiments of the separation, purification, isolation, and detection methods, devices, and compositions of the invention the biological material includes a cell, a virus, a phage, a protein, a peptide, a carbohydrate, a glycopeptide, a glycoprotein, a glycosylaminoglycan, a cationic lipid, a glycolipid, or a polynucleotide. In other embodiments of the separation, purification, isolation, and detection methods, devices, and compositions of the invention the ligand includes a protein, a peptide, a carbohydrate, a glycopeptide, a glycoprotein, a glycosylaminoglycan, a cationic lipid, a glycolipid, or a polynucleotide.

As used herein, an "effective amount" refers to the amount of active agent in a grafted polymer of the invention necessary to achieve a desired result. The effective amount will vary depending upon a variety of parameters, including the condition being treated (e.g., pain, pest control, or microbial growth, among others), the site being treated, the active agent selected, the grafted polymer of the invention selected, and the delivery vehicle employed (e.g., implanted device, cream, or pellet, among others). An effective amount can be determined for any given set of conditions using standard methods. For example, the release of active agent from a surface can be monitored as a function of the parameters above. Based upon these results, a vehicle is prepared which releases the active agent at a rate that produces the desired effect.

As used herein, an "amount sufficient" refers to the use of a low molecular weight grafted polymer of the invention in an admixture with a base polymer. In such admixtures, the polymer of the invention is present in an amount sufficient to alter properties of the admixture, such as lubricity, surface hardness, hydrophilicity, water and/or solvent sensitivity, fouling and/or contaminant absorption/adsorption, chemical and radiation mediated oxidation, among others. These properties can be assessed by various standard measures. For example, lubricity can be evaluated with the ASTM D1894-01: Standard test method for static and kinetic coefficients of friction of plastic film and sheeting, and ASTM G 115-98: Standard guide for measuring and reporting friction coefficients. Hydrophilicity can be measured by water sessile drop contact angle measurements.

By "base polymer" is meant a polymer having a tensile strength of from about 350 to about 10,000 psi, elongation at break from about 300% to about 1500%, an unsupported thickness of from about 5 to about 100 microns, and a supported thickness of from about 1 to about 100 microns.

By "controlled inserted multiple and repeated function" is meant a polymer segment that has been incorporated within a targeted location of the polymer chain with a well defined chain length and repeated number of non-biological functional sites that multiply the functional value of a singular site on the central chain of a base polymer.

By "active agent" is meant a compound, be it naturally-occurring or artificially-derived, that is covalently or noncovalently bound to or complexed with a polymer of the invention and which may be released and delivered to a specific site. Active agents may include, for example, peptides, proteins, synthetic organic molecules, naturally occurring organic molecules, nucleic acid molecules, and components thereof. Desirably, the active agent is a compound useful for the therapeutic treatment of a plant or animal when delivered to a site of diseased tissue. Alternatively, the active agent can be selected to impart non-therapeutic functionality to a surface. Such agents include, for example, pesticides, bactericides, fungicides, fragrances, and dyes.

As used herein, "complexed" or "complexation" refers to an interaction, either non-covalent or via coordination to a metal center, between the polymer of the invention and an active agent. Examples of non-covalent bonding interactions which can be used in accordance with the present invention include, without limitation, hydrogen bonding, ionic interactions (e.g., dipole-dipole interactions, ion pairing, and salt formation), inclusion complexes, clathration, van der Waals interactions (e.g., pi-pi stacking), and combinations thereof. The interaction can also be via coordination to a metal center by both the complexing moiety and the active agent. In some instances, the active agent includes a metal center which is coordinated to the complexing moiety.

As used herein, "covalent" refers to an interaction via chemical bond formation by sharing a pair of electrons. By establishing specific functional groups within the chemical composition of the polymer (i.e. monomer) it is possible to covalently attach potent compounds to the polymer backbone.

As used herein, "complexing moiety' refers to that portion of the polymer of the invention which complexes the active agent either via a non-covalent interaction or coordination to a metal center, forming a polymer complex. The complexing moiety can be a charged moiety, e.g., a moiety which loses a proton at physiological pH thereby becoming negatively charged (e.g., carboxylate, or phosphodiester), a moiety which gains a proton at physiological pH thereby becoming positively charged (e.g., ammonium, guanidinium, or amidinium), a moiety that includes a net formal positive charge without protonation (e.g., quaternary ammonium), or a moiety that includes a net formal negative charge without loss of a proton (e.g., borate, BR4). Exemplary charged complexing moieties include, without limitation, carboxylate, phosphodiester, phosphoramidate, borate, phosphate, phosphonate, phosphonate ester, sulfonate, sulfate, thiolate, phenolate, ammonium, amidinium, guanidinium, quaternary ammonium, and imidazolium functionalities. The complexing moiety can be designed to physically encapsulate, in whole or in part, the active agent, such as a cyclodextrin. The complexing moiety be designed to ligate a complementary oligonucleotide and/or peptide sequence present in the active agent. The complexing moiety can be designed to coordinate a metal center including the active agent, either as a ligand alone or including the metal center.

As used herein, "covalently tethered" refers to moieties separated by one or more covalent bonds. For example, where a transport moiety is covalently tethered to a linear backbone segment, tethered includes the moieties separated by a single bond as well as both moieties separated by an oligomeric segment to which both moieties are covalently attached.

By "prodrug" is meant a precursor to an active agent which is converted in vivo, e.g., by enzymatic and/or hydrolytic mechanisms, into an active agent. Prodrugs include, without limitation, esterified active agents.

As used herein, "transport moiety" refers to a tail of a grafted polymer of the invention. Transport moieties are covalently attached to the linear backbone segment or pendant segment at a single point, for example, capping a terminus of the segment, or attached to a branching point in the middle of the segment. Transport moieties can be selected to be incompatible with the environment in which they are placed, such as in an article formed from an admixture of grafted polymer with a base polymer, resulting in orientation of the grafted polymer on the surface of the article to modify the surface properties. When used for this purpose the grafted polymer of the invention will typically have a low molecular weight (e.g., grafted polymers in which the linear backbone segment is less than 50 KDa, 40 KDa, 30 KDa, 20 KDa, or even 10 KDa) so the polymer of the invention in admixture with a base polymer can migrate to the surface of an article to modify the surface properties. Alternatively, the grafted polymer of the invention can have a high molecular weight (e.g., grafted polymers in which the linear backbone segment is greater than 10 KDa, 20 KDa, 30 KDa, 40 KDa, or even 50 KDa) so the polymer of the invention in admixture with a base polymer can reorient itself at the surface to modify the surface properties. Alternatively, for grafted polymers that include one or more active agents, the transport moieties can be positioned adjacent to the active agent to reduce degradation of the active agent in vivo and/or during the manufacture of articles of the invention. Transport moieties which can be used in the compositions and methods of the invention include, without limitation, polydimethylsiloxanes, hydrocarbons, fluorocarbons, fluorinated aryls, fluorinated polyethers, polyalkylene oxides, and combinations thereof.

The terms "hydrophilic" and "hydrophobic" are generally defined in terms of a partition coefficient P, which is the ratio of the equilibrium concentration of a compound in an organic phase to that in an aqueous phase. A hydrophilic compound has a log P value less than 1.0, typically less than about −0.5, where P is the partition coefficient of the compound between octanol and water or a calculation of the LogP using KowWin™ version 1.67, while hydrophobic compounds will generally have a log P greater than about 3.0, typically greater than about 5.0.

The term "hydrophilic polymer" as used herein refers to a synthetic polymer segment (i.e., a pendent segment) which renders the grafted polymer as a whole "hydrophilic," as defined above. Hydrophilic polymers useful in the methods and compositions of the invention can include, without limitation, polyalkylene oxides, particularly polyethylene glycol and copolymers of ethylene oxide (e.g., poly(ethylene oxide)-poly(propylene oxide) copolymers), polyacrylic acid, polymethacrylic acid, poly(hydroxyethylmethacrylate), poly (hydroxyethylacrylate), poly(methylalkylsulfoxide methacrylate), poly(methylalkylsulfoxide acrylate), polyacrylamide, poly(methacrylamide), poly(dimethylacrylamide), poly(N-isopropyl-acrylamide), poly(olefinic alcohol)s (e.g., poly(vinyl alcohol)), poly(N-vinyl lactams) (e.g., poly(vinyl pyrrolidone) and poly(N-vinyl caprolactam)), and copolymers thereof.

As used herein, "$t_{50}$" is the time at which 50% of the releasable active agent has been released from an article of the invention. Time $t_{10}$ is, correspondingly, the time at which 10% of the releasable active agent has been released. When the release curve is perfectly linear, $t_{10}=\frac{1}{5}$ of $t_{50}$. When there is an initial burst of released agent, $t_{10}$ is much less than $\frac{1}{5}$ of $t_{50}$. In the methods and articles of the invention $t_{10}$ can be greater than $\frac{1}{10}$ of $t_{50}$. Thus, there can be little or no initial burst of release of the active agent. The releasable active agent is the amount that is released from an article in a period of time 10 times greater than the period of time it takes for 10% of the incorporated agent to be released in phosphate buffered saline at pH 7.4.

By "biological material" is meant a substance that is naturally occurring, derived from a substance that is naturally occurring, or an analog of a substance that is naturally occurring. Biological entities include cells, viruses, phages, and the like. Biological entities also include biological molecules, as defined below.

By "biological molecule" is meant a substance that contains naturally occurring units, subunits, or analogues thereof. Biological molecules include, without limitation, proteins, peptides, carbohydrates, glycopeptides, glycoproteins, glycosylaminoglycans, cationic lipids, glycolipids, or polynucleotides. In addition, biological molecules may be synthetic molecules containing unnatural amino acids, unnatural nucleotides, and the like. Biological molecules may also be those entities derived from recombinant technology.

As used herein, the term "ligand" or "affinity ligand" refers to molecules having affinity for a target biological material either entrapped within or covalently attached to the polymers of the invention. Affinity ligands and methods of binding them to support materials are well known in the purification art, e.g., the reference texts *Affinity Separations. A Practical Approach* (Practical Approach Series), Matejtschuk (Editor), Irl Pr: 1997 and *Affinity Chromatography*, Herbert Schott, Marcel Dekker, New York: 1997. Exemplary affinity ligands include, without limitation, antibodies or antibody fragments, antigens, biotin, steptavidin, enzyme substrates or substrate analogs, protein A or protein A analogs, and complementary polynucleotides. These affinity ligands or other biological materials can be attached to the polymers of the invention using any of the techniques described herein for the incorporation of active agents. Detectable markers (i.e., labeling reagents) can be used to detect the presence or absence of a biological material on an article of the invention. Detectable markers include, without limitation, colored particles, such as colloidal gold particles; colloidal sulphur particles; colloidal selenium particles; colloidal barium sulfate particles; colloidal iron sulfate particles; metal iodate particles; silver halide particles; silica particles; colloidal metal (hydrous) oxide particles; colloidal metal sulfide particles; carbon black particles, colloidal lead selenide particles; colloidal cadmium selenide particles; colloidal metal phosphate particles; and colloidal metal ferrite particles. Any other visualization techniques known in the art may also be employed.

The following acronyms denote the listed compounds used in the preparation of the polymers, polymer complexes, and polymer conjugates described herein.
LDI lysine diisocyanate
HDI 1,6 hexamethylene diisocyanate
DABS 2,5 diaminobenzenesulfonic acid
PCN polycarbonate diol
PPO polypropylene oxide diol
MDI methylene diphenyl diisocyanate
PTMO polyethylene tetramethylene oxide
PCN polycarbonate diol
PDMS (polydimethylsiloxane-bis(3-aminopropyl) terminated)
PHE (amine terminated oligo-phenylalanine)
PEB (polyethylene-butylene co-polymer diol)
THDI trimethyl-1,6 diisocyanatohexane
DPS dihydroxy diphenylsulfone
PD 1,5 pentanediol
HDI/PCN/BD segmented polyurethane
DMAc dimethylacetamide
DME dimethylformamide
Fluoroalkyl Fluorinated alkyls with function terminal groups such as (OH, $NH_2$, COOH, NCO)
AA acrylic acid
AEE 2-(2-aminoethoxyl)ethanol
AEAPS -N-(2-aminoethyl)-3-aminopropane sulfonate
BA-L poly(difluoromethylene),α-fluoro-ω-(2-hydroxyethyl)
BIBB α-bromoisobutyryl bromide
tBMA ter-butyl methacrylate
tBA ter-butyl acrylate
BPY 2,2'-dipyridyl
DABPDS 4,4'-diamino 2,2'-biphenyl disulfonic acid
DBA dibutylamine
DBTDL dibutyltin dilaurate
DHVs dihydroxy vinyl derivatives
DMAc N,N-dimethylacetamide
DMAP 4-(dimethyamino)pyridine
DPA 2-(diisopropylamino)ethyl methacrylate
EDC 1-ethyl-3-(3-dimethylamino-propyl)carbodiimide.HCl
GK*GRGD glycine-lysine (dansyl labeled)-glycine-arginine-glycine aspartic acid peptide sequences
HEMA hydroxyethyl methacrylate
MAA methacrylic acid
MMA methyl methacrylate
MPC 2-methacryloyloxyethyl phosphorylcholine
OXC oxalyl chloride
PAA poly(acrylic acid)
PAAm N-isopropylacrylamide
PBd polybutyldiene diol
PDPAMA poly(diisopropylaminoethyl methacrylate)
PHEMA poly(2-hydroxyethyl mathacrylate)
PMAA poly(methacrylic acid)
PMDETA N,N,N'N',N'''-pentamethyldiethylenetriamine
PMPC poly(methacryloyloxyethyl phosphorylcholine)
PMSA polydimethylsiloxane-bis(3-aminopropyl) terminated
PNaA poly(sodium acrylate)
PNaMA poly(sodium methacrylate)
PPAAm poly(N-isopropylacrylamide)
PTMO poly(tetramethylene oxide)
PVP poly(vinyl pyrrolidone)
TCAA trichloroacetamide
TCE trichloroerhanol
TEA triethylamine
THDI 2,4,4-trimethyl-1,6-diisocyanatohexane
THF tetrahydrofuran
Tris tris(hydroxylmethyl)-aminomethane
VP 1-vinyl-2-pyrrolidone Other features and advantages of the invention will be apparent from the following detailed description, the drawings, and the claims.

BRIEF DESCRIPTION OF THE DRAWINGS

FIG. 11 is a plot of the release of salicylic acid from a (compound 47) (DMF)/Carbothane film showing 20-25% release within 3 hours.

FIG. 12 is an SEM image of a (compound 47) (MeOH)/Carbothane film showing a uniform surface morphology.

FIG. 13 is an SEM image of a (compound 47) (DMF)/Carbothane film showing no surface separation.

FIG. 16 is an SEM image of a of Carbothane catheter showing a uniform surface.

FIG. 17 is an SEM image of a Carbothane catheter dip-coated with (compound 49) showing no phase separation with uniform coating.

FIG. 18 is a plot of the release of vitamin K1 from a (compound 50) (DMF)/Carbothane film showing 10-12% release within 80 hours.

FIG. 19 is an SEM image of a (compound 52)/Carbothane film showing a uniform topology.

FIG. 20 is a UV/VIS profile of (compound 26) and (compound 53) showing acidic polymer with no UV/VIS characteristics and the paclitaxel conjugated polymer with UV/VIS characteristics.

DETAILED DESCRIPTION

Figure 1:
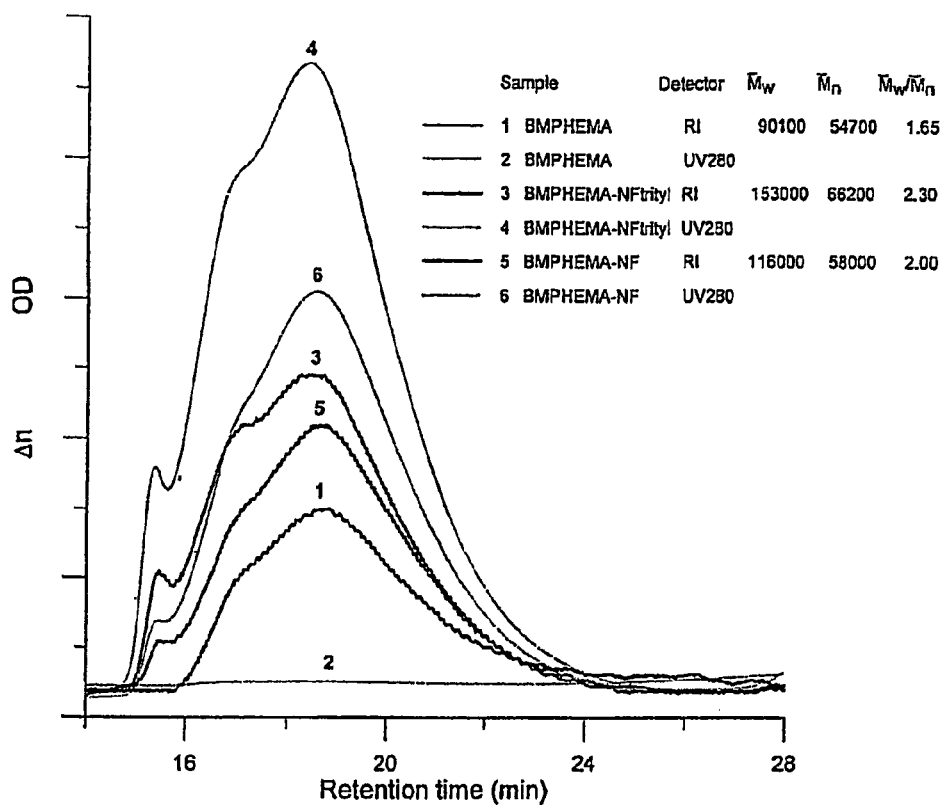
FIG. 1 is a GPC chromatogram of (compound 33) and its precursors showing that norfloxacin was successfully conjugated to (compound 23).

The methods and compositions of the invention allow for surface modification in a controlled manner, while maintaining the desired bulk properties of a base polymer. The surface modification results from interfacial energy minimization, using the methods and compositions of the invention, can be used to formulate specialized materials for specific applications. For example, surface modifications can be designed to alter the surface chemical composition, lubricity, hydrophobicity, biocompatibility, and/or adhesion characteristics. Furthermore, bulk surface rearrangements (relaxation, segregation, and reconstruction), including "chemical" changes, due to diffusion and/or transformation of surface atoms or molecules, can be controlled using surface modification processes described herein. This application claims benefit of U.S. Provisional Application No. 60/792,169, filed Apr. 14, 2007, and incorporated herein by reference.

The invention provides grafted polymers with many uses, including application in medical devices and/or delivery of active agents. The grafted polymers include at least one transport moiety, a linear backbone segment, and a pendant segment. The grafted polymers of the invention can be designed to deliver a wide variety of active agents. Where the active agent is complexed to the grafted polymer of the invention, no structural alteration of the agent being delivered is required. Furthermore, the release of complexed agents at a surface does not necessarily depend upon in vivo biodegradation processes. Accordingly, the complexes of the invention can be used to deliver active agents in non-biological environments.

Grafted Polymers

Grafted polymers of the invention include at least one transport moiety (e.g., a fluorinated tail), a linear backbone segment, and a pendant segment. The transport moiety and pendant segment are both tethered to the linear backbone segment. Optionally, the grafted polymer includes a complexing moiety capable of forming a complex with an active agent via non-covalent interactions or by coordination to a metal center. Alternatively, the active agent is covalently tethered to the grafted polymer.

Grafted Polymer Systems

The grafted polymers have strategic value for endowing base polymers with the ability to yield both the desired bulk and surface properties that uniquely address challenges such as the failure of surface modifiers with mono-functional chemistry to produce dense lubricious layers on polymer surfaces, because of their lack in ability to co-locate a multiplicity of hydrating salt function and non-ionic hydrogel character in combination with repetitive units of a finite content such that materials are not weakened physically. There is also a need to achieve the synthesis of such materials in a manner that tightly controls the extent of the multiplicity in function given the unique properties and dose dependence of the functional groups, in terms of their influence on physical properties of the materials (i.e. achieving desired surface hardness, lubricity and hydrophilicity, without compromising desired low brittleness and low swelling character). An example of a failure of these systems was associated with their inability to produce a dense lubricious layer on polymer surfaces, because of their lack in ability to co-locate a multiplicity of salt function and non-ionic hydrogel character in combination with repetitive function at the surface of the material to which the terminal fluorotails were migrating to.

Grafted Polymer Conjugates

The grafted polymers of the invention allow for controlled topography and stratification of the active agent within the base polymer (e.g., either the grafted polymer of the invention itself, or an admixture of the grafted polymer of the invention and base polymer) and, ultimately, controlled delivery at the targeted location. Furthermore, this design provides interfacial compartments or immobilization of the active compound.

The amount of active agent loaded onto the grafted polymer of the invention will depend upon the design of the grafted polymer in combination with the desired release profile. The concentration effect is in correlation to polyvalency and multiplicity of the sites available for covalent and/or non-covalent interaction with potent compounds. The composition of the grafted polymer may be designed for the particular agent being delivered (i.e., as with the selection of an appropriate complexing moiety) and to provide the mechanical properties necessary for a particular application.

The process by which the grafted polymer conjugates are formed may be a two or multi-step procedure that produces a homogenous matrix. In general, grafted polymers of the invention and their conjugates (covalent and non-covalent) can be prepared as described in the Examples.

Physical Properties

The physical properties of the grafted polymers can be designed in a manner to include the desired biomaterial properties required for specific application. Structure activity relationship parameters are set in prior to rational design of the grafted polymer for a specific application.

Atom Transfer Radical Polymerization (ATRP) and Dendritic Macromolecules

Dendritic polymers are a new class of polymer with well defined chemical structures having regular and highly branched three dimensional architectures. Dendrimers are synthesized by a series of iterative reaction steps, in which each reaction initiates the construction of a new generation. Dendrons are complete or partially symmetrical dendrimers and can be incorporated into linear polymers or used to form dendrimeric structures. Dendrimers and dendrons have three topological regions (core, branch and surface functionalities) that control the architectural properties of the final structure. They can be built in two ways; the divergent and the convergent methods. The divergent method involves initiation from a core and has step by step monomer additions. Each monomer can act as a branching point. In the convergent strategy the dendrimer branches are made first and finally connected to a central core. The advantage of the convergent strategy is that branches with different properties can be constructed prior to the attachment to a core molecule. Based on chemical composition and functional groups each repeat unit in a polymer backbone can initiate the synthesis and growth of dendron like structures. The oligomeric compounds used as the back bone in the ATRP synthesis are, in particular, interesting in the design and synthesis of dendritic polymers. The fluorine component introduces new complex interplay between dendron/fluorine, fluorine/fluorine and dendron/dendron interactions. The molecular dimension and structural properties of the polymer are governed by dendron structure, size, and attachment density. Dendron like structures can introduce localized microenvironments or internal cavities, analogous to the receptor site for a drug component, enzyme active site or viral receptor site. The concept of polyvalency and physical entrapment of guests are amongst some of the unique properties of the dendrimeric architecture.

The process by which the dendrons are introduced into the ATRP precursor can be achieved by two different pathways. The dendron synthesis can be initiated from carboxylic groups by one step reaction with a tris molecule. The total number of functional groups is increased by a factor of 3 in this step (two carboxylic groups converted to six hydroxyl groups). The next reaction involves the conversion of hydroxyl groups to carboxylic groups (six hydroxyl groups are converted to six carboxylic groups). Each carboxylic group can then react with tris molecules to increase the active terminal groups by a further factor of three (six carboxylic groups are converted to eighteen hydroxyl groups). Alternatively the tris molecule can be protected and the dendron like structure can be built to the desired size. De-protection of the tris primary amine group is necessary prior to conjugation of the dendron like structure to the polymer backbone.

One of the most important properties of dendritic structures is the ease to control their size, composition and chemical reactivity. The construction of new nanomaterials for coatings, non-linear optics and electronics, pharmaceuticals and the biomedical field can be pursued by self organization and/or self assembly of dendritic structures into nanoscale platforms with complex multifunctional units that define multifunctional nanodevices.

The dendritic polymers of the invention offer versatility in chemical design and polyvalency in their dendritic architectures that provides advantages for the use of these polymers for drug delivery. For example, the dendritic polymers of the invention can provide for higher loading of an active agent relative to linear polymer system and provide platforms that can deliver multiple drugs simultaneously.

Active Agents

Active agents that can be complexed or covalently tethered to the grafted polymers of the invention include therapeutic, diagnostic, and prophylactic agents. They can be naturally occurring compounds, synthetic organic compounds, or inorganic compounds. Agents that can be used in the grafted polymer complexes and grafted polymer conjugates of the invention include, but are not limited to, proteins, peptides, carbohydrates, antibiotics, antiproliferative agents, rapamycin macrolides, analgesics, anesthetics, antiangiogenic agents, vasoactive agents, anticoagulants, immunomodulators, cytotoxic agents, antiviral agents, antithrombotic drugs, such as terbrogel and ramatrob, anantibodies, neurotransmitters, psychoactive drugs, oligonucleotides, proteins, lipids, and combinations thereof.

Exemplary therapeutic agents include growth hormone, for example human growth hormone, calcitonin, granulocyte macrophage colony stimulating factor (GMCSF), ciliary neurotrophic factor, and parathyroid hormone. Other specific therapeutic agents include parathyroid hormone-related peptide, somatostatin, testosterone, progesterone, estradiol, nicotine, fentanyl, norethisterone, clonidine, scopolomine, salicylate, salmeterol, formeterol, albeterol, valium, heparin, dermatan, ferrochrome A, erythropoetins, diethylstilbestrol, lupron, estrogen estradiol, androgen halotestin, 6-thioguanine, 6-mercaptopurine, zolodex, taxol, lisinopril/zestril, streptokinase, aminobutylric acid, hemostatic aminocaproic acid; parlodel, tacrine, potaba, adipex, memboral, phenobarbital, insulin, gamma globulin, azathioprine, papein, acetaminophen, ibuprofen, acetylsalicylic acid, epinephrine, flucloronide, oxycodone percoset, dalgan, phreniline butabital, procaine, novocain, morphine, oxycodone, aloxiprin, brofenac, ketoprofen, ketorolac, hemin, vitamin B-12, folic acid, magnesium salts, vitamine D, vitamin C, vitamin E, vitamin A, Vitamin U, vitamin L, vitamin K, pantothenic acid, aminophenylbutyric acid, penicillin, acyclovir, oflaxacin, amoxicillin, tobramycin, retrovior, epivir, nevirapine, gentamycin, duracef, ablecet, butoxycaine, benoxinate, tropenzile, diponium salts, butaverine, apoatropine, feclemine, leiopyrrole, octamylamine, oxybutynin, albuterol, metaproterenol, beclomethasone dipropionate, triamcinolone acetamide, budesonide acetonide, ipratropium bromide, flunisolide, cromolyn sodium, ergotamine tartrate, and protein or peptide drugs such as TNF antagonists or interleukin antagonists. For example, the active agent can be an antiinflammatory agent, such as an NSAID, corticosteriod, or COX-2 inhibitor, e.g., rofecoxib, celecoxib, valdecoxib, or lumiracoxib.

Exemplary diagnostic agents include imaging agents, such as those that are used in positron emission tomography (PET), computer assisted tomography (CAT), single photon emission computerized tomography, X-ray, fluoroscopy, and magnetic resonance imaging (MRI). Suitable materials for use as contrast agents in MRI include gadolinium chelates, as well as iron, magnesium, manganese, copper, and chromium chelates. Examples of materials useful for CAT and X-rays include iodine based materials.

A preferred active agent is a substantially purified peptide or protein. Proteins are generally defined as consisting of 100 amino acid residues or more; peptides are less than 100 amino acid residues. Unless otherwise stated, the term protein, as used herein, refers to both proteins and peptides. The proteins may be produced, for example, by isolation from natural sources, recombinantly, or through peptide synthesis. Examples include growth hormones, such as human growth hormone and bovine growth hormone; enzymes, such as DNase, proteases, urate oxidase, alronidase, alpha galactosidase, and alpha glucosidase; antibodies, such as trastuzumab.

Rapamycin Macrolides

Rapamycin (Sirolimus) is an immunosuppressive lactam macrolide that is produced by *Streptomyces hygroscopicus*. See, for example, McAlpine, J. B., et al., *J. Antibiotics* 44: 688 (1991); Schreiber, S. L., et al., *J. Am. Chem. Soc.* 113: 7433 (1991); and U.S. Pat. No. 3,929,992, incorporated herein by reference. Exemplary rapamycin macrolides which can be used in the methods and compositions of the invention include, without limitation, rapamycin, CCI-779, Everolimus (also known as RAD001), and ABT-578. CCI-779 is an ester of rapamycin (42-ester with 3-hydroxy-2-hydroxymethyl-2-methylpropionic acid), disclosed in U.S. Pat. No. 5,362,718. Everolimus is an alkylated rapamycin (40-O-(2-hydroxyethyl)-rapamycin, disclosed in U.S. Pat. No. 5,665,772.

Antiproliferative Agents

Exemplary antiproliferative agents which can be used in the methods and compositions of the invention include, without limitation, mechlorethamine, cyclophosphamide, iosfamide, melphalan, chlorambucil, uracil mustard, estramustine, mitomycin C, AZQ, thiotepa, busulfan, hepsulfam, carmustine, lomustine, semustine, streptozocin, dacarbazine, cisplatin, carboplatin, procarbazine, methotrexate, trimetrexate, fluouracil, floxuridine, cytarabine, fludarabine, capecitabine, azacitidine, thioguanine, mercaptopurine, allopurine, cladribine, gemcitabine, pentostatin, vinblastine, vincristine, etoposide, teniposide, topotecan, irinotecan, camptothecin, 9-aminocamptothecin, paclitaxel, docetaxel, daunorubicin, doxorubicin, dactinomycin, idarubincin, plicamycin, mitomycin, amsacrine, bleomycin, aminoglutethimide, anastrozole, finasteride, ketoconazole, tamoxifen, flutamide, leuprolide, goserelin, Gleevec™ (Novartis), leflunomide (Pharmacia), SU5416 (Pharmacia), SU6668 (Pharmacia), PTK787 (Novartis), Iressa™ (AstraZeneca), Tarceva™, (Oncogene Science), trastuzumab (Genentech), Erbitux™ (ImClone), PKI166 (Novartis), GW2016 (GlaxoSmithKline), EKB-509 (Wyeth), EKB-569 (Wyeth), MDX-H210 (Medarex), 2C4 (Genentech), MDX-447 (Medarex), ABX-EGF (Abgenix), CI-1033 (Pfizer), Avastin™ (Genentech), IMC-1C11 (ImClone), ZD4190 (AstraZeneca), ZD6474 (AstraZeneca), CEP-701 (Cephalon), CEP-751 (Cephalon), MLN518 (Millenium), PKC412 (Novartis), 13-cis-retinoic acid, isotretinoin, retinyl palmitate, 4-(hydroxycarbophenyl) retinamide, misonidazole, nitracrine, mitoxantrone, hydroxyurea, L-asparaginase, interferon alfa, AP23573, Cerivastatin, Troglitazone, CRx-026DHA-paclitaxel, Taxoprexin, TPI-287, Sphingosine-based lipids, and mitotane.

Corticosteroids

Exemplary corticosteroids which can be used in the methods and compositions of the invention include, without limitation, 21-acetoxypregnenolone, alclomerasone, algestone, amcinonide, beclomethasone, betamethasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flunisolide, flucinolone acetonide, fluocinonide, fluorocinolone acetonide, fluocortin butyl, fluocortolone, fluorocortolone hexanoate, diflucortolone valerate, fluorometholone, fluperolone acetate, fluprednidene acetate, fluprednisolone, flurandenolide, formocortal, halcinonide, halometasone, halopredone acetate, hydrocortamate, hydrocortisone; hydrocortisone acetate, hydrocortisone butyrate, hydrocortisone phosphate, hydrocortisone 21-sodium succinate, hydrocortisone tebutate, mazipredone, medrysone, meprednisone, methylprednicolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, predníval, prednylidene, prednylidene 21-diethylaminoacetate, tixocortol, triamcinolone, triamcinolone acetonide, triamcinolone benetonide and triamcinolone hexacetonide. Structurally related corticosteroids having similar anti-inflammatory properties are also intended to be encompassed by this group.

NSAIDs

Exemplary non-steroidal antiinflammatory drugs (NSAIDs) which can be used in the methods and compositions of the invention include, without limitation, naproxen sodium, diclofenac sodium, diclofenac potassium, aspirin, sulindac, diflunisal, piroxicam, indomethacin, ibuprofen, nabumetone, choline magnesium trisalicylate, sodium salicylate, salicylsalicylic acid (salsalate), fenoprofen, flurbiprofen, ketoprofen, meclofenamate sodium, meloxicam, oxaprozin, sulindac, and tolmetin.

Analgesics

Exemplary analgesics which can be used in the methods and compositions of the invention include, without limitation, morphine, codeine, heroin, ethylmorphine, O-carboxymethylmorphine, O-acetylmorphine, hydrocodone, hydromorphone, oxymorphone, oxycodone, dihydrocodeine, thebaine, metopon, ethorphine, acetorphine, diprenorphine, buprenorphine, phenomorphan, levorphanol, ethoheptazine, ketobemidone, dihydroetorphine and dihydroacetorphine.

Antimicrobials

Exemplary antimicrobials which can be used in the methods and compositions of the invention include, without limitation, penicillin G, penicillin V, methicillin, oxacillin, cloxacillin, dicloxacillin, nafcillin, ampicillin, amoxicillin, carbenicillin, ticarcillin, mezlocillin, piperacillin, aziocillin, temocillin, cepalothin, cephapirin, cephradine, cephaloridine, cefazolin, cefamandole, cefiroxime, cephalexin, cefprozil, cefaclor, loracarbef, cefoxitin, cefnatozole, cefotaxime, ceftizoxime, ceftriaxone, cefoperazone, ceftazidime, cefixime, cefpodoxime, ceftibuten, cefdinir, cefpirome, cefepime, BAL5788, BAL9141, imipenem, ertapenem, meropenem, astreonam, clavulanate, sulbactam, tazobactam, streptomycin, neomycin, kanamycin, paromycin, gentamicin, tobramycin, amikacin, netilmicin, spectinomycin, sisomicin, dibekalin, isepamicin, tetracycline, chlortetracycline, demeclocycline, minocycline, oxytetracycline, methacycline, doxycycline, erythromycin, azithromycin, clarithromycin, telithromycin, ABT-773, lincomycin, clindamycin, vancomycin, oritavancin, dalbavancin, teicoplanin, quinupristin and dalfopristin, sulphanilamide, para-aminobenzoic acid, sulfadiazine, sulfisoxazole, sulfamethoxazole, sulfathalidine, linezolid, nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, gatifloxacin, moxifloxacin, gemifloxacin, sitafloxacin, metronidazole, daptomycin, garenoxacin, ramoplanin, faropenem, polymyxin, tigecycline, AZD2563, and trimethoprim.

Local Anesthetics

Exemplary local anesthetics which can be used in the methods and compositions of the invention include, without limitation, cocaine, procaine, lidocaine, prilocalne, mepivicaine, bupivicaine, articaine, tetracaine, chloroprocaine, etidocaine, and ropavacaine.

Antispasmodic

Exemplary antispasmodics which can be used in the methods and compositions of the invention include, without limitation, atropine, belladonna, bentyl, cystospaz, detrol (tolterodine), dicyclomine, ditropan, donnatol, donnazyme, fasudil, flexeril, glycopyrrolate, homatropine, hyoscyamine, levsin, levsinex, librax, malcotran, novartin, oxyphencyclimine, oxybutynin, pamine, tolterodine, tiquizium, prozapine, and pinaverium.

Admixtures with Base Polymers

Where the grafted polymer of the invention does not have base polymer properties (e.g., where the linear backbone segment is less than 10 KDa), it may be desirable to prepare an admixture with a base polymer to produce the requisite mechanical properties, e.g., for a shaped article. Desirably, the grafted polymer of the invention is concentrated within the nm region of the exterior polymer interface and is designed to be thermodynamically compatible with the base polymer to prevent uneven distribution of the grafted polymer at the surface.

Many materials having base polymer properties are known in the art. Base polymers useful in the admixtures of the invention can include, without limitation, polyurethane, polysulfones, polycarbonates, polysaccharides, polyesters, polyethylene, polypropylene, polystyrene, poly(acrylonitrile-butadienestyrene), polybutadiene, polyisoprene, styrenebutadiene-styrene block copolymers, styrene-isoprenestyrene block copolymers, poly-R-methylpentene, polyisobutylene, polymethyl-methacrylate, polyvinylacetate-polyacrylonitrile, polyvinyl chloride, polyethyleneterephthalate, cellulose and its esters and derivatives, polyamides, polyester-polyethers, styrene-isoprenes, styrenebutadienes, thermoplastic polyolefins, styrene-saturated olefins, polyester-polyester, ethylene-vinyl acetate ethylene-ethyl acrylate, ionomers, and thermoplastic polydienes.

Shaped Articles

Articles of the invention can be formed from grafted polymers of the invention used either alone or as an admixture with a base polymer. One advantage of using a grafted polymer of the invention alone as the base polymer to form a shaped article is because there is no polymer mixing, there is no reduction in entropy and no possibility of phase separation.

Any shaped article can be made using the compositions of the invention. For example, articles suitable for contact with bodily fluids, such as medical devices can be made using the compositions described herein. The duration of contact may be short, for example, as with surgical instruments or long term use articles such as implants. The medical devices include, without limitation, catheters, guide wires, vascular stents, micro-particles, electronic leads, probes, sensors, drug depots, transdermal patches, vascular patches, blood bags, and tubing. The medical device can be an implanted device, percutaneous device, or cutaneous device. Implanted devices include articles that are fully implanted in a patient, i.e., are completely internal. Percutaneous devices include items that penetrate the skin, thereby extending from outside the body into the body. Cutaneous devices are used superficially. Implanted devices include, without limitation, prostheses such as pacemakers, electrical leads such as pacing leads, defibrillarors, artificial hearts, ventricular assist devices, anatomical reconstruction prostheses such as breast implants, artificial heart valves, heart valve stents, pericardial patches, surgical patches, coronary stents, vascular grafts, vascular and structural stents, vascular or cardiovascular shunts, biological conduits, pledges, sutures, annuloplasty rings, stents, staples, valved grafts, dermal grafts for wound healing, orthopedic spinal implants, orthopedic pins, intrauterine devices, urinary stents, maxial facial reconstruction plating, dental implants, intraocular lenses, clips, sternal wires, bone, skin, ligaments, tendons, and combination thereof. Percutaneous devices include, without limitation, catheters or various types, cannulas, drainage tubes such as chest tubes, surgical instruments such as forceps, retractors, needles, and gloves, and catheter cuffs. Cutaneous devices include, without limitation, burn dressings, wound dressings and dental hardware, such as bridge supports and bracing components.

An implantable medical device as described above is generally structured from a base metallic or polymeric platform in a solid state format. The grafted polymer of the invention within this primary platform, either alone or as an admixture, controls the release of therapeutic agents from the device.

The methods and compositions of the invention can also be used to deliver an active agent to the surface of a cosmoceutical (e.g., creams, gels, and lotions), to a pellet, e.g., for controlling the proliferation of pests, such as weeds or insects, or to a membrane, for example, for use in a water purification process in which an antibacterial agent is released into the water.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Synthesis of Grafted Polymers Using ATRP Chemistry General Experimental Protocols Purification: A number of purification techniques have been used in the experimental section. A brief summary of each technique is noted below:

Dialysis: Size exclusion purification is where a membrane separates molecules based on their size in solution. Lower molecular weight molecules pass through dialysis membranes into a large volume of solvent. In this series of experimental protocols the membrane used was SpectraPor 6 Regenerated Cellulose (RC).

Column chromatography: The stationary phase used for column chromatography is typically silica gel. In general, fluorinated compounds do not interact with silica. This allowed for a rapid filtration of smaller molecules.

Solid Phase Extraction (Cationic): A pre-packed cationic silica gel column (plastic) was used to remove small cationic compounds from the reaction mixtures.

Ultrafiltration (Centricon and Pellicon): This technique is based on a separation process, using a semi-permeable membrane to separate large molecules from small compounds. A solution of oligofluoro (OF) was pressurized over a membrane using tangential flow to separate larger molecules from smaller ones.

Fluorous Solid Phase Extraction (F—SPE): SPE substrates modified with perfluorinated ligands (F—SPE) were used to selectively retain the OF, allowing the separation of non-fluorinated compounds.

Cytotoxicity Assay: Polymeric compounds synthesized in the experimental section were profiled for cytotoxicity. A brief description of the test is summarized as follows.

Direct Contact Cytotoxicity Assay: The viability of HeLa epithelial cells in direct contact with test materials was used to assess the potential cytotoxicity of oligofluoro (OF). A sample of test material was solvent cast on an agar-supported Supor filter. Subsequently, a monolayer of HeLa cells were cultured directly on the filter, in the presence of MEM culture media. After 24 hours of incubation, the Supor filter was rinsed and stained with succinic dehydrogenase. Viable cells were identified by a positive purple stain and the cytotoxicity was determined by examining the stained filter for cell exclusion zones around the cast material, or a low cell density.

Dehalogenation: In the following sections, polymers synthesized by atom transfer radical polymerization (ATRP)

have defined terminal groups, based on the initiator selection. Alkyl halides (synthesized using BIBB, TCAA, or TCE) were used as the initiators and the halogenation occurred at the precursor pendent groups. To remove the halogen end groups a one-pot reaction was used. The dehalogenation was completed immediately after polymerization using trialkyltinhydride.

Precursor to Macroinitiator

| Compound ID | Description |
|---|---|
| Precursor with Ester Functional Group | |
| (Compound 1-ester) | (BAL-LDI)$_2$-PTMO |
| Precursor with Terminal Carboxylic Functional Group | |
| (Compound 1-acid) | (BAL-LDI(COOH))$_2$-PTMO |
| Precursor with Terminal Hydroxy Functional Groups | |
| (Compound 2a) | (BAL-LDI(Tris))$_2$-PTMO: EDC method |
| (Compound 2b) | (BAL-LDI(Tris))$_2$-PTMO: K$_2$CO$_3$ method |
| (Compound 3') | (BAL-LDI(EA))$_2$-PTMO |

The first phase of the atom transfer radical polymerization (ATRP) requires the synthesis of precursor molecules from which the macroinitiators are generated. These precursors can include molecules such as (BAL-LDI)$_2$—PTMO (compound 1) with acid or ester functional groups. The introduction of other functional groups in the molecular structure of these precursors are also demonstrated in this section. This strategy provides oligomeric platforms with functional groups specific for terminal halogenation and for conversion reactions. Furthermore this strategy provides an excellent degree of freedom in initiator and catalyst design and selection.

Polytetramethyleneoxide (10 grams, 0.0097 mol, predried) was dissolved in DMAc (50 mL). Lysine diisocyanate (4.11 grams, 0.0194 mol, freshly distilled) in DMAc (25 mL) was added dropwise to the polytetramethylene oxide solution. The pre-polymer reaction mixture was sealed and maintained under a nitrogen atmosphere between 60-70° C. for two hours. The end capping agent, (11.74 grams, 0.0194 mol), was dissolved in DMAc (25 mL) and added dropwise to the pre-polymer reaction mixture. The reaction solution was sealed under a nitrogen atmosphere and stirred overnight at room temperature. Dibutyltin dilaurate was used as the catalyst. The product was precipitated in a mixture of water and ether for the recovery of the catalyst and removal of residual fluoro alcohol. The final product was dried under vacuum. NMR and IR analysis confirmed the presence of methyl ester groups. $^1$H NMR (300 MHz, CDCl$_3$) δ (ppm) 4.65-5.43 (1, 16, 17), 4.24-4.46 (15), 3.94-4.13 (18), 3.74 (2), 3.28-3.50 (11), 2.98-3.28 (6), 2.29-2.60 (12), 1.16-1.96 (3, 4, 5, 9, 10). HPLC analysis: retention time of 39.5 minutes (compound 1-ester). Reversed phase HPLC, C18 column, methanol and pH 9 PBS mobile phase (gradient). DSC analysis: Tg=−66.6° C. XPS analysis (blend): (compound 1-ester) was blended into a Chronothane 80A base polymer as a 5 wt % additive, using DMAc solvent to make a 0.1 g/mL solution. Films of the blend were cast in Teflon molds, and cured at 50° C. for 24 hours, followed by drying under vacuum at 50° C. for 24 hours. The air-contacting surface of the film was analyzed by XPS, using a 90° take-off angle. Elemental analysis of Chronothane, C, 87.1%; N, 3.2%; O, 8.6%; F, 0%; Chronothane+5 wt % (compound 1-ester), C, 50.4%; N, 2.9%; O, 9.1%; F, 37.4%.

SYNTHESIS of α,ω-BAL-poly(LDI/PTMO) (COMPOUND 1).

(Compound 1-ester) - Ester functional group

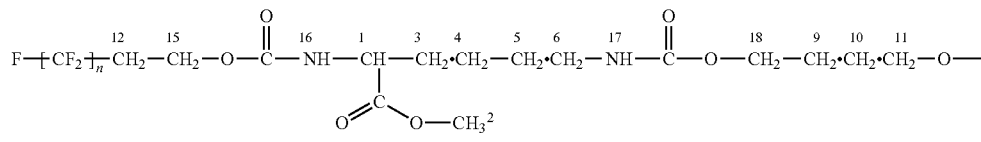
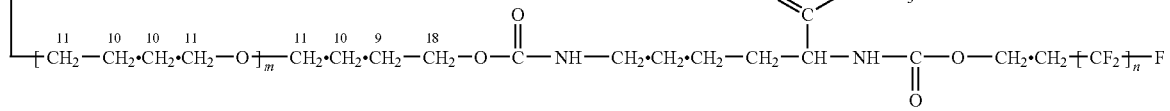

(Compound 1-acid)-Acid functional group

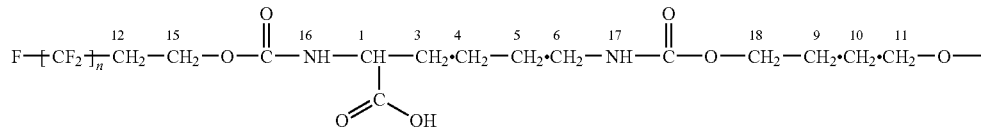
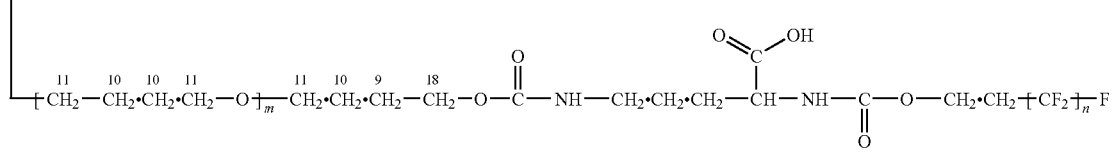

The hydrolysis of the ester groups to carboxylic groups was completed using 1 N hydrochloric acid solution. The final product was precipitated in 1 N aqueous KCl and washed and dried under vacuum at 60° C. The conversion of ester groups to acid functional groups was further confirmed by NMR analysis. Proton NMR indicated the disappearance of methoxy groups. $^1$H NMR (300 MHz, CDCl$_3$) δ (ppm) 4.75-5.78 (1, 16, 17), 4.27-4.46 (15), 3.97-4.23 (18), 3.74 (2), 3.33-3.54 (11), 3.06-3.27 (6), 2.35-2.55 (12), 1.21-1.95 (3, 4, 5, 9, 10). HPLC analysis: retention time of 33.4 minutes (compound 1-acid). Reversed phase HPLC, C18 column, methanol and pH 9 PBS mobile phase (gradient). DSC analysis: Tg=−65° C. XPS analysis (blend): (compound 1-acid) was blended into a Chronothane 80A base polymer as a 5 wt % additive, using DMAc solvent to make a 0.1 g/mL solution. Films of the blend were cast in Teflon molds, and cured at 50° C. for 24 hours, followed by drying under vacuum at 50° C. for 24 hours. The air-contacting surface of the film was analyzed by XPS, using a 90° take-off angle. Elemental analysis of Chronothane, C, 87.1%; N, 3.2%; O, 8.6%; F, 0%; Chronothane+5 wt % (compound 1-acid), C, 51.4%; N, 3.4%; O, 8.4%; F, 36.1%. The XPS analysis area was 700×300 microns in size. IR analysis was in accordance with the chemical structure: 3327.29 cm$^{-1}$ ν(N—H)H-bonded, 2945.10 cm$^{-1}$ ν(C—H) CH2 asymmetric stretching, 2865.69 cm$^{-1}$ ν(C—H)CH2 symmetric stretching, 1717.91 cm$^{-1}$ ν(C=O) urethane amide, 1533.54 cm$^{-1}$ ν(C—N) stretching mode, 1445.56 cm$^{-1}$ ν(C—N) stretching mode; 1349.31 cm$^{-1}$ ν(C—O) stretching, 1400-1000 cm$^{-1}$ ν(C—F) monofluoroalkanes absorb to the right in the range, while polyfluoroalkanes give multiple strong bands over the range from 1350-1100 cm$^{-1}$. Elemental analysis $C_{92}H_{148}O_{25}N_4F_{30}$ was in accordance with the expected structure [% C, 48.56% (50.34% (−1.76%)); % H, 6.87% (7.07% (−0.2%)); % N, 2.53% (2.7% (−0.17%)); % F, 22.78% (20.37% (2.41%))].

hours at room temperature. The DMF solvent was evaporated at 40° C. The viscous residual was extracted with 3 100 mL diethyl ether at room temperature. EDC and Tris are insoluble in cold ether. The clear ether solution was evaporated. The white viscous product (compound 2a) was dried under vacuum at 40° C. overnight. Elemental analysis: C, theoretical, 46.33%; measured 49.96%; H, theoretical 6.25%; measured 5.78%; N, theoretical 3.21%; measured 4.51%; F, theoretical 25.86%; measured 25.57%; O, theoretical 18.35%; measured 14.60%. IR analysis: 3330 cm$^{-1}$ ν(O—H), 1110 cm$^{-1}$ ν(C—OH), 1160 cm$^{-1}$ ν(C—F), 1220 cm$^{-1}$ ν(C—O—C). $^1$H NMR (300 MHz, CDCl$_3$) δ (ppm) 2.38 (s, 3H, $C_{Tris}$CH$_2$OH), 1.73 (t, 1H, $C_{Tris}$-NH). Determination of the OH number: the hydroxyl content of (compound 2a) (which is unique to the pendent Tris) was determined by reacting (compound 2a) with excess acetic anhydride in pyridine, followed by back-titration with potassium hydroxide base using phenolphthalein as an indicator. Result: OH number 2.4113 mmol/g (theory: 2.4108 mmol/g).

Method B: K$_2$CO$_3$ conjugation of Tris

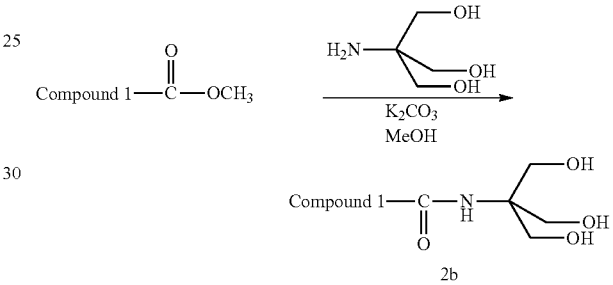

(Compound 1-ester) (3.05 g, ~2.6 mmol ester) was transferred into an oven dried two-neck flask (250 mL) and degassed for 2 hours. Anhydrous methanol (100 mL) was SYNTHESIS OF a,w-BAL-poly(LDI(Tris)/PTMO) (COMPOUND 2).

Method A: EDC conjugation of Tris

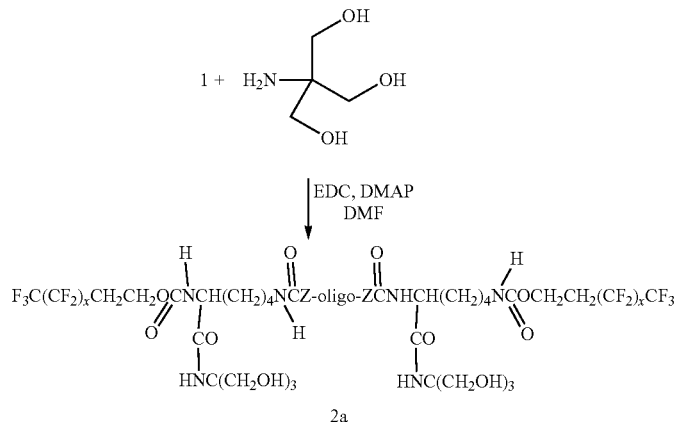

10 g of (compound 1-acid), EDC and DMAP (in a 1:6:0.5 molar ratio of acid groups:EDC:DMAP) were dissolved in 200 mL of anhydrous DMF. Tris (in a 1.1:1 molar ratio of Tris:acid groups) was added to the reaction mixture. This solution was reacted under a nitrogen atmosphere for 24 added to the flask by double ended needle transfer. The reaction mixture was stirred until everything was in solution. A mixture of tris hydroxymethyl aminoethane (Tris, 0.63 g, 5.2 mmol) and anhydrous potassium carbonate (0.72 g, 5.2 mmol) was added. This reaction mixture was refluxed at 45°

C. for seven days. The reaction mixture was cooled, the solution was purified using cationic exchange and fluorous solid phase reaction. The final product was dried under vacuum for 48 hours (50° C.). $^1$H NMR (300 MHz, CDCl$_3$) δ (ppm) 4.83-5.78 (1, 16, 17), 4.25-4.50 (15), 3.95-4.20 (18), 3.75 (reduced CH$_3$ signal), 3.57-3.83 (Tris CH$_2$), 3.30-3.56 (11), 3.04-3.28 (6), 2.29-2.59 (12), 1.17-1.97 (3, 4, 5, 9, 10). HPLC analysis: retention time shifted from 39.5 minutes (compound 1-ester) to 34.6 minutes (compound 2b). Reversed phase HPLC, C18 column, methanol and pH 9 PBS mobile phase (gradient). XPS analysis (blend): (compound 2b) was blended into a Carbothane 85A base polymer as a 5 wt % additive, using DMAc solvent to make a 0.1 g/mL solution. Films of the blend were cast in Teflon molds, and cured at 50° C. for 24 hours, followed by drying under vacuum at 50° C. for 24 hours. The air-contacting surface of the film was analyzed by XPS, using a 90° take-off angle. Elemental analysis of Carbothane, C, 87.0%; N, 4.3%; O, 7.5%; F, 0%; Carbothane+5 wt % (compound 2b), C, 45.0%; N, 5.5%; O, 13.0%; F, 36.3%. Contact angle analysis: (compound 2b) was blended into Carbothane 85A and ethylene-co-vinyl acetate (EVA) as 5 wt % mixtures, using solvent casting techniques. Contact angle analysis was performed using water. EVA: 105°±/−2° (hydrophobic), EVA+(compound 2b): 15°+/−2° (hydrophilic). Carbothane 85A: 102°±/−4° (hydrophobic), Carbothane+(compound 2b): 18°+/−5° (hydrophilic).

(Compound 1-ester) (4.002 g, ~3.4 mmol ester) was transferred into an oven dried two-neck flask (250 mL) and degassed overnight. Anhydrous methanol (135 mL) was added to the reaction mixture by double ended needle transfer. The reaction mixture was stirred until everything was in solution. A mixture of ethanolamine (0.42 g, 6.8 mmol) and anhydrous potassium carbonate (0.94 g, 6.8 mmol) was added. This reaction mixture was refluxed at 45° C. for seven days. The final product was purified and dried under vacuum for 48 hours (30° C.). $^1$H NMR (300 MHz, CDCl$_3$) δ (ppm) 4.75-5.90 (1, 16, 17), 4.23-4.56 (15), 3.93-4.22 (18), 3.58-3.90 (ethanolamine), 3.27-3.58 (11), 3.03-3.27 (6), 2.21-2.59 (12), 1.13-2.05 (3, 4, 5, 9, 10). HPLC analysis: retention time shifted from 39.5 minutes (compound 1-ester) to 37.4 minutes (compound 3'). Reversed phase HPLC, C18 column, methanol and pH 9 PBS mobile phase (gradient).

Monofunctional Macroinitiators

| Example No. | Compound ID | Description |
| --- | --- | --- |
| 1 | (Compound 3) | (BAL-LDI-p-AEE)$_2$-PTMO |
|   | (Compound 4) | (BAL-LDI-p-AEE-Br)$_2$-PTMO |
| 2 | (Compound 5) | (BAL-HDI-DABS)$_2$-PTMO |
|   | (Compound 6) | (BAL-HDI-DABS-p-OXC)$_2$-PTMO |

The second phase of the ATRP process involves the synthesis of the macroinitator. Macroinitiators are constructed with mono or multi initiator sites. This section introduces mono-initiator ATRP precursors that are synthesized via halogenation of mono hydroxyl or sulphonate groups. Other functional groups can be halogenated using similar reaction pathways.

SYTHESIS of α,ω-BAL-poly(LDI(ethanolamine)/PTMO) (COMPOUND 3').

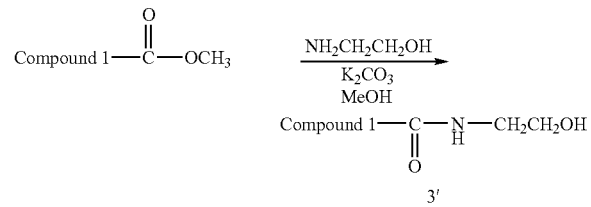

EXAMPLE 1: Monofunctional bromo-macroinitiator (BMI) synthesized by coupling BIBB to α,ω-BAL-Poly(LDI/diol) pendent carboxylic acid precursor by two steps (COMPOUND) 4).

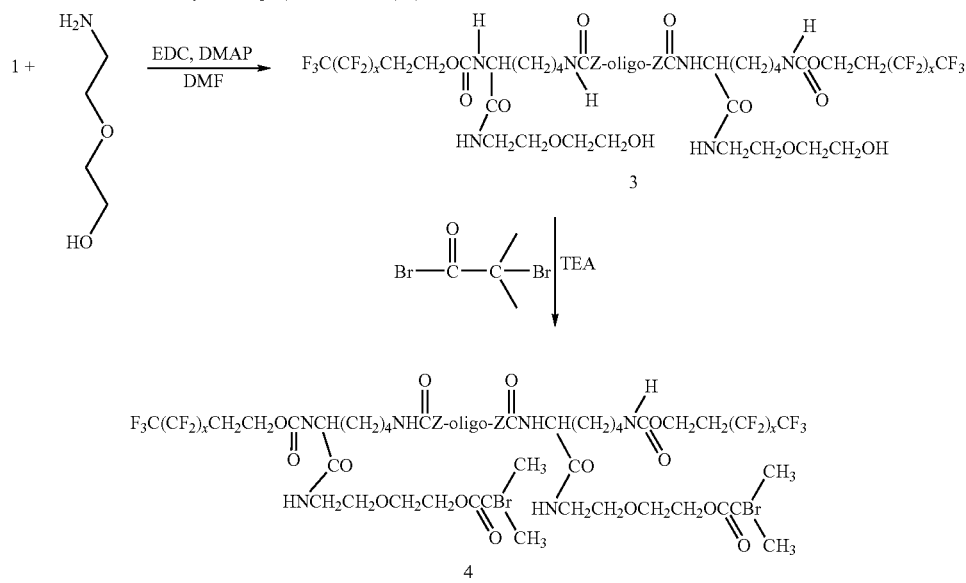

Step 1: Coupling of AEE to α,ω-BAL-Poly(LDI/PTMO) Acid Precursor (Compound 3).

2 g of (compound 1-acid), EDC and DMAP (in a 1:6:0.5 molar ratio of acid groups:EDC:DMAP) were dissolved in 50 mL of anhydrous $CH_2Cl_2$. AEE (in a 1.1:1 molar ratio of AEE:acid groups) was added. This solution was reacted under a nitrogen atmosphere for 24 hours at room temperature. The $CH_2Cl_2$ solvent was evaporated at room temperature. The viscous residue was extracted with 3 100 mL diethyl ether at room temperature. EDC is insoluble in cold ether. The extracted clear ether solution was evaporated. The white viscous product (compound 3) was dried under vacuum at 60° C. overnight. Elemental analysis: C, theoretical 46.90%; measured 49.98%; H, theoretical 6.33%; measured 7.70%; N, theoretical 3.25%; measured 5.040%; F, theoretical 26.18%; measured 19.92%; O, theoretical 17.34%; measured 17.36%. The theoretical hydroxyl group number was 0.773 mmol/g and the measured value by titration was 0.814 mmol/g. $^1$H NMR (300 MHz, $CDCl_3$) was compared with (compound 1-acid) and the following expected changes were assigned: δ (ppm) 3.46 (d, $CH_2OH$), 2.35 (t, OH), 3.40 (m, $CH_2OCH_2$), 2.20 (t, $C_{AEE}NH$), 2.17 ($N_{AEE}CH_2$).

Step 2: Synthesis of BMI by Coupling BIBB to α,ω-BAL-Poly(LDI/PTMO) Pendent AEE Precursor (Compound 4).

10 g of (compound 3) (dried previously) and TEA (in a 1.2:1 molar ratio of TEA:OH groups) were dissolved in 300 mL of anhydrous $CH_2Cl_2$ under a nitrogen atmosphere. The solution was cooled in an ice-water bath. A 10% excess quantity of 10% $BIBB/CH_2Cl_2$ solution was added dropwise to the (compound 3)/$CH_2Cl_2$ solution under a nitrogen atmosphere. The mixture was stirred for 20 hours at room temperature. This was followed by filtration to remove the TEA-HBr salt. The filtrate was washed with 30 mL water three times. The volatiles of the oil phase were evaporated at room temperature. A pale brown viscous solid BMI (compound 4) was obtained. Elemental analysis: C, theoretical 45.39%; measured 45.39%; H, theoretical 6.02%; measured 6.02%; N, theoretical 2.91%; measured 2.91%; F, theoretical 23.43%; measured 23.43; O, theoretical 16.66%; measured 16.65%; Br, theoretical 5.54%; measured 5.54%. $^1$H NMR (300 MHz, $CDCl_3$) was compared with (compound 3) and the following identifying shifts were found: δ (ppm) 3.75 (m, $C_{IBB}OOCH_2$). The OH signal was eliminated as per the chemistry described above.

EXAMPLE 2: Synthesis of monofunctional benzenesulphonate chloride macroinitiator (SCMI) (COMPOUND 6).

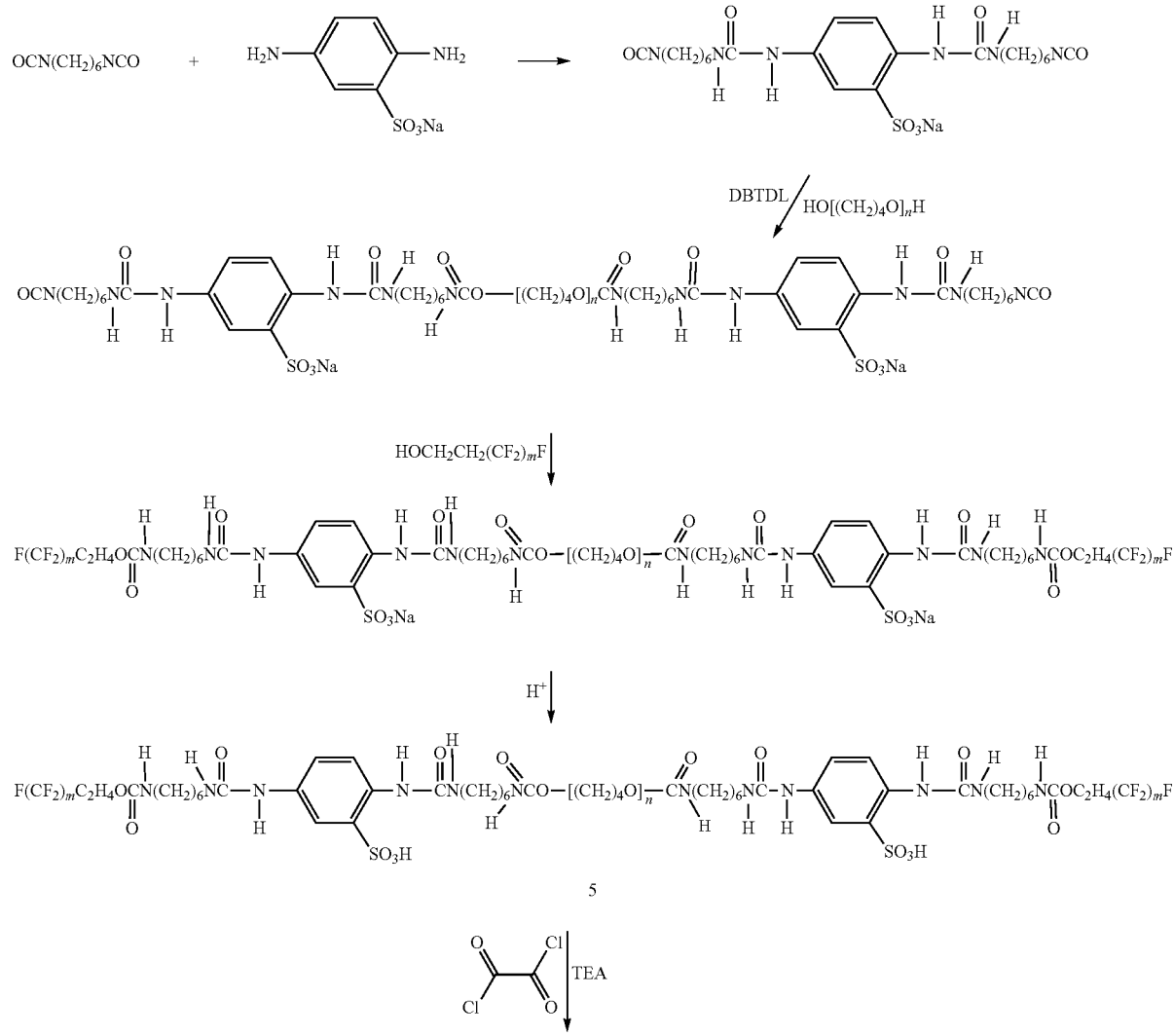

-continued

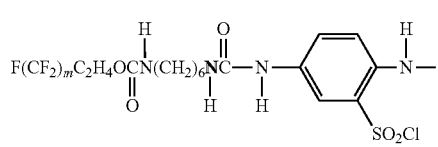 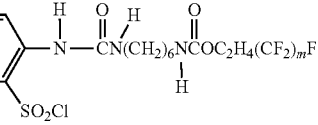

SCMI is an example of a precursor where the pendent monofunctional [ini] group differs from the previous example. This compound is synthesized with a different linkB molecule. In this example linkB is synthesized with diamino benzene sulfonic acid which is reacted with HDI to produce a new diisocyanate linking molecule, to be used as both the linkA and linkB reactants. The pendent sulfonic acid group is representative of linkC. The latter is reacted with PTMO (molecular weight of 1000). Hence, PTMO was used as the oligo component and the fluoro alcohol was used as the fluoro component. The sulphonyl group can react further with OXC or TCAA to introduce the [ini] component. This SCMSM will be referred to SCMI, throughout this text.

4.204 g (20 mmol) of DABSNa dissolved in 250 mL of DMAc was added dropwise into a solution of HDI/DMAc (6.728 g (40 mmol)/50 mL) at room temperature. Another 20 mL of DMAc was used to wash the DABSNa container and was added to the reactor. The reaction solution was stirred for 5 minutes. 10 g (10 mmol) of PTMO in 20 mL of DMAc and 0.05 mL of DBTDL were added into the reactor. Another 10 mL of DMAc was used to wash the PTMO container and was added to the reactor. The reactor contents were then stirred at 60° C. for 4 hours. 9.8 g (20.2 mmol) of BAL and 0.05 mL of DBTDL were added to the reaction and stirred at 60° C. for 20 hours. After evaporating most of the DMAc, the cold concentrated solution was dissolved in water, and precipitated by adding 4.227 g (22 mmol) of citric acid. The solid was washed by water till neutral. The product (compound 5) of this step was dried under vacuum at room temperature for 4 hours then at 60° C. overnight. Elemental analysis: C, calculated 47.98%; found 48.00%; H, calculated 6.36%; found 7.88%; N, calculated 5.45%; found 6.95%; F, calculated 22.00%; found 15.33%; O, calculated 16.13%; found 19.70%; S, calculated 2.08%; found 2.14%. IR analysis: 3350 cm$^{-1}$ v(N—H)H-bond, 2927 cm$^{-1}$ v(CH$_2$) asymmetric stretch, 2855 cm$^{-1}$ v(CH$_2$) symmetric stretch, 1740 cm$^{-1}$ v(C=O)H-bond, 1700 cm$^{-1}$ v(C—O) H-bond, 1493 cm$^{-1}$ and 1452 cm$^{-1}$ v(C=C) aromatic ring, 1400-1000 cm$^{-1}$ v(C—F), 1208 cm$^{-1}$ v(S=O). Halogenation of the sulfonic acid on linkC was carried out by reacting with oxalyl chloride (OXC) in a nitrogen atmosphere. 2.979 g (Ar—SO$_3$H, 2 mmol) of (compound 5) and 0.279 g (2 mmol) of TEA were dissolved in 25 mL of anhydrous DMF. This solution was first cooled to 0° C. using an ice bath. OXC solution was added stoichiometrically (0.175 mL, 2 mmol) to (compound 5) to react with sulphonyl groups. The reaction solution was stirred for 30 minutes at 0° C., and then at room temperature for 1 hour. Given the inherent reactivity of (compound 6), the reaction mixture was directly used to synthesize (compound 8) in example 3. Elemental analysis of (compound 6): theoretical, C, 48.20%; H, 6.43%; Cl, 2.35%; F, 19.90%; N, 5.57%; O, 15.42%; S, 2.13%.

Multifunctional Macroinitiators

| Example No. | Compound ID | Description |
| --- | --- | --- |
| 3 | (Compound 7) | (BAL-HDI-DABS-p-TCE)$_2$-PTMO |
| 4, 4' | (Compound 8) | (BAL-LDI-p-TCAA)$_2$-PTMO |
| 5 | (Compound 9) | (BAL-LDI-p-TCE)$_2$-PTMO |
| 6 | (Compound 2) | (BAL-LDI-p-Tris)$_2$-PTMO |
|  | (Compound 11) | (BAL-LDI-p-Tris-Br)$_2$-PTMO |
| 7 | (Compound 13) | (BAL-LDI-p-RGD-Br)$_2$-PTMO |

Multifunctional initiator precursor molecules can also be used in the ATRP synthesis. This section highlights the multihalogenation of oligomeric compounds with sulphonate, carboxylic, hydroxyl, and primary amide functional groups. Examples of multifunctional initiators are provided in this section.

EXAMPLE 3: Synthesis of tri-functional macroinitiator (tSCMI) synthesis by coupling TCE to sulphonate (COMPOUND 7).

6 + HOCH$_2$CCl$_3$

↓ TEA

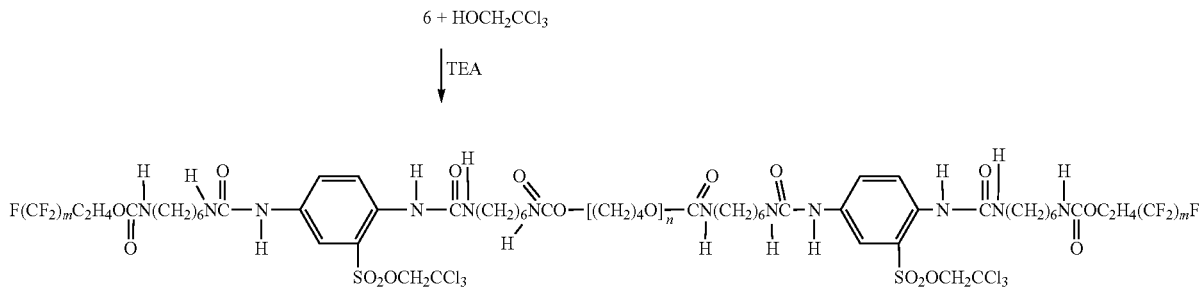

As shown in examples 4, 4' and 5, it is possible to generate trichloro initiator macromolecules for use in the invention, however the reaction and ease of synthesis is facilitated for non-amine containing moieties such as TCE (example 5) vs amine containing moieties such as TCAA (example 4). For the purpose of demonstrating the conversion of a mono-initiator into a tri-functional initiator, TCE was selected based on the above rationale.

The final product from example 2 (compound 6) was cooled in an ice bath for 15 minutes. A solution of TCE (0.314 g, 2.1 mmol) and 0.30 g of TEA in 10 mL of anhydrous DMF was added dropwise. The reaction mixture was stirred at 0° C. for 30 minutes. The ice bath was removed and the reaction flask was allowed to stir at room temperature for 12 hours. The reaction mixture was added dropwise into a beaker containing 300 mL of deionized water, yielding precipitates. Suction filtration of the precipitates and drying the precipitates in a vacuum oven at 45° C. overnight yielded (compound 7). Elemental analysis of (compound 7): C, theoretical 46.32%; measured 52.92%; H, theoretical 6.11%; measured 8.27%; Cl, theoretical 6.56%; measured 2.03%; F, theoretical 18.52%; measured 5.67%; N, theoretical 5.18%; measured 6.84%; O, theoretical 15.33%; measured 17.55%; S, theoretical 1.98%; measured 7.50%. $^1$H NMR (300 MHz, CD$_3$OD) δ (ppm) 810-7.45 (m, ArH), 4.77 (s, OCH$_2$CCl$_3$), 4.45 (m, NH, OCH$_2$CH$_2$CF$_2$), 4.16 (m, NH), 3.80-3.00 (m, CH$_2$NH, CH$_2$OCH$_2$), 2.50-2.30 (m, OCH$_2$CH$_2$CF$_2$), 1.95-1.12 (m, C$_{PU}$H$_2$CH$_2$CH$_2$). The NMR and elemental data confirm the incorporation of the active chlorine initiator site pendent from the aromatic functional group.

EXAMPLE 4: Tri-functional chloro-macroinitiator (tCMI) synthesis by coupling TCAA to pendent carboxylic acid (COMPOUND 8).

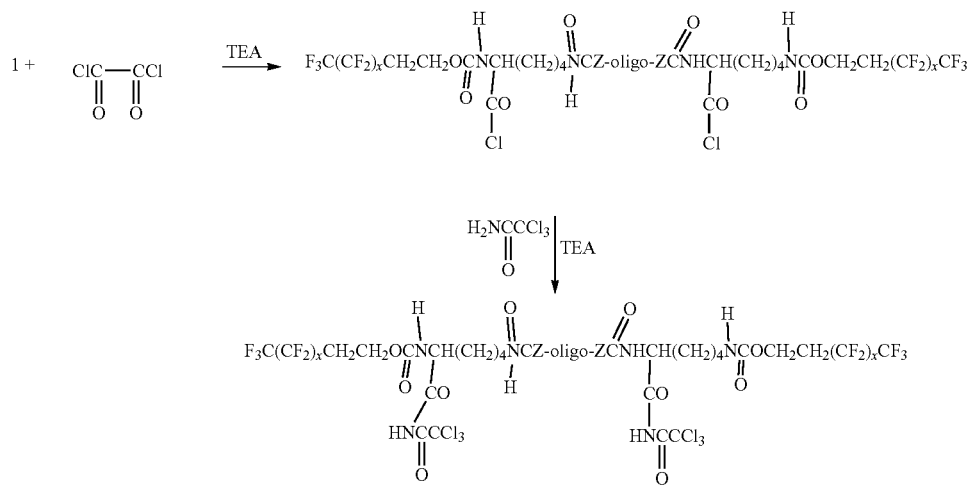

In a nitrogen filled glove bag, 5 g of (compound 1-acid) and 0.611 mL of TEA were dissolved in 90 mL of anhydrous CH$_2$Cl$_2$. The solution was first cooled to 0° C. with an ice-water bath which was placed outside the glove bag. The solution was stirred vigorously and an OXC/CH$_2$Cl$_2$ (0.383 mL/10 mL) solution was added dropwise stoichiometrically. The reaction mixture was stirred at room temperature for 30 minutes. The reaction mixture was added dropwise to a 0° C. cold TCAA/TEA/CH$_2$Cl$_2$ (0.712 g/0.611 mL/90 mL) solution stoichiometrically. The solution was allowed to react for 2 hours at room temperature. After the TEA hydrogen chloride salt was filtered out, the CH$_2$Cl$_2$ solvent was evaporated at room temperature. The solid product was re-dissolved in methanol. The solution was dropped into water and the yellowish product (compound 8) was precipitated. The viscous product was washed with 200 mL of water three times, and dried under vacuum at 40° C. overnight. Elemental analysis: C, theoretical 43.14%; measured 48.45%; H, theoretical 5.39%; measured 7.25%; N, theoretical 3.11%; measured 2.80%; F, theoretical 25.08%; measured 17.82%; O, theoretical 15.42%; measured 23.40%; Cl, theoretical 7.87%; measured 0.64%. The coupling efficiency was calculated to be approximately 8% based on Cl content.

EXAMPLE 4': Tri-functional chloro-macroinitiator (tCMI) synthesis by coupling TCAA to pendent carboxylic acid (COMPOUND 8).

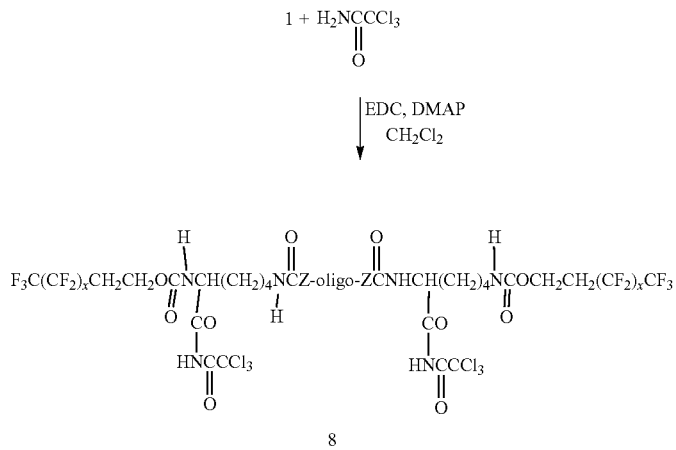

8

Based on example 4, the coupling efficiency of TCAA to (compound 1) via the coupling agent OXC was only 8% (based on elemental analysis). As a result, an alternate approach in coupling TCAA to (compound 1) is demonstrated in this example via the use of EDC as a coupling intermediate.

10 g of (compound 1-acid), EDC and DMAP (in a 1:7.5:1 molar ratio of acid groups:EDC:DMAP) were dissolved in 200 mL of anhydrous $CH_2Cl_2$. TCAA (in a 1.1:1 molar ratio of TCAA:acid groups) was added. This solution was reacted under a nitrogen atmosphere for 7 days at room temperature. The solvent was evaporated at room temperature. The viscous residual was extracted with 3 100 mL diethyl ether at room temperature. The extracted clear ether solution was added into water to remove unreacted TCAA. The precipitated white viscous product (compound 8) was then washed three times with water and dried under vacuum at 40° C. overnight. Elemental analysis: C, theoretical 43.14%; measured 40.75%; H, theoretical 5.39%; measured 7.50%; N, theoretical 3.11%; measured 5.48%; F, theoretical 25.08%; measured 28.45%; O, theoretical 15.42%; measured 15.42%; Cl, theoretical 7.87%; measured 2.65%. The coupling efficiency was calculated to be approximately 34% based on Cl content.

This example demonstrates higher efficiencies over those of examples 4 and 4' for the production of a chlorinated macroinitiator. In this example TCAA is replaced by TCE.

5 g of (compound 1-acid), EDC and DMAP (in a 1:6:0.5 molar ratio of acid groups:EDC:DMAP) were dissolved in 120 mL of anhydrous $CH_2Cl_2$. TCE (in a 1.1:1 molar ratio of TCE:acid groups) was added to the reaction mixture. This solution was reacted under a nitrogen atmosphere for 24 hours at room temperature. The $CH_2Cl_2$ solvent was evaporated at room temperature. The viscous residual was extracted with 3 200 mL diethyl ether at room temperature. The extracted clear ether solution was added dropwise into water to remove unreacted TCE. The precipitated white viscous product (compound 9) was then washed three times with water and dried under vacuum at 40° C. overnight. Elemental analysis: C, theoretical 43.55%; measured 49.59%; H, theoretical 5.52%; measured 7.45%; N, calculated 2.09%; measured 4.43%; O, calculated 15.57%; measured 18.59%; F, calculated 25.32%; measured 18.71%; Cl, calculated 7.95%; measured 3.75%. The coupling efficiency was calculated to be approximately 47.2% based on Cl content. $^1$H NMR (300 MHz, $CDCl_3$) δ (ppm) 4.15 ($CH_2$ of trichloroethyl ester). The coupling efficiency calculated from $^1$H NMR was 53.4%.

EXAMPLE 5: Tri-functional chloro-macroinitiator (tCMI) synthesis by coupling TCE (COMPOUND 9).

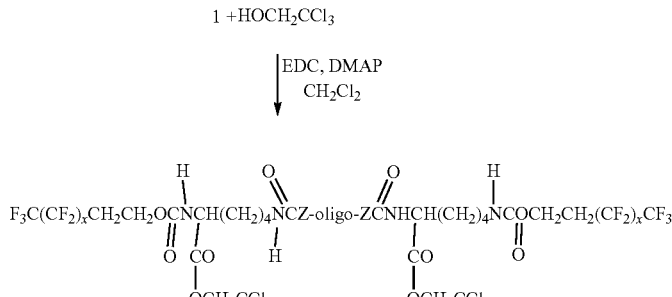

9

EXAMPLE 6: Tri-functional bromo-macroinitiator (tBMI) synthesized by coupling BIBB (COMPOUND 11).

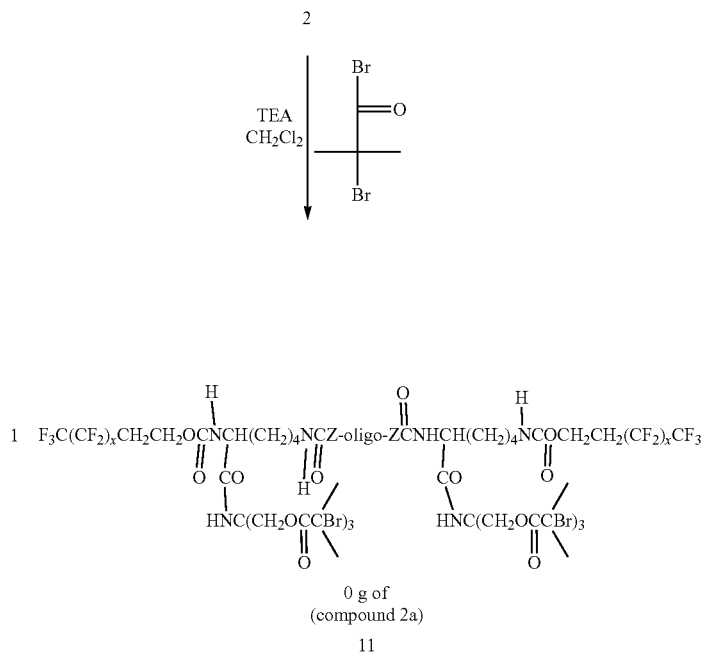

0 g of
(compound 2a)
11

(dried previously) and TEA (in a 1.2:1 molar ratio of TEA:OH groups) were dissolved in 50 mL of anhydrous $CH_2Cl_2$ under a nitrogen atmosphere. The solution was cooled in an ice-water bath. A stoichiometric quantity of 10% BIBB/$CH_2Cl_2$ solution was added dropwise to the (compound 2a)/$CH_2Cl_2$ solution under a nitrogen atmosphere. The mixture was stirred for 24 hours at room temperature, and was filtered to remove the TEA-HBr salt. The filtrate was washed with 10 mL of water three times. The $CH_2Cl_2$ was evaporated at room temperature. A pale brown viscous solid (compound 11) was obtained. Theoretical elemental analysis best estimates based on the structure of the starting precursor materials are given here for comparison purposes. Elemental analysis: C, theoretical 42.75%; measured 44.39%; H, theoretical 5.52%; measured 4.58%; N, theoretical 2.39%; measured 2.91%; F, theoretical 19.29%; measured 17.42%; O, theoretical 16.42%; measured 17.75%; Br, theoretical 13.64%; measured 13.65%. $^1$H NMR (300 MHz, $CDCl_3$) δ (ppm) 2.05 ($C(CH_3)_2Br$).

EXAMPLE 7: Synthesis of α,ω-BAL-Poly(LDI/PTMO) pendent peptide bromo-macroinitiator RBMI (COMPOUND 13).

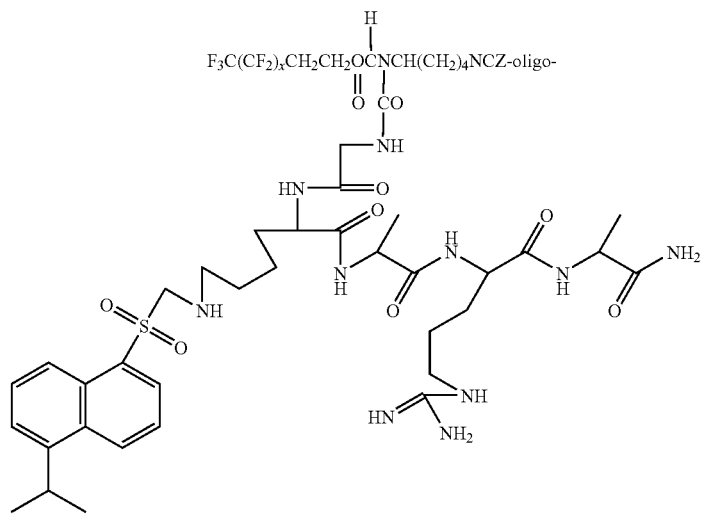

-continued
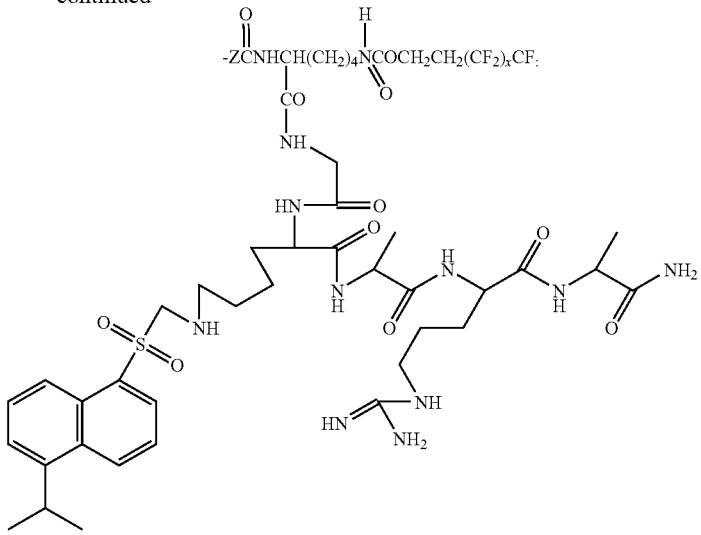
12
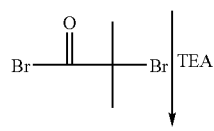
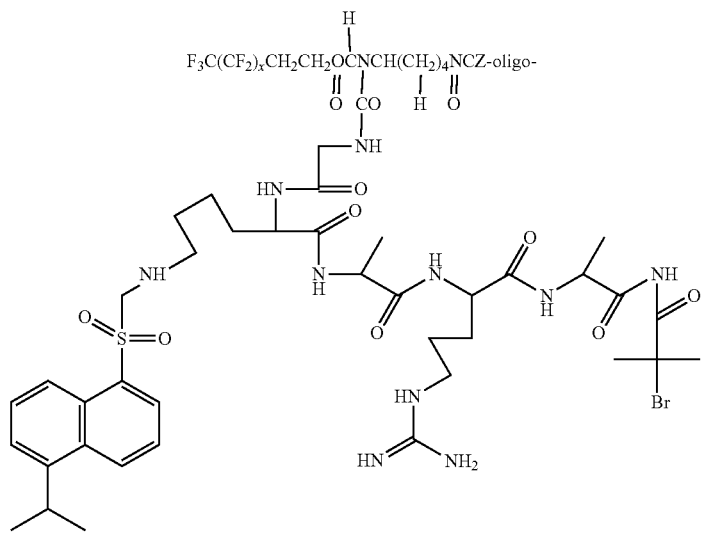

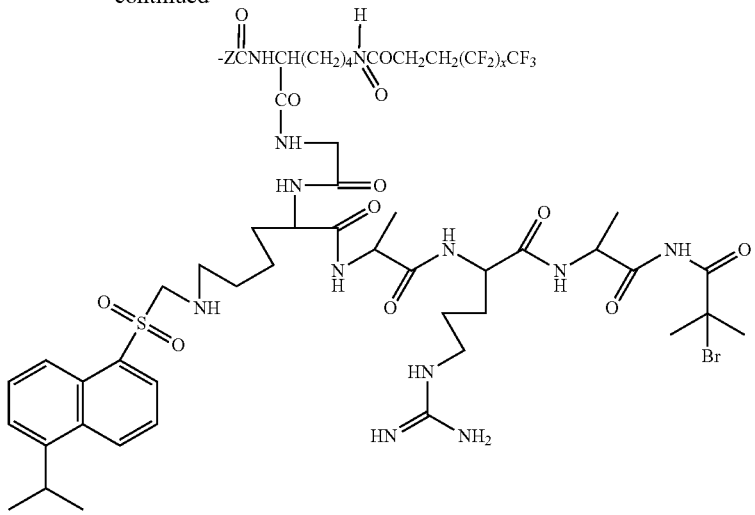

13

(BAL-LDI-p-RGD-Br)$_2$—PTMO is an example of BFSM with two glycine-lysine (dansyl labeled)-glycine-arginine-glycine-aspartic acid peptide sequences. It can provide specific binding affinity and function to select cells migrating on the biomaterial surface. In addition, it can contribute to enhancing the biocompatible surface characteristic of the polymer to which it is added, by interfacing with the biological environment and specifically controlling and permitting the integration of cells with an implant, and more specifically, tissue engineering implant devices. As shown in the structure (compound 12), there is an amide end group within the structure unit D. RBMI was synthesized by reacting BIBB with this amide groups. The conditions of synthesis for this reaction are as follows.

0.156 g of the previously dried (compound 12) (0.012 mmol OCNH$_2$) and 0.013 mL (0.015 mmol) of TEA were dissolved in 10 mL of anhydrous CH$_2$Cl$_2$ under a nitrogen atmosphere. The solution was cooled in an ice-water bath. 0.011 mL (0.0134 mmol) of BIBB was added dropwise to the (compound 12)/CH$_2$Cl$_2$ solution under a nitrogen atmosphere. The mixture was stirred for 20 hours at room temperature and was filtered to remove the TEA-HBr salt. The filtrate was washed with 1 mL of water three times and dried. The CH$_2$Cl$_2$ was evaporated at room temperature. A pale yellow solid RBMI (compound 13) was obtained and dried under vacuum at 40° C. overnight. Theoretical elemental content: C, 42.75%; H, 5.52%; N, 2.39%; S, 2.39%; F, 19.29%; O, 16.42%; Br, 13.64%. $^1$HNMR (300 MHz, CDCl$_3$) δ (ppm) 7.93 (br. ArH$_6$), 4.38 (m, COOCH$_2$CH$_2$CF$_2$), 4.05 (m, NCHCO), 3.65 (s, C$_{PU}$OOCH$_2$), 3.42 (s, C$_{PU}$H$_2$OCH$_2$), 3.15 (m, NCH$_2$C), 2.90 (s, ArCH), 2.46 (Br, CF$_2$CH$_2$), 2.05 (s, C(CH$_3$)$_2$Br), 1.60 (s, CH$_2$CH$_2$CH$_2$), 1.24-1.12 (m, ArCCH$_3$, NCCH$_3$). Based on the integration values at 7.93 and 2.05 ppm, the Br containing group conjugation efficiency was calculated to be 45.3%. It is believed that this lower conversion was partially related to the lower reactivity of the amide groups.

Soft Segment Change within Macroinitiators

| Example No. | Compound ID | Description |
|---|---|---|
| 8 | (Compound 14) | (BAL-LDI(COOH))$_2$-(THDI-DPS) |
|   | (Compound 15) | (BAL-LDI-p-TCAA)$_2$-(THDI-DPS) |
| 9 | (Compound 16) | (BAL-LDI(COOH))$_2$-PMSA |
|   | (Compound 17) | (BAL-LDI-p-TCAA)$_2$-PMSA |
| 10 | (Compound 18) | (BAL-LDI(COOH))$_2$-PEB |
|   | (Compound 19) | (BAL-LDI-p-TCAA)$_2$-PEB |
| 11 | (Compound 20) | (BAL-LDI(COOH))$_2$-PHE |
|   | (Compound 21) | (BAL-LDI-p-TCAA)$_2$-PHE |

In this section a variety of compounds differing in soft segment chemistry are synthesized. The purpose of implementing such a strategy was to establish the versatility of the technology.

EXAMPLE 8: Synthesis pf tCMI by coupling TCAA to α,ω-BAL-poly(LDI/THDI/DPS) pendent carboxylic acid precursor (COMPOUND 15).
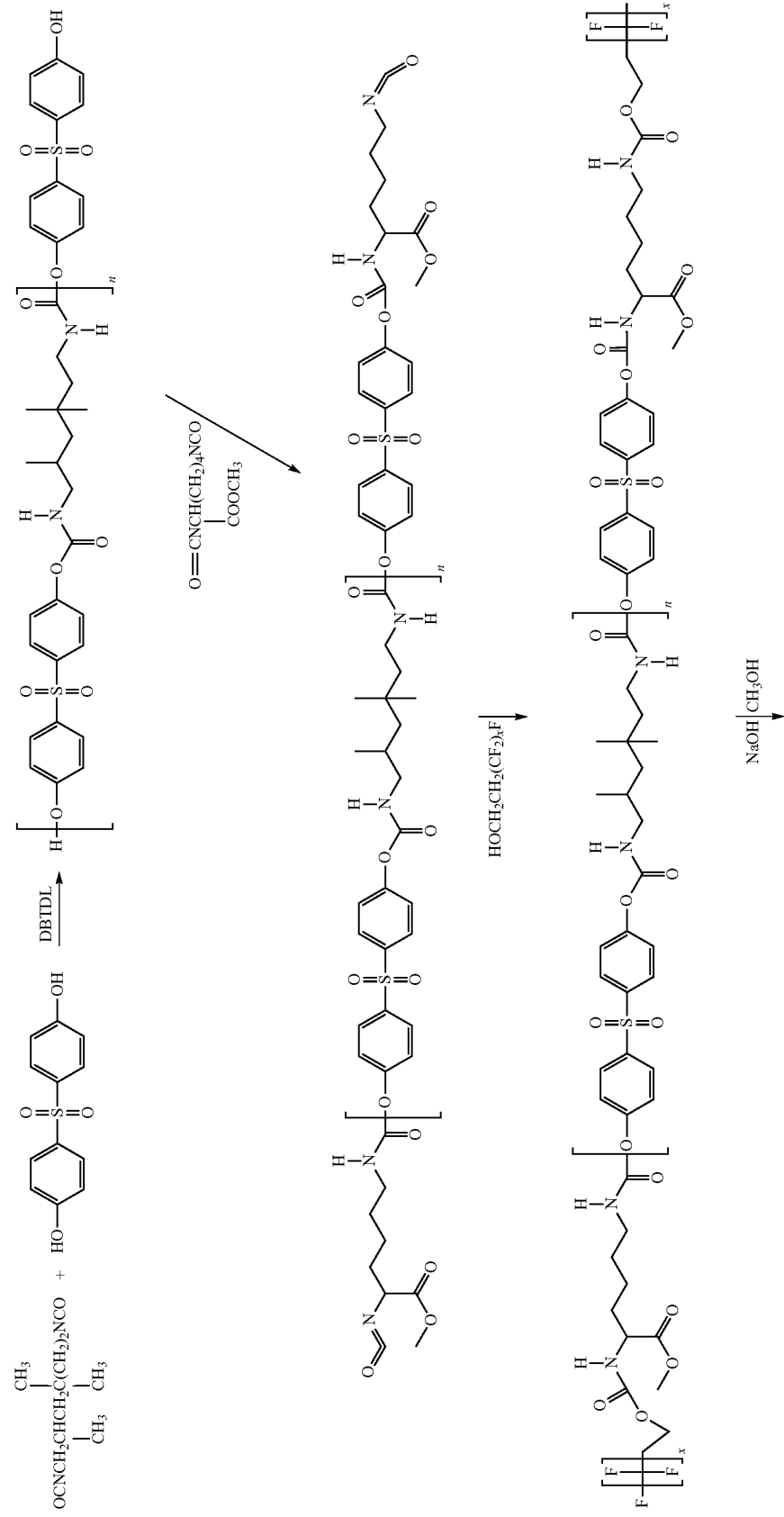

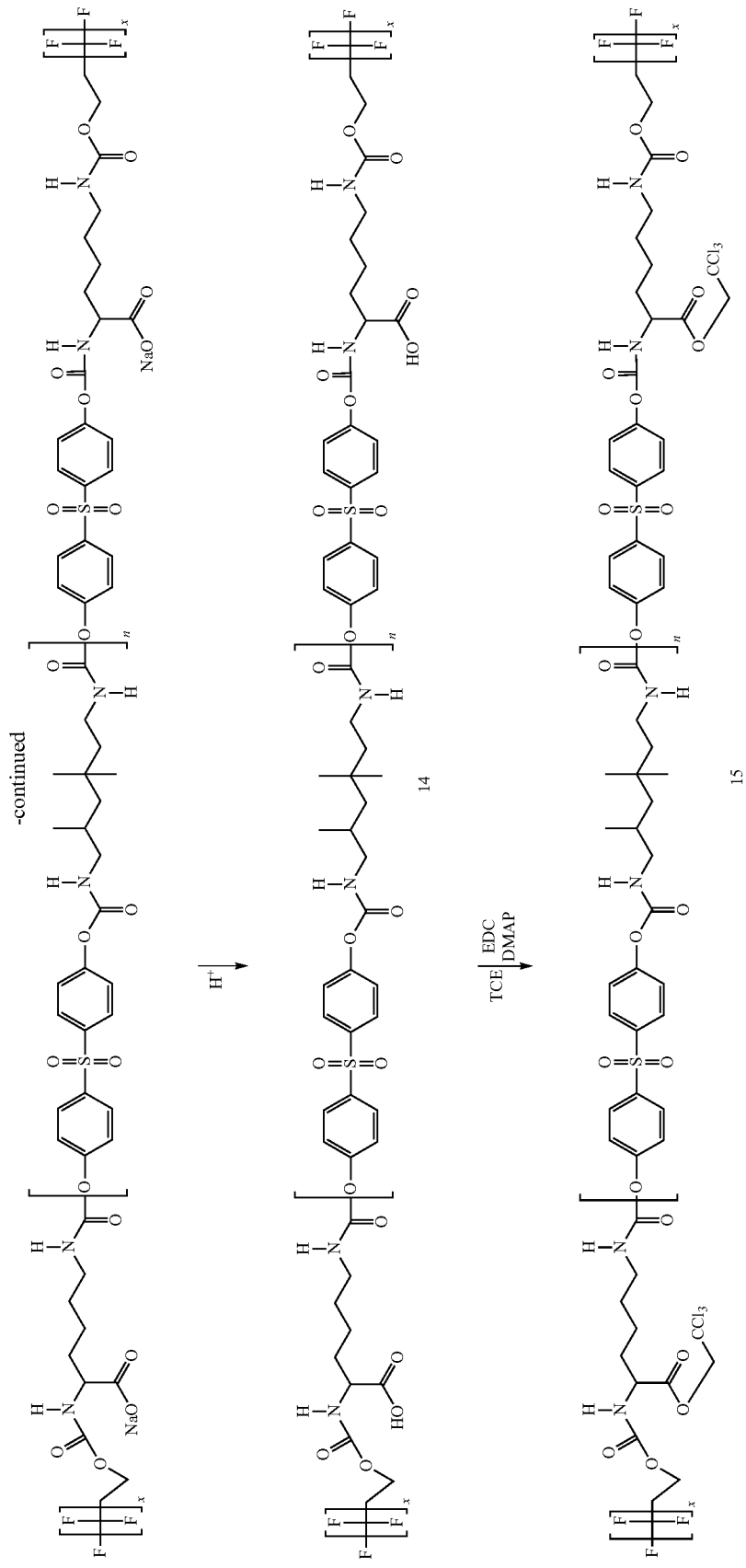

To a glass bottle equipped with a thermometer and a magnetic stir bar, freshly dried DPS (15.323 g, 60 mmol) in 70 mL of anhydrous DMAc was added under a nitrogen atmosphere. This reaction mixture was heated to 60° C. THDI (10.514 g, 50 mmol) was added and an additional of 10 mL DMAc was used to wash all the THDI in the container and was added into the reactor. DBTDL (0.05 mL) was used as the catalyst, and the reaction mixture was allowed to stir for 3 hours at 60-65° C. To this reaction mixture was added LDI (4.245 g, 20 mmol) and the reaction mixture was stirred for 3 hours. BAL (9.746 g, 22 mmol) and 0.02 µL of DBTDL were added to the reactor and allowed to stir overnight. The final product was precipitated in water, and further washed with water three times and dried under vacuum. Acidification of the protective methyl ester group pendent on the LDI units was carried out under the same conditions as the acidification of (BAL-LDI)$_2$—PTMO precursor. Halogenation: 5 g (0.99237 mmol of COOH) of (compound 14), EDC and DMAP (in a 1:1.5:0.5 molar ratio of acid groups:EDC:DMAP) were dissolved in 200 mL of anhydrous CH$_2$Cl$_2$. TCE (6 molar ratio to the acid groups) was added to the reaction flask. This solution was reacted under a nitrogen atmosphere for 1 week at room temperature. The CH$_2$Cl$_2$ solvent was evaporated at room temperature. The solid mixture was washed with deionized water three times and then extracted into diethyl ether. Removing diethyl ether by rotary-evaporation yielded a viscous liquid. The viscous liquid was washed with hexane three times to remove free TCE, and dried under vacuum at 40° C. overnight to yield (compound 15). Elemental analysis: C, theoretical 40.0%; measured 44.2%; H, theoretical 3.2%; measured 4.8%; Cl, theoretical 9.1%; measured 5.0%; F, theoretical 29.0%; measured 23.0%; N, theoretical 3.6%; measured 5.3%; O, theoretical 12.3%; measured 5.7%; S, theoretical 2.7%; measured 12.8%. $^1$H NMR (300 MHz, CDCl$_3$) δ (ppm) 7.98-6.88 (m, ArH), 5.37-4.78 (m, NH, OCH$_2$CCl$_3$), 4.37 (m, OCH$_2$CH$_2$CF$_2$ and NCHC=O), 3.67 (m, CH$_2$NH), 3.19 (m, CH$_2$NH), 2.46 (m, OCH$_2$CH$_2$CF$_2$), 1.95-1.16 (m, C$_{PU}$H$_2$CH$_2$CH$_2$, C$_{PU}$H$_2$CH(CH$_3$)CH$_2$), 1.00-0.80 (m, C$_{PU}$H$_2$CH(CH$_3$)CH$_2$). Both NMR and elemental analysis indicated successful incorporation of the active chlorine site in the macroinitiator molecule.

25 g (10 mmol) of freshly dried PMSA (amine number 0.6-0.8 meq/g) was dissolved in anhydrous THF (80 mL) in a sealed glass bottle (equipped with a thermometer and a magnetic stir bar) in a cold water bath. 4.245 g (20 mmol) of LDI was added with vigorous stirring and 5 mL of anhydrous THF was used to wash all LDI in the container and was added into the reactor. This solution was stirred at room temperature for 2 hours. BAL (9.30 g, 21 mmol) and 60 µL of DBTDL were added to the reactor, and stirred at 45° C. overnight. The product was precipitated in water, washed three times in water, and dried under vacuum. Hydrolyzation: in a glass beaker, a methanol/THF (1/1 in v/v) mixture was added to the precursor (~0.125 g/mL) and stirred until it became a suspension solution. 1 N aqueous NaOH was added to the precursor/methano/THF solution (0.9 mL/g for NaOH/precursor). This reaction mixture was stirred at room temperature for 18 hours. All solvents were removed under vacuum at room temperature. Acidification: the solid hydrolyzed product was re-dissolved in a methanol/water (20/80 in v/v) mixture and acidified by adding 10% aqueous citric acid as 0.45 fold of aqueous NaOH (or 1 N HCl acid as the same volume of aqueous NaOH). The precipitated solid product was washed in water and neutralized (the removal of Cl$^-$ anions was tested by adding AgNO$_3$ to the solution and checked for AgCl precipitation). The acidified product (compound 16) was dried under vacuum at 60° C. for 72 hours. The excess BAL was removed by methanol in this step. Acidity determination: (compound 16) (0.3 g) was dissolved in 10 mL of a toluene/acetone (2/1 in v/v) solvent mixture. To this solution was added two drops of phenolphthalein as an indicator and the solution was titrated with 0.025 N NaOH/methanol. This solution was calibrated by a commercial aqueous HCl standard. Halogenation: 3 g of (compound 16), EDC and DMAP (in a 1:1.5:0:5 molar ratio of acid groups:EDC:DMAP) were dissolved in 50 mL of anhydrous CH$_2$Cl$_2$. TCE (6 molar ratio to the acid group) was added to the reaction flask. This solu- EXAMPLE 9: Synthesis of tCMI by coupling TCE to α,ω-BAL-poly(LDI/PMSA) pendent carboxylic acid precursor (COMPOUND 17).

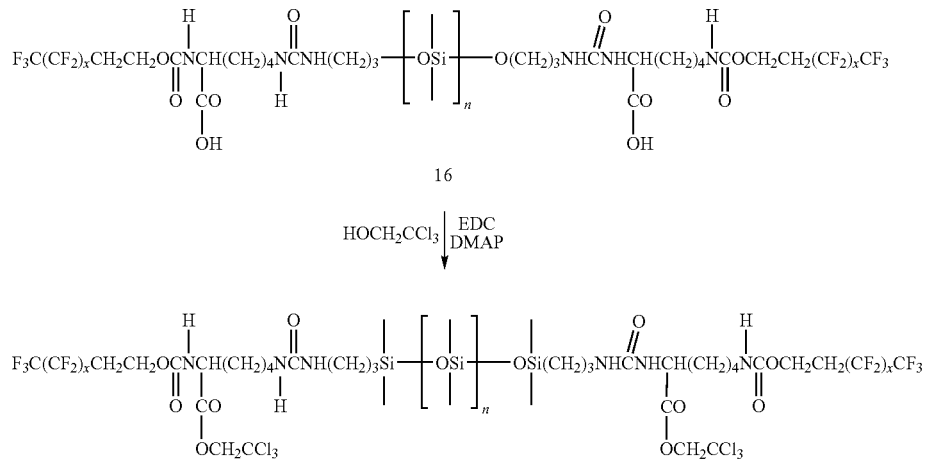

tion was reacted under a nitrogen atmosphere for 1 week at room temperature. The $CH_2Cl_2$ solvent was evaporated at room temperature. The solid mixture was washed with de-ionized water three times and then extracted into diethyl ether. Removing diethyl ether by rotary evaporation yielded a viscous liquid. The viscous liquid was washed with hexane three times to remove free TCE, and dried under vacuum at 40° C. overnight to yield (compound 17). Elemental analysis of (compound 17): C, theoretical 32.63%; measured 33.55%; H, theoretical 5.97%; measured 4.94%; Cl, theoretical 6.13%; measured 3.35%; F, theoretical 16.31%; measured 34.12%; N, theoretical 2.03%; measured 3.24%; O, theoretical 15.98%; measured 8.10%; Si, theoretical 21.96%; measured 12.90%. $^1$H NMR (300 MHz, $CDCl_3$) δ (ppm) 5.37 (s, NH), 4.68 (m, NH, $OCH_2CCl_3$), 4.37 (m, $OCH_2CH_2CF_2$ and NCHC=O), 3.64 (m, $OCH_2CH_2CH_2NH$), 3.19 (m, $CH_2NH$), 2.46 (m, $OCH_2CH_2CF_2$), 1.95-1.16 (m, $C_{PU}H_2CH_2CH_2$), 0.45 (m, —$Si(CH_3)_2$—$CH_2$), 0.0 (s, —$Si(CH_3)_2$—$CH_2$). The incorporation of the active chlorine initiator site was shown by the NMR and the elemental analysis data.

mixture and stirred at room temperature for 48 hours. Acidification: a 10% excess of aqueous 1 N HCl or 10% aqueous citric acid (relative to the amount of NaOH added in the previous step) was added and stirred for 1 hour. The acidified precursor (compound 18) was precipitated in water and washed in water to neutralize it, or washed to remove chloride anions in the solution. The latter was verified by observing no white precipitation of AgCl when adding aqueous $AgNO_3$ into the solution. (Compound 18) was dried under vacuum at 60° C. for 24 hours. The excess BAL was removed by methanol. Acidity determination: acidified (compound 18) (0.3 g) was dissolved in 10 ml of a toluene/acetone (2:1 in v/v) mixture, and 2 drops of phenolphthalein as an indicator was added. The mixture was titrated using a 0.025 N NaOH/methanol solution which was calibrated by a commercial aqueous HCl standard. Based on this data, the coupling of TCE to the precursor was carried out. Coupling: (compound 18) (3 g), EDC and DMAP (in a 1:1.5:0.5 molar ratio of acid groups:EDC:DMAP) were dissolved in a 100 ml mixture of equal amount of anhydrous toluene and $CH_2Cl_2$. TCE (6 molar ratio to the acid groups) was added to the reaction flask.

EXAMPLE 10: Synthesis of tCMI by coupling TCE to α,ω-BAL-Poly(LDI/PEB) pendent carboxylic acid (COMPOUND 19).

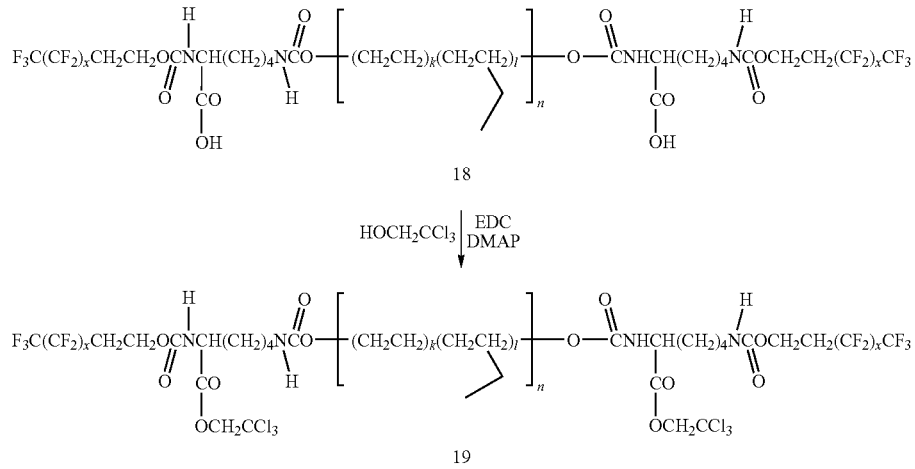

Freshly dried PEB (25 g, 10 mmol) was dissolved in toluene (175 mL) in a glass bottle (equipped with a thermometer and a magnetic stir bar) at 70° C. LDI (4.245 g, 20 mmol) was added with vigorous stirring. Toluene (5 ml) was used to wash all LDI in the container and was added into the reactor. DBTDL (0.1 ml) was added to the reaction mixture and the solution was stirred at 70° C. for 3 hours. BAL (9.30 g, 21 mmol) in toluene (25 mL) was added to the reaction mixture and stirred at 70° C. overnight. The product was precipitated in water, washed three times in water, and dried under vacuum. Hydrolyzation: in a glass beaker, 38 g of precursor was dissolved in toluene (200 mL) at 70° C. and cooled to room temperature. Methanol (75 ml) was added to the reaction mixture and stirred fully to become a suspension solution. Aqueous NaOH (21 ml-1 N) was added to the reaction This solution was reacted under a nitrogen atmosphere for 1 week at room temperature. The reaction mixture was precipitated in 800 mL of MeOH and dried under vacuum at 40° C. overnight to yield (compound 19). Elemental analysis of (compound 19): C, theoretical 65.51%; measured 73.42%; H, theoretical 9.94%; measured 13.66%; Cl, theoretical 2.88%; measured 2.23%; F, theoretical 15.33%; measured 8.58%; N, theoretical 1.43%; measured 1.32%; O, theoretical 0.49%; measured 1.01%. $^1$H NMR (300 MHz, $CDCl_3$) δ (ppm) 5.26 (m, NH), 4.72 (m, NH), 4.67 (dd, $OCH_2CCl_3$), 4.41 (m, $OCH_2CH_2CF_2$ and NCHC=O), 4.01 (m, $OC_{ET}H_2CH_2$, $CH_2C_{BT}RO$), 3.19 (s, $CH_2NH$), 2.46 (m, $OCH_2CH_2CF_2$), 1.95-0.70 (m, $C_{PU}H_2CH_2CH_2$, $C_{PU}H_2CH(CH_2CH_3)CH_2$, $C_{PU}H_2CH(CH_2CH_3)CH_2$ $C_{PU}H_2CH(CH_2CH_3)CH_2$). The incorporation of the active chlorine initiator site was shown by the NMR and the elemental analysis data.

EXAMPLE 11: Synthesis of tCMI by coupling TCE to α,ω-BAL-Poly(LDI/PHE) pendent carboxylic acid (COMPOUND 21).

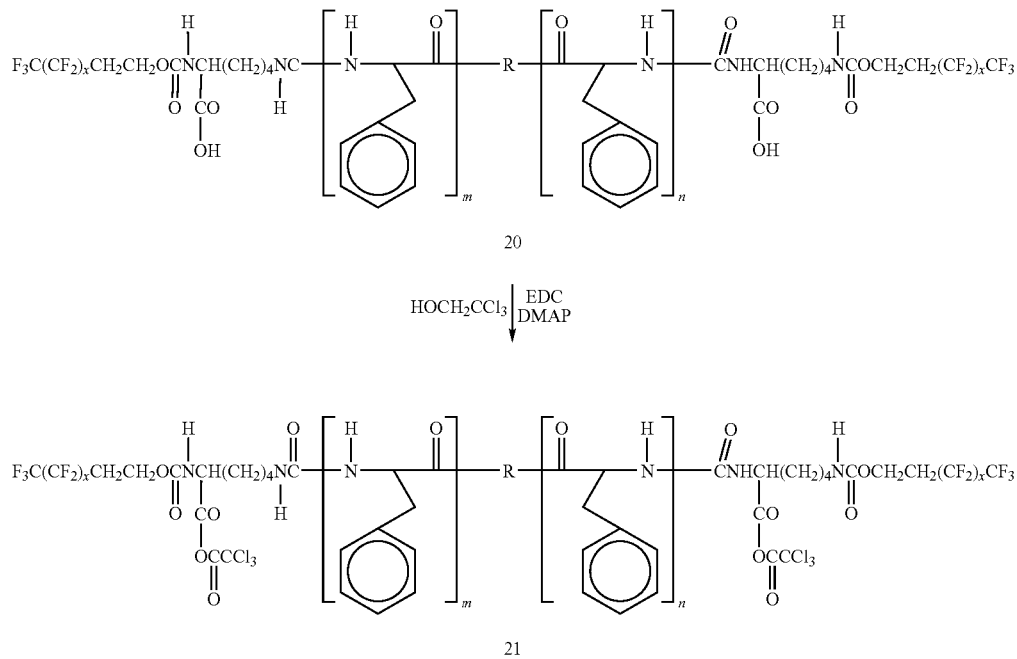

The poly(LDI/PHE) precursor (compound 20) was synthesized with lysine diisocyanate. Amino acids can be used in monomer or peptide form, and coupled to triethylene glycol or diamine or diol (ethylene glycol, butane diol, hexane diol, hexane diamine, cyclohexane diol, etc.) or ester or amide containing oligo-amino-acid compounds (consisting of the form amino-acid:TEG:amino-acid or peptide:TEG:amino-acid, or peptide:TEG:peptide) with terminal amines that can react with an diisocyanate in order to make a precursor. In this example, the oligomer is a di-PHE oligomer coupled with LDI and terminated with fluoroalcohol.

In a nitrogen atmosphere, a solution of PHE (2.223 g, 5 mmol) in 30 ml of anhydrous DMAc was added dropwise into the solution of LDI (2.122 g, 10 mmol) in 30 ml of anhydrous DMAc cooled with an ice-water bath. After reacting at room temperature for two hours, BAL (4.9 g) and DBTDL (30 µL) were added to the reaction, and the mixture was reacted between 60-70° C. overnight. The product was precipitated in distilled water and did not need to be dried. Acidification of the methyl ester of the LDI unit was carried out by mild hydrolysis of the protective ester group by dissolving the un-dried precursor in methanol, stirred with 10.5 ml of 1.0 N NaOH aqueous, at room temperature for 18 hours. The hydrolysis product was acidified and precipitated by adding 10% aqueous citric acid or 1 N HCl acid stoichiometrically to the amount of NaOH used. The solid product (compound 20) was washed in water until the pH was 6~6.5, when citric acid was used. When 1 N HCl was used in the acidification step, the product was washed until no Cl⁻ anion was detected in the solution, which can be checked by observing no white precipitation of AgCl when adding AgNO₃ aqueous into the washed solution. (Compound 20) was dried under vacuum at 60° C. for 48 hours. Coupling of TCE: (Compound 20) (5 g, 5.8922 mmol of COOH group), EDC and DMAP (in a 1:8:0.5 molar ratio of acid groups:EDC:DMAP) were dissolved in 200 ml of anhydrous $CH_2Cl_2$. TCE (1.1 molar ratio to the acid group) was added to the reaction flask. This solution was reacted under nitrogen protection for 1 week at room temperature. The $CH_2Cl_2$ solvent was evaporated at room temperature. The solid mixture was extracted by diethyl ether and was precipitated in water. Removing ether from the organic phase by rotary evaporator yielded a viscous liquid. The viscous liquid was dried under vacuum at 40° C. overnight to yield (compound 21).

ATRP Grafted Polymers

| Example No. | Compound ID | Description |
|---|---|---|
| 12 | (Compound 22) | (BAL-LDI-p-Tris-PVP-Br)₂-PTMO |
| 13 | (Compound 23) | (BAL-LDI-p-Tris-PHEMA-Br)₂-PTMO |
| 14 | (Compound 24) | (BAL-LDI-p-RGD-PHEMA-Br)₂-PTMO |
| 15 | (Compound 25) | (BAL-LDI-p-Tris-PtBMA-Br)₂-PTMO |
|    | (Compound 26) | (BAL-LDI-p-Tris-PMAA-Br)₂-PTMO |
|    | (Compound 27) | (BAL-LDI-p-Tris-PNaMA)-Br)₂-PTMO |
| 16 | (Compound 28) | (BAL-HDI-DABS-p-PMMA)₂-PTMO |
| 17 | (Compound 29) | (BAL-LDI-p-AEE-PDPAMA-Br)₂-PTMO |
| 18 | (Compound 30) | (BAL-LDI-p-AEE-PMPC-Br)₂-PTMO |
| 19 | (Compound 31) | (BAL-LDI-p-AEE-PAAm-Br)₂ |

In this section a series of alkyl halide macro initiators are polymerized in a controlled manner (targeted molecular weights and MWDs<1.8), using the ATRP polymerization technique. The synthetic pathways are demonstrated for a selected range of monomers. The same reaction mechanism can be used to polymerize other monomers.

EXAMPLE 12: Polymerization of vinyl pyrrolidone initiated by tBMI (COMPOUND 22).

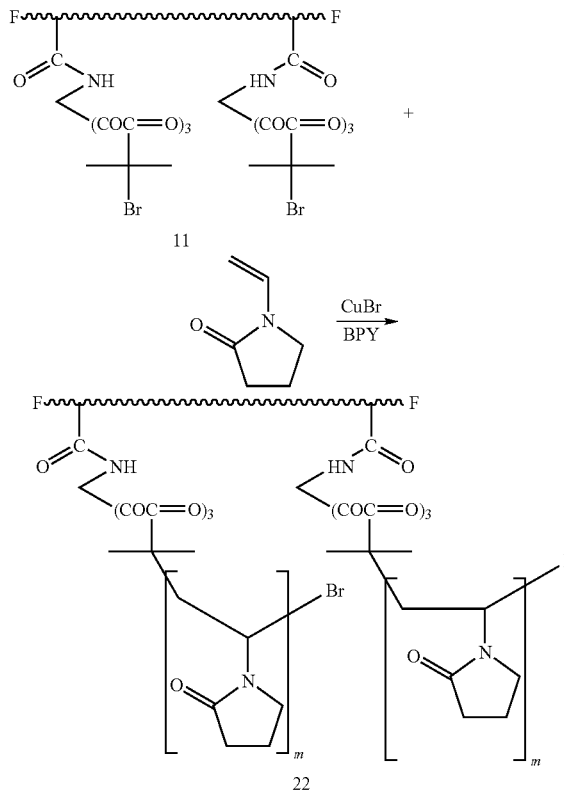

This material has the ability to generate a non-ionic hydrophilic polymer with the ability to retain water at the polymer interface. In combination with a polyanionic surface modifying group, a base polymer with low friction (i.e. good lubricity) properties could be processed. As well, polyvinyl pyrrolidone has been shown to endow non-protein fouling characteristics onto polymers. The atom transfer radical polymerization (ATRP) or "living" radical polymerization technique[3] was used to construct the final product.

A typical procedure was as follows: 3.33 g (30 mmol) of VP, 0.143 g (1 mmol) of CuBr, and 1 mmol of tBMI (compound 11) were added to a flask. The flask was sealed with a rubber septum and cooled in ice water. The mixture was bubbled with ultrahigh-purity nitrogen for 30 minutes. BPY (0.156 g, 1 mmol), previously purged with ultrahigh-purity nitrogen, was added under nitrogen. The flask was heated in an oil bath to 100° C. for 20 hours. The polymerization was stopped by cooling the flask in ice water. The solution was diluted with 200 mL of $CH_2Cl_2$ and filtered through an alumina column to remove the catalyst. After evaporating the $CH_2Cl_2$ from the filtrate at room temperature, the solid product (compound 22) was dried under vacuum at 40° C. overnight. Elemental analysis: C, calculated 63.79%; measured 59.66%; H, calculated 8.04%; measured 9.41%; N, calculated 12.12%; measured 11.56%; O, calculated 14.49%; measured 16.89%; F, calculated 0.92%; measured 0.67%; Br, calculated 0.65%; measured 1.10%. Based on F and Br content, the VP conversion reached 78.6%; translating to an average degree of polymerization for the PVP branch of 60. $^1$H NMR (300 MHz, $CDCl_3$) δ (ppm) 7.00 (d, $C_{PVP}H_2CH$), 4.92 (m, $C_{PVP}H_2CH$), 3.48 (t, $N_{PVP}CH_2$), 3.40 (s, $C_{PU}H_2OCH_2$), 2.47 (t, $C_{PVP}OCH_2$), 2.10 (m, $C_{PVP}H_2CH_2CH_2$), 1.62 (s, $C_{PU}H_2CH_2CH_2CH_2$).

EXAMPLE 13: Polymerization of hydroxyethyl methacrylate initiated by using a choice of initaitors from examples 1-6 (COMPOUND 23).

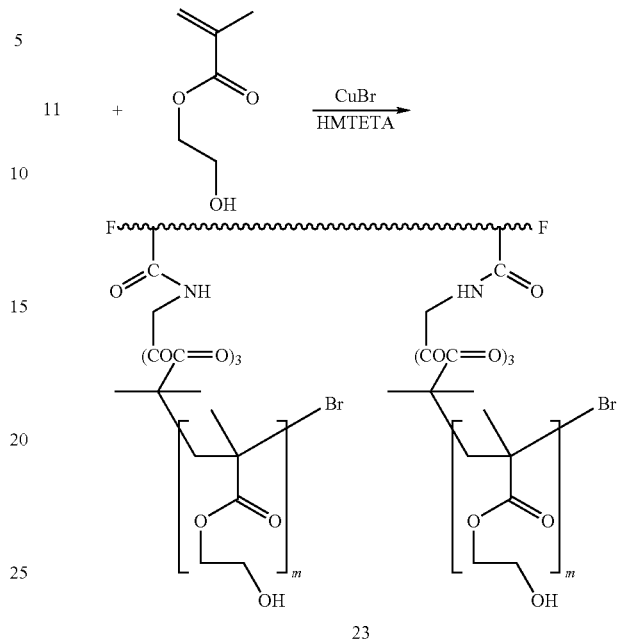

Polyhydroxyethyl methacrylate repeat units provide a unique scaffolding with multifunctional sites for covalent and non-covalent attachment of pharmaceutically active compounds or other potent moieties. In addition, this polymer has hydrating properties which may be used to render surfaces more lubricious.

1 mmol of initiator (tBMI (compound 11)) was dissolved in 10 mL of DMF in a flask equipped with a stir bar. 0.143 g (1 mmol) of CuBr and 0.253 g (1.1 mmol) of HMTETA were added into the solution. The flask was connected to a vacuum line and was freeze-thawed three times by liquid nitrogen. This flask was filled with ultrahigh-purity nitrogen and 2.86 g (22 mmol) of freshly distilled HEMA was added. The flask was heated in an oil bath to 50° C. for 20 hours. The polymerization was stopped by cooling the flask in ice water. DMF was evaporated from the solution at 40° C. The viscous solid was dissolved in THF and filtered through a silica gel column to remove the catalyst. After evaporating THF from the filtrate at room temperature, the solid product (compound 23) was dried under vacuum at 40° C. overnight. Theoretical elemental analysis best estimates based on the structure of the starting precursor materials are given here for comparison purposes. Elemental analysis: C, theoretical 53.20%; measured 53.50%; H, theoretical 7.36%; measured 7.54%; N, theoretical 0.41%; measured 2.56%; O, theoretical 33.37%; measured 25.91%; F, theoretical 3.31%; measured 10.21%; Br, theoretical 2.34%; measured 0.28%. $^1$H NMR (300 MHz, DMSO) δ (ppm) 4.80 (s, $C_{PHEMA}H_2OH$), 3.92 (s, $C_{PHEMA}OOCH_2$), 3.60 (s, $C_{PHEMA}H_2OH$), 1.79 (s, $C_{PHEMA}H_2CCH_3$), 0.80 (s, $C_{PHEMA}H_2CCH_3$). The average (polystyrene equivalent) molecular weight was recorded as $9.01 \cdot 10^4$ g/mol with polydispersity of 1.65. The weight average MW of the final product was substantially larger than (compound 11) (example 6). This data indicated a successful polymerization of the final product. Based on OH titration, the average degree of polymerization can be determined for the PHEMA portion of the molecule. The theoretical OH number was 6.366 mmol/g, and the titrated value was 6.386 mmol/g. Based on the OH number, the HEMA was quantitatively incorporated and the average degree of polymerization for the PHEMA branch was 21.7.

EXAMPLE 14: Polymerization of hydroxyethyl methacrylate initiated by RBMI (COMPOUND 24).
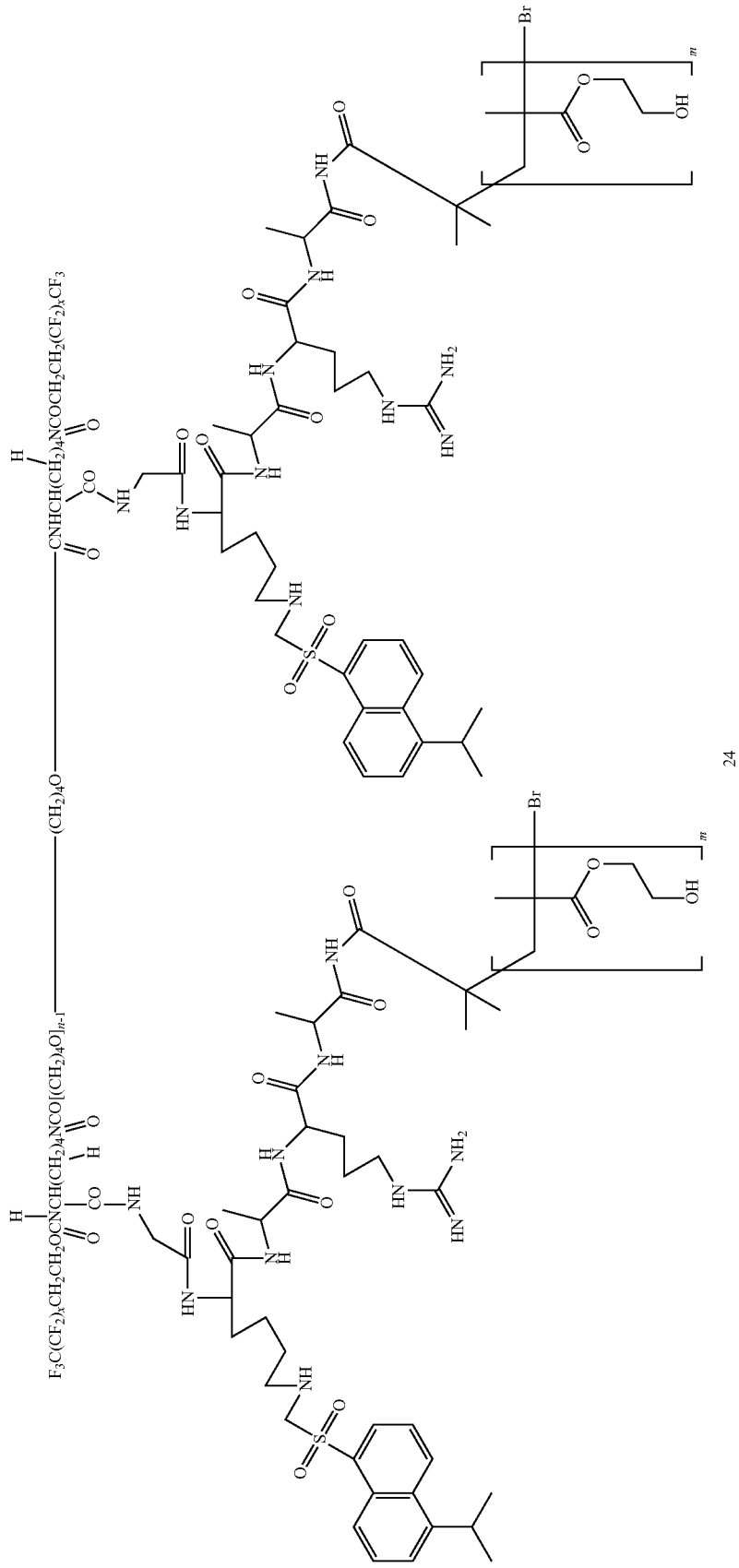

This example is similar to example 13 except that it shows the synthesis of the polyhydroxy methacrylate pendent chain with a different macro-initiator molecule.

0.0072 g (0.05 mmol) of CuBr, 0.05 mmol Br group of RBMI (compound 13), 0.021 mL (0.10 mmol) of PMDETA and 1.5 mL of DMF were added to a flask. The flask was sealed with a rubber septum and cooled in ice water. The mixture was bubbled with ultrahigh-purity nitrogen for 20 minutes. 0.063 mL (5 mmol) of HEMA in 1 mL of DMF (purged with ultrahigh-purity nitrogen) was added to the reaction mixture, under a nitrogen atmosphere. The flask was heated in an oil bath to 100° C. for 30 min then stirred at 80° C. for 20 hours. The polymerization was stopped by cooling the flask in ice water. The solution was diluted with 5 mL of $CH_2Cl_2$ and filtered through a silica gel column to remove catalyst. After evaporating the water from the filtrate at room temperature, the solid product (compound 24) was dried under vacuum at 40° C. overnight. $^1H$ NMR (300 MHz, $CDCl_3$) data on the product are reported as follows: δ (ppm) 4.38 (m, $COOCH_2CH_2CF_2$), 4.30 (t, $C_{PHEMA}OOCH_2$), 4.05 (m, NCHCO), 3.86 (t, $C_{PHEMA}H_2OH$), 3.65 (s, $C_{PU}OOCH_2$), 3.42 (s, $C_{PU}H_2OCH_2$), 3.15 (m, $NCH_2C$), 2.90 (s, ArCH), 2.86 (s, OH), 2.46 (br, $CF_2CH_2$); 2.05 (s, $C_{PHEMA}CH_3Br$), 1.60 (s, $CH_2CH_2CH_2$), 1.55 (br, $C_{PHEMA}H_2CCH_3$), 1.24-1.12 (m, $ArCCH_3$,), 0.94-0.75 (br, $C_{RGD}H_3$, $C_{PHEMA}H_3$). Based on the integration values at 2.05 and 0.85 ppm and the Br functionality of RMI (0.453), the HEMA conversion was calculated to be 39.6% and the estimated average degree of polymerization for the PHEMA segment calculated was 7.9. The lower conversion of the initiator site for this initiator was most probably the result of the complex molecular structure of the peptide space. However, despite of a lower conversion result than what was achieved for example 13, where a simpler initiator molecule was used, the incorporation of a significant number of pendant hydroxyl groups associated with the HEMA moiety of example 14 affords the polymer of the current invention with important surface and drug coupling properties.

EXAMPLE 15: Synthesis of a,ω-BAL-poly(LDI/PTMO) pendent polyacrylic acid (COMPOUND 25-27).

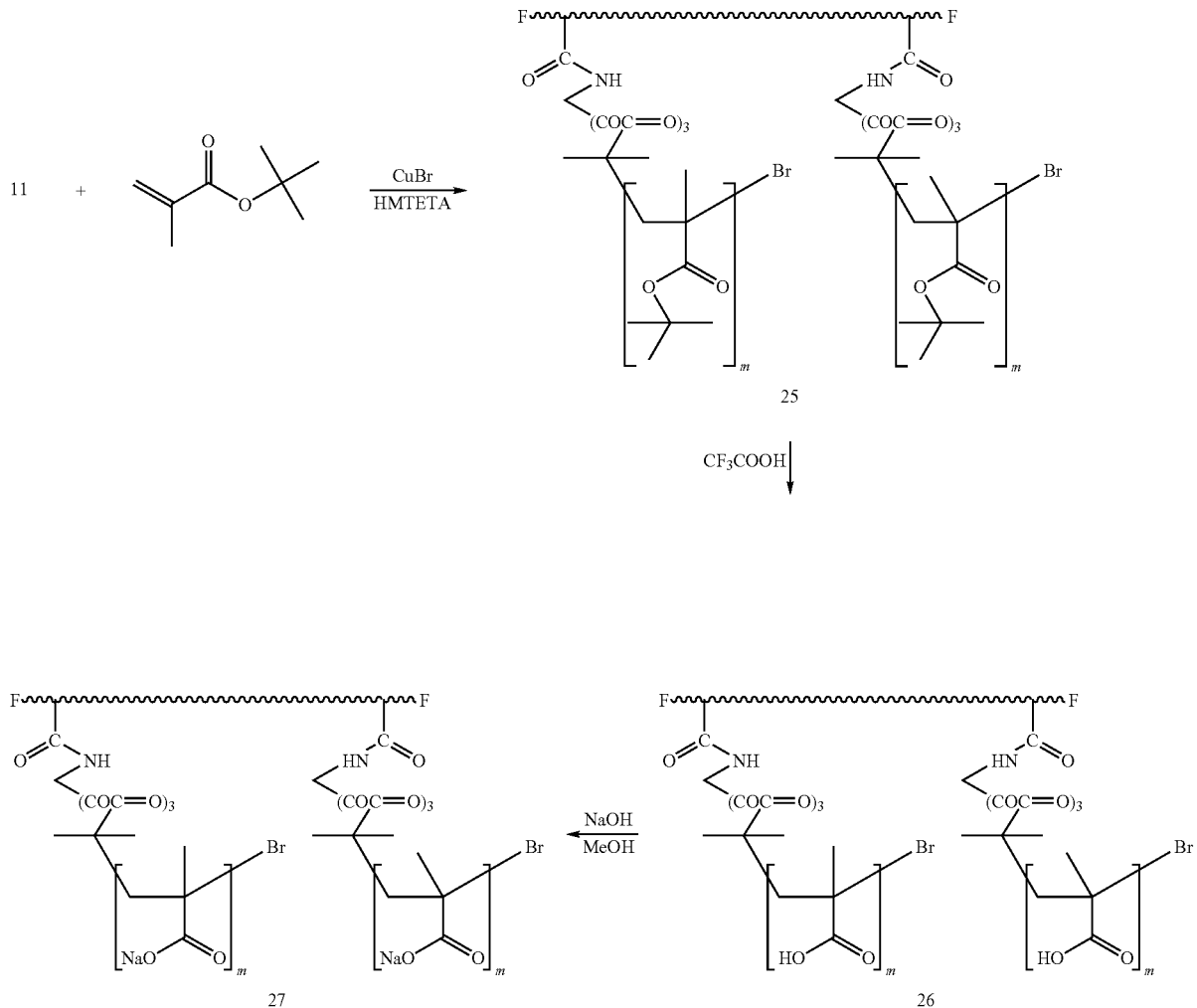

This example demonstrates the synthesis of a polyanionic system which can be used to couple drugs with different chemistries than those that could be coupled to polymers in examples 12 and 13. As well, this macro-ionic material provides excellent hydrating character for rendering polymers lubricious in nature. PAA and PMAA have been proven to be stimuli-responsive and biocompatible. The polyanionic chains tethered on the surface are self-assembled in an aqueous environment. The combination of the stimuli responsive character of the polyanions and the fluoro-oligo groups tethered on the surface of medical devices, makes the system more attractive as a drug delivery vehicle. The tethered PAA or PMAA pendent on (BAL-LDI)$_2$-PTMO can render the surface of a medical device useful for chemical separations, sensors and composite materials. For example, by controlling the molecular weight of the PAA or PMAA branches and adjusting the pH, it can be used as an immunosensor for antibody immobilization. The tethered PAA, PMAA or their soaps PNaA, PNaMA provide adhesion character and could significantly improve bonding to inorganic/polymer interfaces. The tethered polyacid and poly soap on the surface can also dramatically improve the water-absorbing properties and lubricity of biomaterials. The synthesis of (BAL-LDI-p-Tris-PMAA-Br)$_2$-PTMO (compound 26) and its soap (BAL-LDI-p-Tris-PNaMA-Br)$_2$-PTMO (compound 27) are described in this example. The processes for making (BAL-LDI-p-PAA)$_2$-PTMO and its soap (BAL-LDI-p-PNaA)$_2$-PTMO are identical. A macro-initiator, similar in nature to examples 1-6, can be used to carry out this polymerization.

A typical procedure was as follows: 2.1033 g (15 mmol) of tBMA, 0.149 g (1 mmol) of CuBr and 4 mL of xylene were added to a flask. The flask was sealed with a rubber septum and cooled in ice water. Ultrahigh-purity nitrogen was bubbled through the mixture for 15 minutes and then 0.461 g (2 mmol) of HMTETA previously purged with nitrogen was added by syringe. After the solution became clear and light green in colour, a solution of 0.5858 g (1 mmol of Br group) of TBMI (compound 11) in 5 mL of acetone previously purged with nitrogen was added. The flask was heated in an oil bath to 70° C. overnight. The polymerization was stopped by cooling the flask in ice water. The solution was diluted with 20 mL of THF and filtered through a silicon gel column to remove the catalyst. The filtrate was precipitated in water and the solid polymer (compound 25) was dried under vacuum at 30° C. overnight. 1 g of (compound 25) was dissolved into a solution of 9 mL of CHCl$_3$ and 1 mL of CF$_3$COOH. The solution was stirred at room temperature for 20 hours. The polymer became a gel-like semi solid in the solution. The solvent was removed by filtration and the solid was washed with CHCl$_3$ twice and filtered. All liquid residuals were removed under vacuum at room temperature. The solid product (compound 26) was dried under vacuum at 40° C. overnight. The number of COOH titrated was 8.8592 mmol/g which was 10.11 times higher than the COOH number of its precursor (compound 1). Based on titration results and the stoichiometry, the tBMA conversion was determined to be 96.7%, and the average degree of polymerization of the PMAA branch calculated was 14.6. (Compound 26) was then neutralized by using a NaOH/CH$_3$OH solution stoichiometrically to make a macrosoap. (Compound 26) (10 g, 88.592 mmol of COOH group) was dissolved in 200 mL of water and was added 88.60 mL of 1 N NaOH/methanol solution and stirred at room temperature (30 minutes). All solvents were evaporated at room temperature for 30 minutes. This yielded a colourless (BAL-LDI-p-Tris-PNaMA-Br)$_2$-PTMO soap (compound 27). The solid product was dried under vacuum at 40° C. for 24 hours. Elemental analysis: C, theoretical 43.92%; measured 44.78%; H, theoretical 4.93%; measured 6.49%; N, theoretical 0.74%; measured 0.77%; O, theoretical 25.50%; measured 31.22%; F, theoretical 6.00%; measured 3.56%; Br, theoretical 4.24%; measured 2.62%; Na, theoretical 14.65%; measured 12.81%. Based on the Na content, the average degree of polymerization for the PNaMA branch calculated was 13.25. The latter value agrees with the calculated degree of polymerization for the methacrylate units (i.e. 14.6) based on acid titration (see above).

EXAMPLE 16: Synthesis of α,ω-BAL-poly(HDI/DABS/PTMO) pendent poly(methyl methacrylate) (COMPOUND 28).

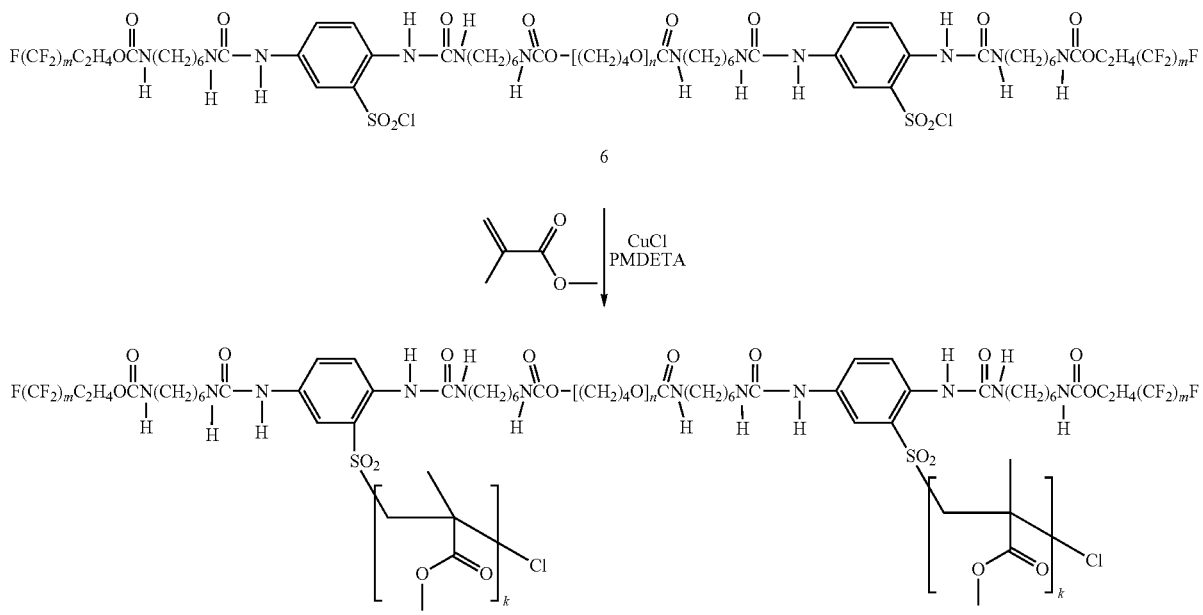

This example is similar to example 15 with the exception that it has been made with a different macro-initiator molecule.

CuCl (0.198 g, 2 mmol) was added to a solution of 3.016 g (2 mmol of $SO_2Cl$ group) (compound 7) in 50 mL of DMAc (see example 2) under a nitrogen atmosphere. This solution mixture was purged with ultrahigh-purity nitrogen for 15 minutes. PMDETA (0.520 g, 0.627 mL, 3 mmol) was added with a syringe. The solution in the reactor became green-brown in colour. The ultrahigh-purity nitrogen atmosphere was maintained for 10 minutes. MMA (2.002 g, 20 mmol) which was freshly distilled under a nitrogen atmosphere was added by syringe. The reaction was stirred at 90° C. for 20 minutes and then was stirred at 70° C. for 20 hours. After cooling to room temperature, the reaction solution was precipitated in water. The solid was re-dissolved in DMF and filtered through a silicon gel column to remove the catalyst. The filtered solution was precipitated in methanol. The final product (compound 28) was dried under vacuum at 50° C. overnight. Elemental analysis: C, theoretical 52.90%; measured 55.48%; H, theoretical 7.08%; measured 9.32%; N, theoretical 3.35%; measured 6.40%; O, theoretical 22.02%; measured 14.68%; F, theoretical 11.96%; measured 9.50%; Cl, theoretical 1.41%; measured 2.10%; S, theoretical 1.28%; measured 2.30%. $^1H$ NMR (300 MHz, DMSO) δ (ppm) 8.90-6.60 (m, ArH), 4.06 (s, $SO_2CH_2$), 3.91 (s, ArNH), 3.80-3.10 (m, $C_{PMMA}OOCH_3$, $C_{PU}H_2OCH_2$), 2.95 (t, $CH_2N$), 1.92 (s, $CH_3CCl$), 1.60 (br, $C_{PMMA}CH_2C$), 1.50 (s, $C_{PU}H_2CH_2CH_2$), 1.23 (br, $C_{PMMA}CH_3$), no vinyl signal was found at δ 5.5-6.0, indicating complete polymerization of the vinyl groups. Based on the assigned integration values at 1.86 to 0.30 ppm, contributions from $CH_2$ and $CCH_3$ of PMMA which were subtracted from the total proton contributions to isolate the theoretical contribution from the $CH_2$ of the SCl segment, the MMA monomer incorporation was estimated at 68%, with average degree of PMMA polymerization at 6.8.

EXAMPLE 17: Synthesis of α,ω-BAL-Poly(LDI/PTMO) pendent PDPAMA (COMPOUND 29).

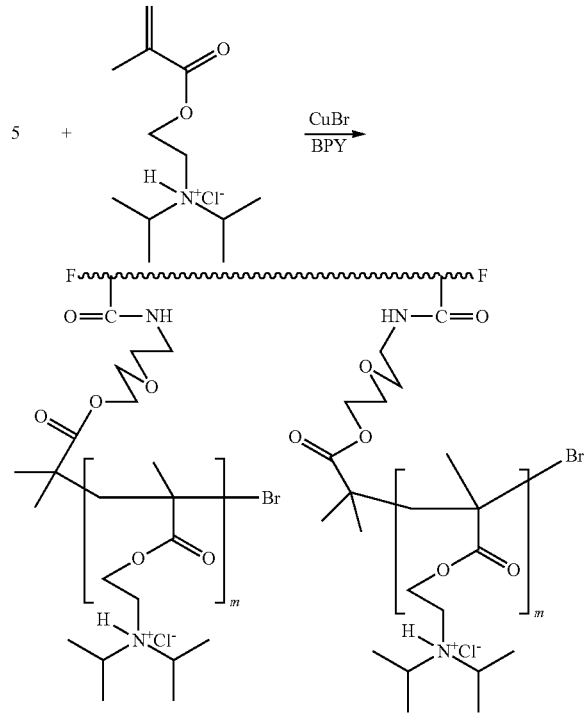

29

The solubility parameter of PDPAMA homopolymer is pH sensitive. SCMSM initiating ATRP of DPA results in a polymer consisting of $(BAL-LDI-p-AEE-PDPAMA-Br)_2$-PTMO. This material will provide biocompatible pH-responsive surface or interface to biomaterials and devices. Below pH 6, the domain PDPAMA chains act as a weak cationic polyelectrolyte and the surface or interface are highly hydrophilic, however above pH 6 the materials become hydrophobic due to deprotonation of its tertiary amine groups.

A solution of (compound 5) (2.8867 g, 2.00 mmol of Br) and BPY (0.625 g, 4.00 mmol) in methanol (30 mL) was prepared and purged with ultrahigh-purity nitrogen for 30 minutes. Following this, the CuBr catalyst (0.287 g, 2.00 mmol) was added to the mixture under a nitrogen atmosphere. The reaction mixture was stirred and purged with ultrahigh-purity nitrogen for 20 minutes. 4.688 mL (4.266 g, 20.0 mmol) of DPA (purged previously with ultrahigh-purity nitrogen) was added with a syringe to the reaction mixture under a nitrogen atmosphere. The reaction mixture was stirred at room temperature for 48 hours. Upon exposure to air, the reaction solution turned to blue from dark brown. The resulting polymer was diluted with DMF and passed through an alumina column to remove the catalyst. After evaporating all the DMF, the viscous solid was precipitated in hexane. The final product, (compound 29), was dried under vacuum at 50° C. for 24 hours. $^1H$ NMR (300 MHz, $CDCl_3$) was compared with (compound 5), and the following shifts were δ (ppm) 3.85 (m, $C_{PDPAMA}OOCH_2$), 2.99 (s, $N_{PDPAMA}CH_2$), 2.63 (S, $N_{PDPAMA}H$), 1.83 (br, $C_{PDPAMA}CH_2C$), 1.01 (s, $N_{PDPAMA}[C(CH_3)_2]_2$), 0.90 (br, $C_{PDPAMA}H_2CCH_{13}$), no residual vinyl signals were found at δ 5.5-6.5, indicating complete polymerization of the vinyl groups. Based on the integration values at 2.99 and 3.41 ppm (the $CH_2OCH_2$ of PU), the DPAMA monomer conversion was estimated to be 85.7%, thereby yielding an average degree of DPAMA polymerization at 8.6.

EXAMPLE 18: Synthesis of α,ω-BAL-Poly(LDI/PTMO) pendent PMPC (COMPOUND 30).

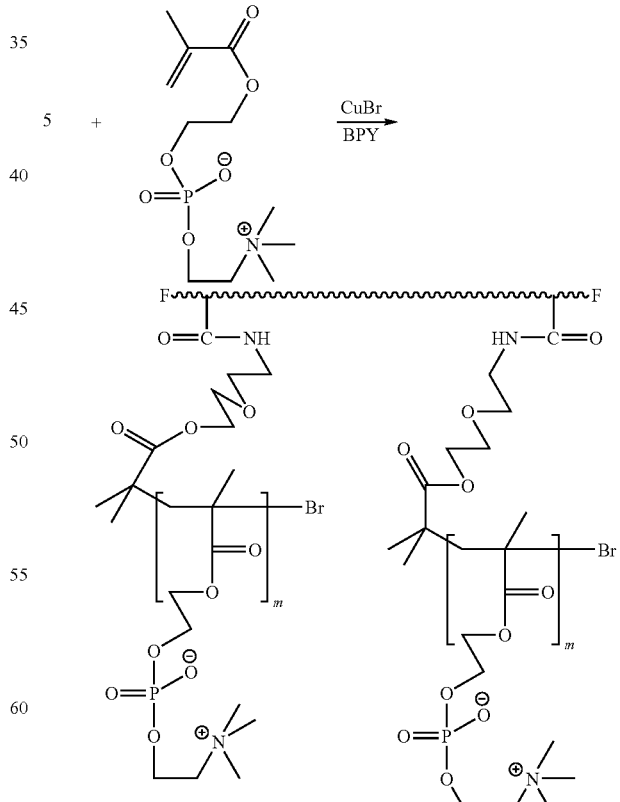

30

The phosphorylcholine motif is an important component of cell membranes. MPC is a so-called "bio-inspired" monomer. SCMSM initiated ATRP of MPC generated a polymer (α,ω-BAL-PU) with pendent PMPC chains, containing a high fluorine content and pendent oligo-phospholipid chains adjacent to the fluorine tails of SCMSM, such that the molecule can control cell/cell phospholipid membranes interactions to provide highly biocompatible material surfaces, with the potential to yield implant devices that reduce blood cell activation, are resistant to protein denaturation, and bacterial/cellular adhesion.

BMI (compound 5) (2.8867 g, 2.00 mmol of Br) was dissolved in methanol (40 mL). After purging with ultrahigh-purity nitrogen for 30 minutes, the CuBr catalyst (0.287 g, 2.00 mmol) and BPY (0.625 g, 4.00 mmol) were added to the stirred solution under a nitrogen atmosphere. MPC (5.94 g, 20.0 mmol) was then added as a solid to the reaction mixture under nitrogen. The reaction mixture was stirred at room-temperature for 24 hours. Upon exposure to air, the reaction solution turned to blue from dark brown. The resulting polymer was precipitated in THF, re-dissolved in water, and passed through a silica gel column to remove the catalyst. The aqueous polymer (compound 30) mixture was lyophilized. Elemental analysis: C, theoretical 45.20%; measured 43.40%; H, theoretical 7.10%; measured 8.41%; N, theoretical 4.19%; measured 5.6%; F, theoretical 6.91%; measured 3.20%; Br, theoretical 1.84%; measured 2.80%; O, theoretical 27.63%; measured 29.69%; P, theoretical 7.13%; measured 6.01%. $^1$H NMR (300 MHz, D$_2$O) δ (ppm) 4.20 (s, C$_{PMPC}$OOCH$_2$), 4.13 (s, C$_{PMPC}$CH$_2$CH$_2$OP), 3.99 (s, POCH$_2$), 3.58 (s, C$_{PMPC}$H$_2$N), 3.26 (s, CH$_2$OCH$_2$), 3.13 (s, NCH$_3$), 1.83 (br, C$_{PMA}$CH$_2$C), 1.45 (s, C$_{PU}$H$_2$CH$_2$CH$_2$), 0.80 (s, C$_{PMA}$H$_2$CCH$_3$), no vinyl signals were found at δ 5.5-6.0, indicating complete polymerization of the vinyl groups. Based on the integration values at 1.45 and 0.80 ppm, the MPC monomer conversion was 98%, and therefore an average degree of MPC polymerization of 9.8 was achieved.

EXAMPLE 19: Synthesis of α,ω-BAL-poly(LDI/PTMO) pendent PPAAm (COMPOUND 31).

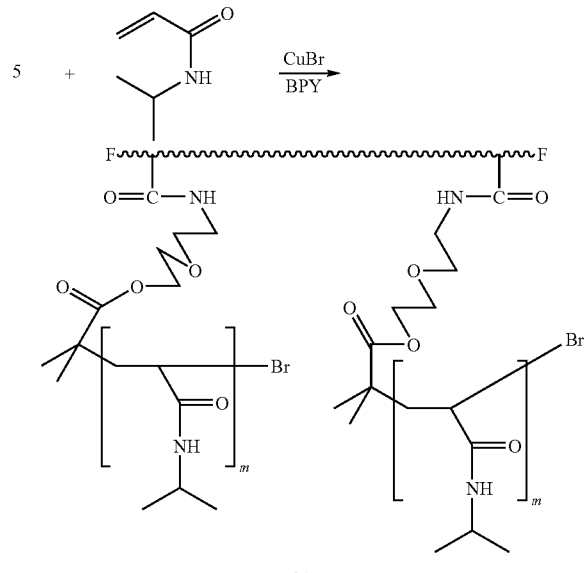

31

The thermo-responsive nature of PPAAm manifests a characteristic of lower critical solution temperature in water at 32° C., above which PPAAm undergoes a hydrophobic collapse and phase separates from solution. SCMSM pendent PPAAm confers this temperature sensitivity to the surface or the interface of the biomaterials or medical devices to which it is incorporated within. The latter materials or devices could have a variety of applications including but not limited to enzyme recovery, triggered release of drugs, or blocking of substrates to protein active sites, and regulation of enzyme activity through thermal precipitation.

After the solution of BMI (compound 5) (2.8867 g, 2.00 mmol of Br) and BPY (0.625 g, 4.00 mmol) were mixed in methanol (30 mL) and purged with ultrahigh-purity nitrogen for 30 minutes, the CuBr catalyst (0.287 g, 2.00 mmol) was added under a nitrogen atmosphere. The stirred mixture was purged with ultrahigh-purity nitrogen for 20 minutes. PAAm (2.263 g, 20.2 μmmol) was added as a solid to the reaction mixture under a nitrogen atmosphere, followed by continuous ultrahigh-purity nitrogen purging for 10 minutes. The reaction mixture was stirred at room temperature for 24 hours. Upon exposure to air, the reaction solution turned to blue from dark brown. The resulting polymer was precipitated in hexane, then re-dissolved in DMF, and passed through an alumina column to remove the catalysts. (Compound 31) was dried under vacuum at 40° C. for 24 hours. $^1$H NMR (300 MHz, CDCl$_3$) was compared with (compound 5) to confirm polymerization. The NMR shifts associated with (compound 31) were found at δ (ppm) 6.28-5.57 (d, dd, d, C$_{PAAm}$H$_2$=CH), 4.16 (q, N$_{PPAAm}$CH), 1.82 (br, C$_{PPAAm}$H$_2$CH), 1.38 (br, C$_{PPAAm}$H$_2$CH), 1.27 (s, C$_{BMI}$OC(CH$_3$)$_2$C$_{PPAA}$), 1.19 (d, NCH(CH$_3$)$_2$). The presence of some vinyl shifts indicated the polymerization was not 100% complete. Based on the integration values at 1.38 and 1.27 ppm, the PAAm monomer conversion was approximately 44.5%. Therefore the estimated average degree of polymerization for PPAAm was 4.45. The presence of amines in this polymerization made the synthesis and purification steps more challenging. This example demonstrates the ability of producing such complex fluorinated macromolecules using methods described here-within.

ATRP Grafted Polymer Syntheses Containing Pharmaceutically Active Compounds

| Example No. | Compound ID | Description |
| --- | --- | --- |
| 20 | (Compound 32) | N-trityl norfloxacin |
|  | (Compound 33) | (BAL-LDI-p-norfloxacin)$_2$-PTMO |
| 21 | (Compound 33) | (BAL-LDI-p-norfloxacin)$_2$-PTMO |
|  | (Compound 34) | N-trityl ciproflaxin-HEMA |
| 22 | (Compound 37) | (BAL-LDI-p-hydrocortisone methacrylate)$_2$-PTMO |
| 23 | (Compound 37) | (BAL-LDI-p-hydrocortisone methacrylate)$_2$-PTMO |
|  | (Compound 38) | Acrylic acid - hydrocortisone |

This section introduces the application of the ATRP synthesis when a pharmaceutically active compound is part of the synthesis. In one strategy, the ATRP polymer is first synthesized and the pharmaceutically active compound is covalently conjugated to the functional groups in the vinyl monomeric units. In another strategy, the pharmaceutically active compound is pre-reacted with a difunctional monomeric unit with specific functional groups suitable for participating in the ATRP synthesis. This pharmaceutically active monomeric unit can easily react with halogenated oligomeric macroinitiators.

EXAMPLE 20: Coupling norfloxacin drug to α,ω-BAL-Poly(LDI/PTMO) pendent poly(hydroxyethyl methacrylate) (COMPOUND 33).

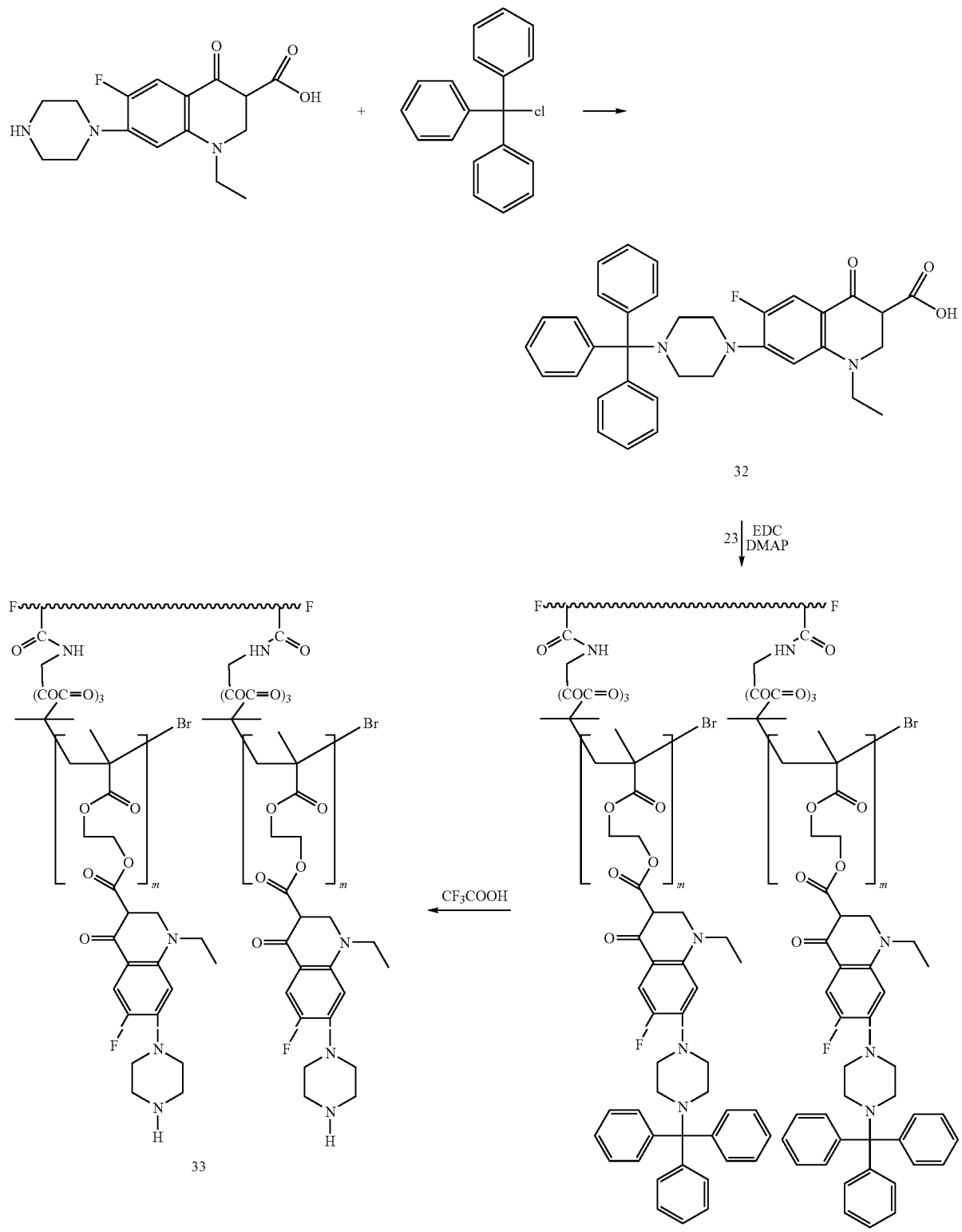

(Compound 23) (1.017 g), EDC (0.1317 g), and DMAP (0.007 g) were dissolved in 40 mL of anhydrous DMF. Amine-protected N-trityl norfloxacin[2] (compound 32) (0.0643 g, 0.1145 mmol) was added to the reaction mixture. The reactor was sealed under a nitrogen atmosphere and stirred at room temperature for 48 hours. Upon reaction completion, the solvent was evaporated at room temperature and the solid residual was washed with $CH_2Cl_2$ five times to remove the catalyst and unreacted N-trityl-norfloxacin. The dried product was mixed with 35 mL of $CHCl_3$, 0.7 mL of $CF_3COOH$, and 0.35 mL of water and stirred at room temperature for 14 hours. Product (compound 33) was automatically precipitated and collected by centrifugation. The final product was purified by washing with $CHCl_3$ and dried under vacuum at 40° C. for 48 hours. FIG. 1 shows gel chromatography tracings of (compound 33) and its precursors. The chromatography by UV 280 indicated that norfloxacin was successfully conjugated to (compound 23) (note the absence of UV absorbance for the PHEMA precursor (tracing 2) versus the presence of the UV tracing for the final product (tracing 4)). The deprotection method used for the amine group on norfloxacin units was safe for ester bonds between norfloxacin and PHEMA units. The chromatography analysis indicated the UV detection in the similar retention time as the protected molecule. Hence the relative molecular weight change due to the elimination of large protecting group was noted. $^1H$ NMR (300 Mhz, DMSO) δ (ppm) 3.92 (s, $C_{PHEMA}OOCH_2$), 3.60 (s, $C_{PHEMA}H_2OCOC_{NF}$), 3.47, 3.33, 2.75, 1.50 and 0.95 signals belong to the NF segment, 1.79 (s, $C_{PHEMA}H_2CCH_3$), 0.80 (s, $C_{PHEMA}H_2CCH_3$), no $C_{PHEMA}H_2OH$ signal was found.

EXAMPLE 21: Polymerization of norfloxacin-oxyethyl methacrylate initiated by tBMI (COMPOUND 33).

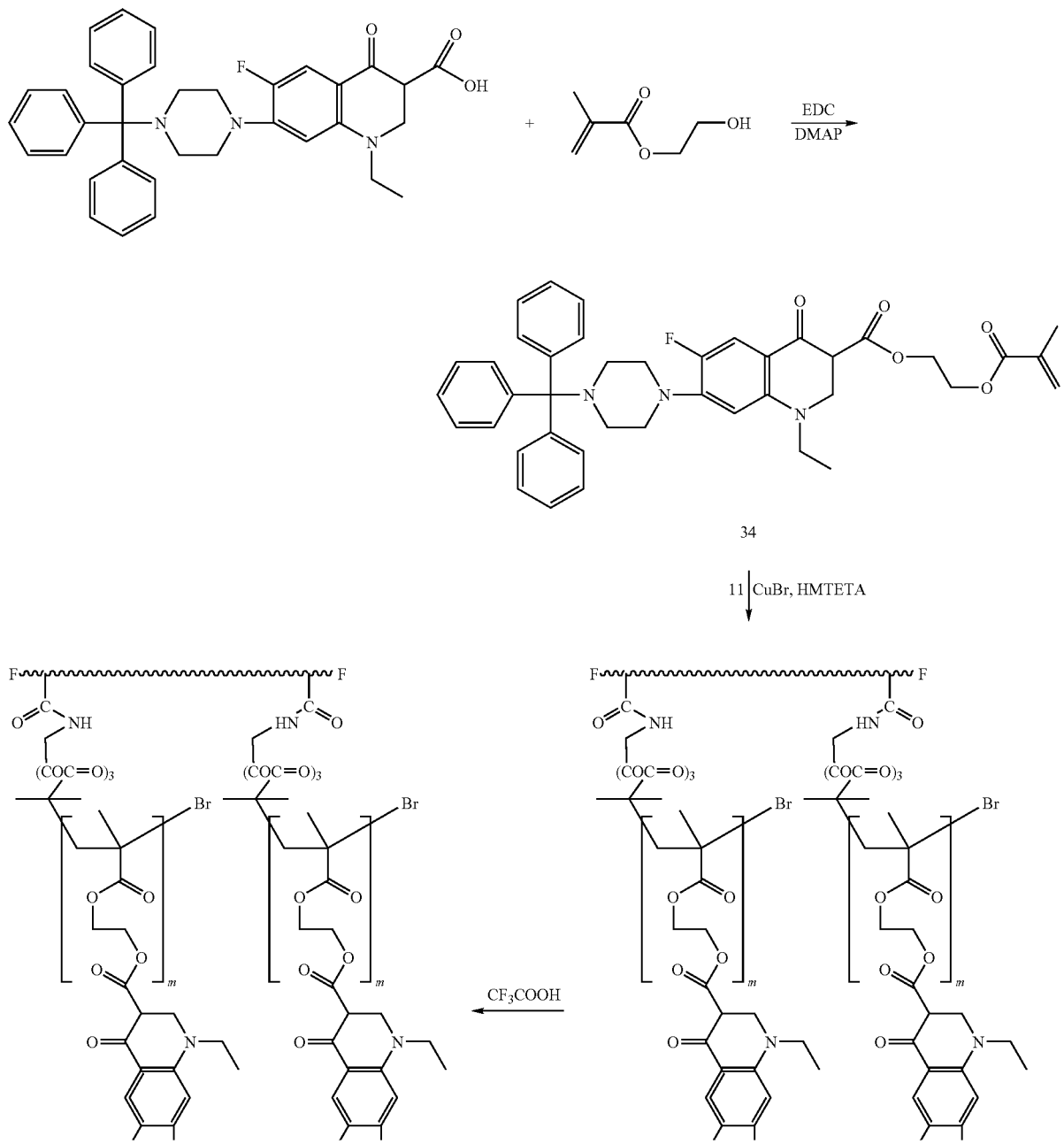

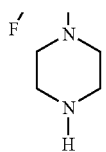
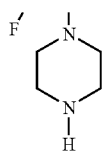

33

N-trityl norfloxacin (compound 32), EDC, and DMAP (in a stoichiometric 1:6:0.5 molar ratio) were dissolved in anhydrous $CH_2Cl_2$. 10% excess HEMA relative to the COOH groups, in molar terms, was added into the reaction mixture. The reaction mixture was stirred at room temperature under a nitrogen atmosphere for 7 days. After rotary evaporating the solvent, the solid residual was extracted with diethyl ether at room temperature. The crude product of this reaction was then washed three times with water. The recovered solid was freeze-dried (compound 34). N-trityl-NF-HEMA (compound 34) (1.154 g, 1.668 mmol), CuBr (0.049 g, 0.3414 mmol) and 0.201 g (0.3414 mmol of Br) tBMI (compound 11) (6 mmol of Br) were dissolved in 10 mL of DMF in a flask sealed with a rubber septum. The mixture was frozen with liquid nitrogen. HMTETA (0.186 mL, 0.6828 mmol) was injected into the flask with a syringe. The solution was freeze-thawed five times by using vacuum line and liquid nitrogen. After filling with ultrahigh-purity nitrogen, the flask was heated in an oil bath to 55° C. for 24 hours. The polymerization was stopped by cooling the flask in ice water. The solution was diluted with THF and filtered through a silica gel column to remove the catalyst. After solvent removal from the filtered solution, the solid was dried and re-dissolved in 10 mL of $CH_2Cl_2$. $CF_3COOH$ (1 mL) and 0.5 mL of water were added to the solution. The reaction mixture was stirred at room temperature for 14 hours. The product (compound 33) was automatically precipitated and collected by centrifugation. The final product was purified by washing with $CH_2Cl_3$ and dried under vacuum at 40° C. overnight. $^1H$ NMR (300 MHz, DMSO) δ (ppm) 8.64 (s, $FC_{NF}CH$), 7.85 (b, $FC_{NF}CCH$), 7.13 (b, $OC_{NF}CCHN$), 6.06 (s, $CH_aH_b=C_{HEMA}$), 5.70 (s, $CH_aH_b=C_{HEMA}$), 4.42 (bb, $C_{PHEMA}OOCH_2$), 4.18 (bb, $N_{NF}CH_2CH_3$), 3.71 (br, $COOCH_2$), 3.44 (m, $N_{NF}CH_2CH_3$), 3.33 (s, $CH_2OCH_2$), 1.91 (s, $C(CH_3)_2$), 1-89 (s, $C_{PHEMA}H_2CCH_3$), 1.76 (m, $_{NF}NCH_2CH_2N$), 1.50 (s, $_{PU}CH_2CH_2CH_2$), 1.14 (t, $_{NF}NH$), 0.79 (s, $_{PHEMA}CCH_3$). Based on the NMR analysis and fingerprint region at 6.06, 5.70 and 1.89, the NF-HEMA monomer conversion reached 81% in this polymerization reaction.

EXAMPLE 22: Synthesis of α,ω-BAL-poly(LDI/PTMO) pendent poly(hydrocortisone methacrylate) - coupling HC to α,ω-BAL-poly(LDI/PTMO)-p-PMAA (COMPOUND 37).

26 +

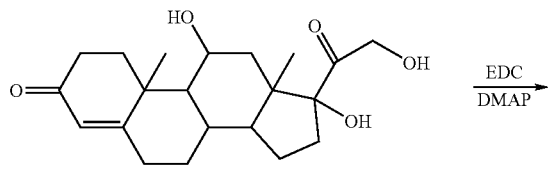

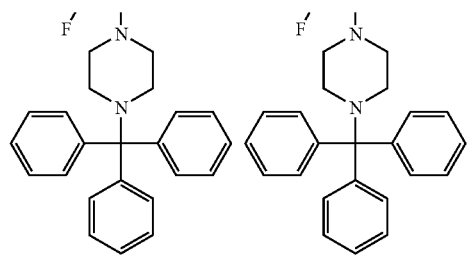

-continued

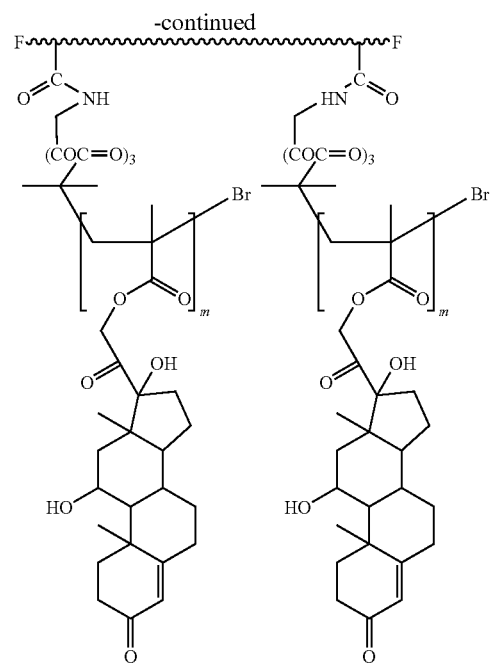

37

(Compound 26) (0.5 g, 4.227 mmol of COOH), EDC (5.531 g, 28.846 mmol) and DMAP (0.270 g, 0.211 mmol) were added to 100 ml of anhydrous DMF. Hydrocortisone (2.0 g, 5.517 mmol) was added to the reaction mixture and the solution was stirred under a nitrogen atmosphere at room temperature for two weeks. Upon the reaction completion the solvent was removed at 40° C. and the solid residual was washed using water and centrifuged three times to remove catalyst and the unreacted HC and -p-PMA. The final product (compound 37) was dried under vacuum at 40° C. overnight. Elemental analysis: (based on HC:COOH=1:1): C, theoretical 53.68%; measured 51.29%; H, theoretical 6.07%; measured 7.99%; N, theoretical 0.69%; measured 4.74%; F, theoretical 4.92%; measured 0.34%; Br, theoretical 3.93%; measured 0.029%; O, theoretical 30.71%; measured 35.63%. Therefore, based on the C and O content measured (supported by a drop in fluorine from the PMAA precursor (example 15) 3.56%), the HC coupling efficiency was 100% complete (i.e. the HC content is about 2.08 mmol/g). $^1H$ NMR (300 MHz, in DMSO) δ (ppm) 5.56 (s, $C^4_{HC}H$), 5.40 (s, $N_{PU}H$), 5.00 (m, $C^{17}_{HC}OH$), 4.27 (m, $C^{11}_{HC}HOH$), 4.0-3.0 (m, $C_{PMA}OOC^{21}_{HC}H_2$, $C_{PU}H_2OCH_2$, NCH, $NCH_2$, NH), 2.56-1.5 (m, $C^{16}_{HC}H_aH_b$, $CF_2CH_2$, $C^6_{HC}H_2$, $C^2_{HC}H_2$, $C^1_{HC}H_2$, $C^7_{HC}H_2$, $C^{14}_{HC}H$, $C^{15}_{HC}H_2$, $C_{PU}H_2CH_2CH_2$, $C^{12}_{HC}H_2$), 1.36 (s, $C^{19}_{HC}H_3$), 1.3-0.8 (m, $C_{PMA}H_3$, $C_{PMA}H_2$), 0.75 (s, $C^{18}_{HC}H_3$).

EXAMPLE 23: Polymerization of hydrocortisone acrylate initiated by tBMI (COMPOUND 37)

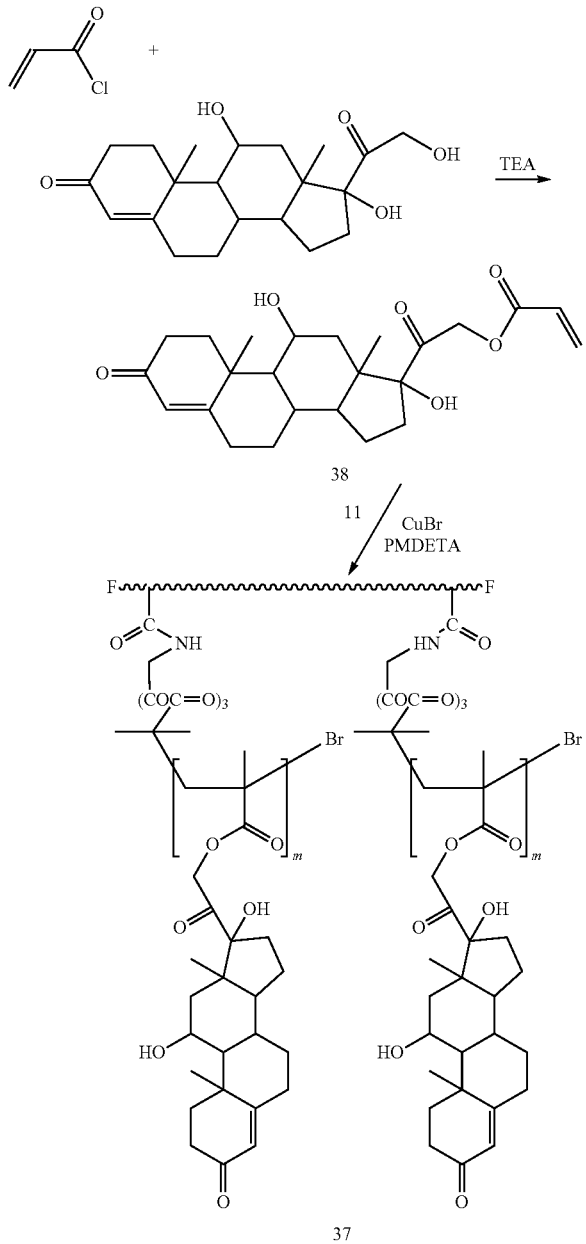

Synthesis of (compound 38): hydrocortisone (2.5 g, 6.90 mmol) was transferred to a flame-dried 250 mL reaction flask equipped with a stir bar. The flask was capped with a rubber septum and filled with dried nitrogen gas from a balloon. Anhydrous dichloromethane (100 mL) was transferred to the flask via a syringe. A milky suspension was formed due to incomplete dissolution of hydrocortisone in dichloromethane ($CH_2Cl_2$). TEA (1.10 ml, 7.89 mmol) was transferred to the reaction flask by a syringe. A solution of acryloyl chloride (0.65 g, 7.18 mmol in 10 ml of dry $CH_2Cl_2$) was added dropwise to the reaction flask via a syringe. The addition was completed in 10 minutes. As the solution of acryloyl chloride was added, the suspension became less milky. The reaction flask was kept stirring for 16 hours at room temperature. 80 mL of $CH_2Cl_2$ was removed by rotary evaporator to yield a milky suspension. Flash column chromatography was used to isolate the product (pure hydrocortisone-containing acrylate, (compound 38)) from the milky suspension using $CH_2Cl_2$ as the eluent. $R_f$ of (compound 38) in diethyl ether containing 2 wt % ethanol as the inhibitor: 0.46. $^1$H NMR (300 MHz, $CDCl_3$) δ (ppm) 6.49 (1H, dd, —$OCCHCH_2$), 6.23 (1H, dd, —$OCHCH_2$), 5.92 (1H, dd, —$CHCH_2$), 5.68 (1H, s, $C^4_{HC}H$), 5.13 (1H, d, $OCCH_2O$—), 4.94 (1H, d, $OCCH_2O$—), 4.48 (1H, b, $C^{11}_{HC}HOH$), 2.87 (1H, m, $C^{11}_{HC}HOH$), 2.60-0.94 (25H, m, $C^1_{HC}H_2$, $C^2_{HC}H_2$, $C^6_{HC}H_2$, $C^7_{HC}H_2$, $C^8_{HC}H$, $C^9_{HC}H$, $C^{12}_{HC}H_2$, $C^{14}_{HC}H$, $C^{15}_{HC}H_2$, $C^{16}_{HC}H_2$, $C^{18}_{HC}H_3$, $C^{19}_{HC}H_3$). Synthesis of (compound 37): (compound 38) (0.494 g, 1.186 mmol), CuBr (0.034 g, 0.237 mmol) and (compound 11) (0.139 g) were dissolved in 5 ml of DMF in a flask equipped with a stir bar. The flask was sealed with a rubber septum. The reaction mixture was bubbled with a gentle flow of argon for 30 minutes. PMDETA (0.1 ml, 0.082 g, 0.474 mmol), previously weighed in a 25 ml vial and purged with argon, was added to the reaction flask via a syringe. The flask was heated in an oil bath at 70° C. overnight. The next day, the reaction flask was cooled to room temperature. Flash column chromatography of the reaction mixture with $CH_2Cl_2$ first and then MeOH yielded (compound 37). $^1$H NMR (300 MHz, DMSO) found: δ (ppm) 5.54 (s, $C^4_{HC}H$), 5.08 (b, $N_{PU}H$), 4.77 (b, $N_{PU}H$), 4.26 (m, $OCH_2CH_2CF_2$ and $NCHC=O$), 3.30 (b, $CH_2OCH_2$), 2.65-2.25 (m, $OCH_2CH_2CF_2$), 2.25-0.65 (m, $C^1_{HC}H_2$, $C^2_{HC}H_2$, $C^6_{HC}H_2$, $C^7_{HC}H_2$, $C^8_{HC}H$, $C^9_{HC}H$, $C^{12}_{HC}H_2$, $C^{14}_{HC}H$, $C^{15}_{HC}H_2$, $C^{16}_{HC}H_2$, $C^{18}_{HC}H_3$, $C^{19}_{HC}H_3$, $C_{PU}H_2CH_2CH_2$, $C_{PA}H_2H$, $C_{PA}H_2H$). The disappearance of the acrylate protons on $^1$H NMR spectra indicated the polymerization of drug monomer.

Covalent and Non-Covalent Conjugation of Pharmaceutically Active Compounds with ATRP Grafted Polymers

| Example. No. | Compound ID | Description |
|---|---|---|
| | | Non-covalent conjugation |
| 24 | (Compound 39) | (Compound 26)/ibuprofen |
| 25 | (Compound 40) | (Compound 26)/hydrocortisone |
| 26 | (Compound 41) | (Compound 26)/dexamethasone |
| 27 | (Compound 42) | (Compound 26)/paclitaxel |
| 28 | (Compound 43) | (Compound 27)/cisplatin |
| 29 | (Compound 44) | (Compound 26)/doxorubicin |
| 30 | (Compound 45) | (Compound 23)/methotrexate |
| 31 | (Compound 46) | (Compound 26)/ascorbic acid |
| 32 | (Compound 47) | (Compound 23)/salicylic acid |
| 33 | (Compound 48) | (Compound 26)/chlorhexidine |
| 34 | (Compound 49) | (Compound 26)/oxybutynin |
| 35 | (Compound 50) | (Compound 23)/vitamin K1 |
| 36 | (Compound 51) | (Compound 22)/vitamin K1 |
| 37 | (Compound 52) | (Compound 23)/aspirin |
| | | Covalent conjugation |
| 38 | (Compound 53) | Covalent conjugation of (compound 26) to paclitaxel |
| 39 | (Compound 54) | Covalent conjugation of (compound 23) to methotrexate |

The synthesis of well-defined polymers by atom transfer radical polymerization (ATRP) was described in the first section of this patent. This polymerization method provided good control over molecular weights and molecular weight distributions, with monomer conversions as high as 95%. The rational design and synthetic strategies implemented in monomer selection in terms of the quantity of active sites and functional groups, constructed macroinitiators that made it possible to modulate the building blocks necessary for drug conjugation in covalent and noncovalent manners. The amphiphilic, ionic and nonionic characteristics that can be introduced into oligomeric structures with unique fluorine content represents a promising technique for the design of new multiblock copolymers in drug delivery. The overall inter-chain association of monomeric units and drug moieties is of great importance in the design of fluorinated platforms. This section demonstrates the interaction and release profile of a number of pharmaceutically active compounds from the polymers synthesized using the ATRP technique.

Noncovalent Conjugation

EXAMPLE 24

α,ω-BAL-poly(LDI/PTMO)-p-PMAA (Compound 26): Ibuprofen (Compound 39)

Ibuprofen: this compound is a non-steroidal anti-inflammatory drug. Its mechanism of action is through inhibition of cyclooxygenase (COX) and hence prostaglandin synthesis.

Figure 2:
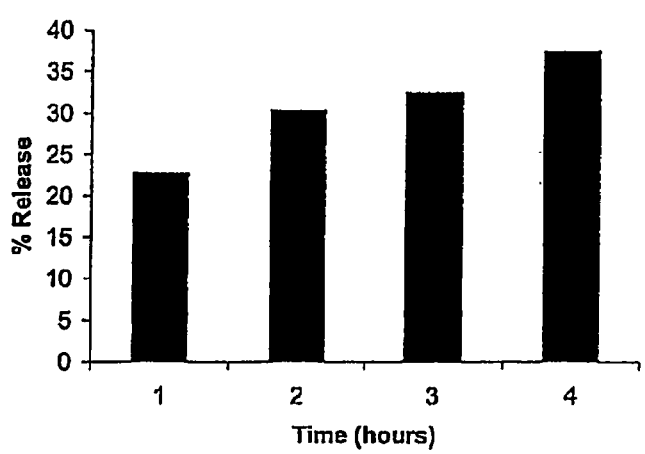
FIG. 2 is a plot of the release of ibuprofen from a (compound 39) (DMF)/Chronothane film showing the ability of the drug to dissociate from the delivery platform.

Ibuprofen (0.469 g, $2.3 \times 10^{-3}$ mol) was dissolved in DMF (2 mL). (Compound 26) (0.054 g, 8.68 mg ibuprofen/mg of (compound 26)) was dissolved in DMF (2 mL) at room temperature under a nitrogen atmosphere. Once completely dissolved, the ibuprofen solution was added dropwise, over 75 minutes, to the (compound 26) solution. The reaction mixture was sealed and left under a nitrogen atmosphere for 24 hours. The excess solvent was removed and the final product (compound 39) was isolated and dried. Film preparation: the isolated product (35 mg) was dissolved in a 10% DMF solution of Chronothane 80A (6 mL). This solution was pipetted into 4×4 cm PTFE wells and cast into films. Films were processed in a 60° C. flow oven and a 50° C. vacuum oven. Films were monitored for surface defects and general quality. Release profile: a strip of film (0.069 g) (1.3×0.75 cm) was cut and placed in a glass vial containing PBS (1.5 mL) at 37° C. The UV/Vis absorbance spectrum was measured at various time points (1, 2, 3, and 4 hours). The release profile was also monitored for (compound 39) when isolated from methanol. The release profiles are summarized in Table 1 and FIG. 2.

TABLE 1

Concentration and mass of ibuprofen released from (compound 39)/Chronothane films in PBS, 37° C.

| Time (hours) | DMF preparation | | Methanol preparation | |
|---|---|---|---|---|
| | Concentration (mg/mL) | Mass released (mg) | Concentration (mg/mL) | Mass released (mg) |
| 0 | 0 | 0 | 0 | 0 |
| 1 | 0.549 | 0.823 | 0.326 | 0.489 |
| 2 | 0.182 | 0.274 | 0.044 | 0.067 |
| 3 | 0.050 | 0.075 | 0.218 | 0.327 |
| 4 | 0.118 | 0.177 | 0.074 | 0.112 |

EXAMPLE 25

α,ω-BAL-poly(LDI/PTMO)-p-PMAA (Compound 26): Hydrocortisone (Compound 40)

Hydrocortisone: this compound is known as a corticosteroid hormone which is produced by the adrenal cortex. It is generally used for the treatment of allergies and inflammation.

Figure 3:
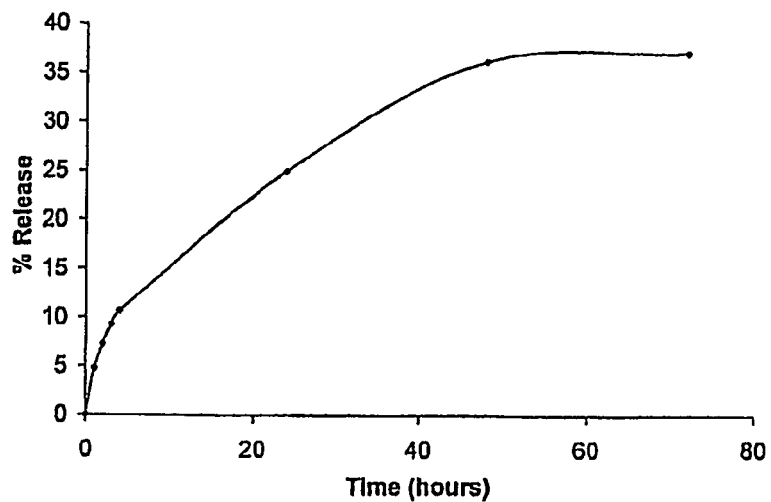
FIG. 3 is a plot of the release of hydrocortisone from a (compound 40)/Carbothane film showing that 35-40% of the drug is released within 70-80 hours.

Hydrocortisone (0.764 g, $2.1 \times 10^{-3}$ mol) was dissolved in methanol (80 mL). (Compound 26) (0.050 g, 15.3 mg hydrocortisone/mg of (compound 26)) was dissolved in methanol (20 mL) at room temperature under a nitrogen atmosphere. Once completely dissolved, the hydrocortisone solution was added dropwise, over 100 minutes, to the (compound 26) solution. The reaction mixture was sealed and left under a nitrogen atmosphere for 72 hours. The excess solvent was removed and the final product (compound 40) was isolated and dried. Film preparation: (compound 26) (33 mg) was dissolved in a 10% DMAc solution of Carbothane 85A (6 mL). This solution was pipetted into a 4×4 cm PTFE well and cast into a film. The film was processed in a 60° C. flow oven and a 50° C. vacuum oven. The film was monitored for surface defects and general quality. Release profile: a strip of film (0.058 g) (1.3×0.75 cm) was cut and placed in a glass vial containing PBS (1.5 mL) at 37° C. The UV/Vis absorbance spectrum was measured at various time points (1, 2, 3, 4, 24, 48, and 72 hours), and the release profile plotted in FIG. 3.

EXAMPLE 26

α,ω-BAL-poly(LDI/PTMO)-p-PMAA (Compound 26): Dexamethasone (Compound 41)

Dexamethasone: dexamethasone is a potent synthetic member of the glucocortid class of steroid hormones. It acts as an anti-inflammatory and immunosuppressant. Its potency is about 40 times that of hydrocortisone.

Figure 4:
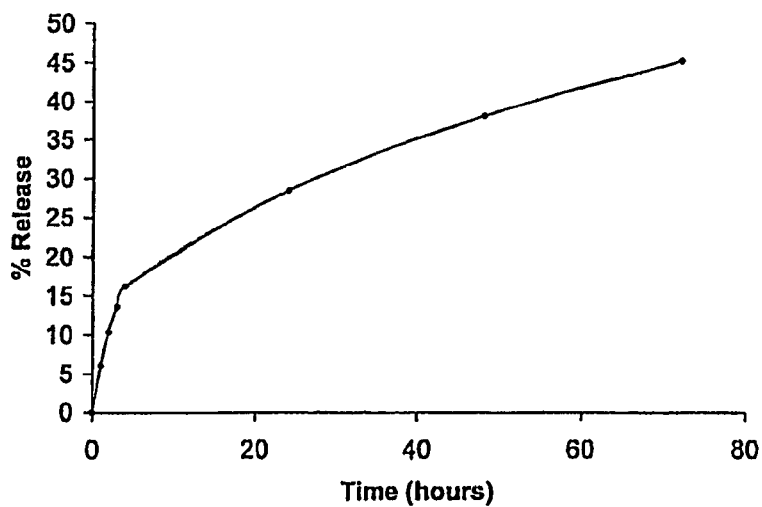
FIG. 4 is a plot of the release of dexamethasone from a (compound 41)/Chronothane film showing that 40-50% of the drug is released within 70-80 hours.
Figure 5:
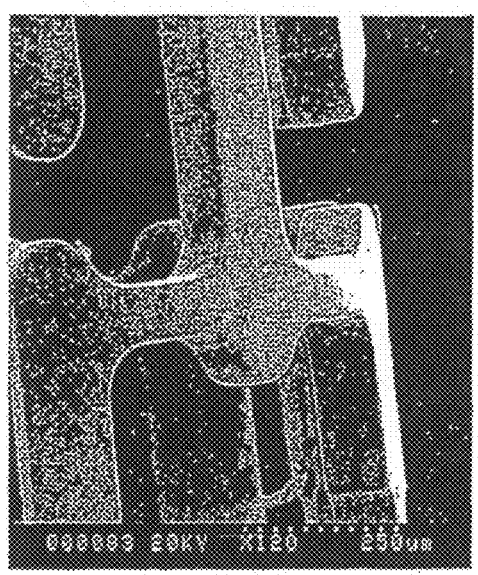
FIG. 5 is an SEM image of a stent coated with (compound 41) showing a good strut coverage with minimum webbing.

Dexamethasone (0.332 g, $8.46 \times 10^{-4}$ mol) was dissolved in methanol (11 mL). (Compound 26) (0.100 g, 3.32 mg dexamethasone/mg of (compound 26)) was dissolved in methanol (3 mL) at room temperature under a nitrogen atmosphere. Once completely dissolved, the dexamethasone solution was added dropwise, over 120 minutes, to the (compound 26) solution. The reaction mixture was sealed and left under a nitrogen atmosphere for 72 hours. The excess solvent was removed and the final product (compound 41) was isolated and dried. Film preparation: the isolated product (29 mg) was dissolved in a 10% DMF solution of Chronothane 80A (6 mL). This solution was pipetted into a 4×4 cm PTFE well and cast into a film. The film was processed in a 60° C. flow oven and a 50° C. vacuum oven. The film was monitored for surface defects and general quality. Release profile: a strip of film (0.081 g) (1.3×0.75 cm) was cut and placed in a glass vial containing PBS (1.5 mL) at 37° C. The UV/Vis absorbance spectrum was measured at various time points (1, 2, 3, 4, 24, 48, and 72 hours), and the release profile plotted in FIG. 4. The coating performance was established by dissolving (compound 41) in DMF and sprayed on a 316 stainless steel stent. The stent was dried in a flow oven before SEM analysis was performed (FIG. 5).

EXAMPLE 27

α,ω-BAL-poly(LDI/PTMO)-p-PMAA (Compound 26): Paclitaxel (Compound 42)

Paclitaxel: this is a potent compound used in the treatment of cancer and prevention of restenosis (recurrent narrowing) of coronary arteries. Paclitaxel interferes with the normal function of microtubule growth.

Paclitaxel (0.089 g, $1.04 \times 10^{-4}$ mol) was dissolved in DMF (1 mL). (Compound 26) (0.048 g, 1.85 mg paclitaxel/mg of (compound 26)) was dissolved in DMF (2 mL) at room temperature under a nitrogen atmosphere. Once completely dissolved, the paclitaxel solution was added dropwise, over 30 minutes, to the (compound 26) solution. The reaction mixture was sealed and left under a nitrogen atmosphere for 24 hours. The excess solvent was removed and the final product (compound 42) was isolated and dried. Film preparation: the isolated product (30 mg) was dissolved in a 10% DMAc solution of Carbothane 85A (6 mL). This solution was pipetted into a 4×4 cm PTFE well and cast into a film. The film was processed in a 60° C. flow oven and a 50° C. vacuum oven. The film was monitored for surface defects and general quality. Release profile: a strip of film (0.070 g) (1.3×0.75 cm) was cut and placed in a glass vial containing PBS with Tween (1.5 mL) at 37° C.

Figure 6:
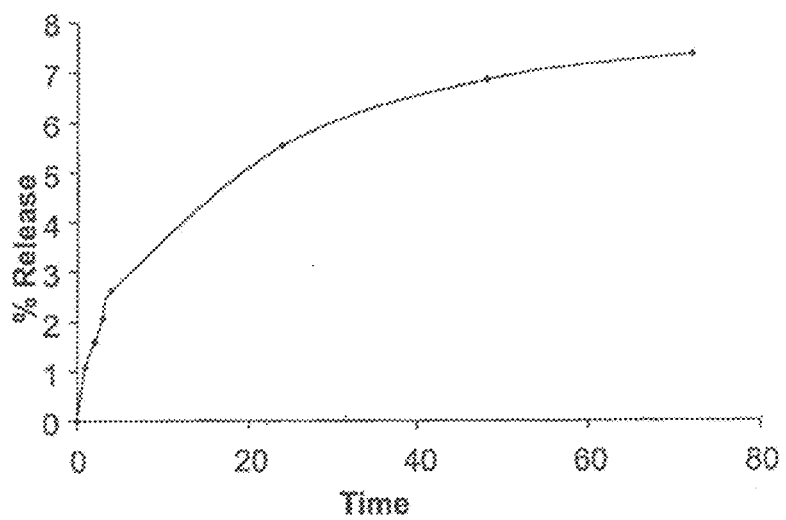
FIG. 6 is a plot of the release of paclitaxel from a (compound 42)/Carbothane film showing a very slow release over 70 hours.

The UV/Vis absorbance spectrum was measured at various time points (1, 2, 3, 4, 24, 48, and 72 hours), and the release profile plotted in FIG. 6.

EXAMPLE 28

α,ω-BAL-poly(LDI/PTMO)-p-PMAA-Na (Compound 27): Cisplatin (Compound 43)

Cisplatin: this is a platinum based chemotherapy drug used to treat various types of cancers. Cisplatin acts by crosslinking DNA in several different ways, making it impossible for rapidly dividing cells to duplicate their DNA for mitosis.

Figure 7:
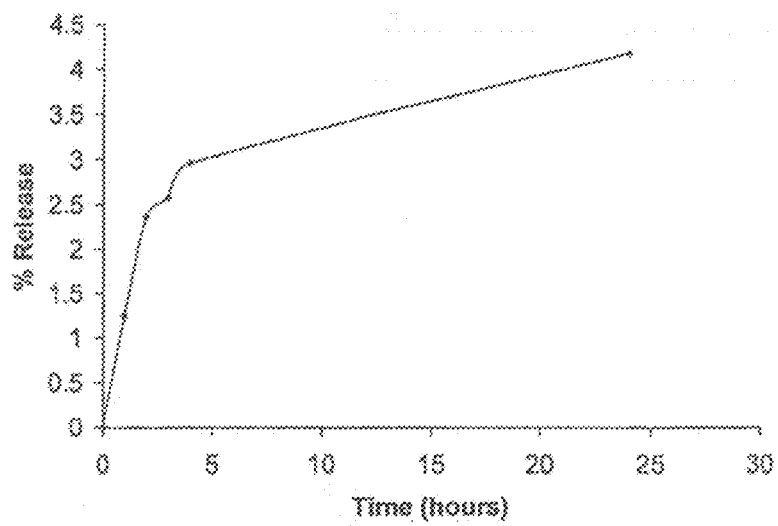
FIG. 7 is a plot of the release of cisplatin from (compound 43) in water showing a very slow release over 25 hours.

Cisplatin (0.007 g, 2.33×10$^{-5}$ mol) was dissolved in water (6 mL). (Compound 27) (0.056 g, 0.125 mg cisplatin/mg of (compound 27)) was dissolved in water (4 mL) at room temperature under a nitrogen atmosphere. When completely dissolved, the (compound 27) solution was added dropwise, over 60 minutes, to the cisplatin solution. The reaction mixture was sealed and left under a nitrogen atmosphere for 24 hours. The excess solvent was removed and the final product (compound 43) was isolated and dried. Release profile: the isolated product (0.025 g) was dissolved in water (1.5 mL) and placed at 37° C. The UV/Vis absorbance spectrum was measured at various time points (1, 2, 3, 4, and 24 hours), and the release profile plotted in FIG. 7.

EXAMPLE 29

α,ω-BAL-poly(LDI/PTMO)-p-PMAA (Compound 26): Doxorubicin (Compound 44)

Doxorubicin: this compound is a DNA-interacting drug widely used in chemotherapy. It has an anthracycline structure and it intercalates DNA. It is commonly used in the treatment of a wide range of cancers. It binds to DNA where it can inhibit the progression of the enzyme topoisomerase II, which unwinds DNA for transcription, preventing the DNA double helix from being resealed and thereby stopping the process of replication.

Figure 8:
FIG. 8 is a microscopy image of a solution coating of (compound 44) on a non-electropolished stainless steel coupon. The stainless steel coupon has a lot of surface imperfection at microscopic level, however the coating is uniform.

Doxorubicin hydrochloride (0.0043 g, 7.4×10$^{-6}$ mol) was dissolved in methanol (1 mL). (Compound 26) (0.005 g, 0.86 mg doxorubicin/mg of (compound 26)) was dissolved in methanol (1 mL) at room temperature under a nitrogen atmosphere. Once completely dissolved, the doxorubicin solution was added dropwise, over 30 minutes, to the (compound 26) solution. The reaction mixture was sealed and left under a nitrogen atmosphere for 24 hours. The excess solvent was removed and the final product was isolated and dried. Release profile: (compound 44) (9.3 mg) was dissolved in water (1.5 mL). The UV/Vis absorbance spectrum was measured at various time points (1 and 2 hours) and the release profile is tabulated in Table 2. The coating performance of (compound 44) was established by dissolving (compound 44) in methanol and dropped on a stainless steel coupon. The (compound 44) droplet on the stainless steel coupon was let dried and observed under a microscopy (FIG. 8). The imperfections observed in FIG. 8 were due to the non-electropolished stainless steel surface features.

TABLE 2

Concentration and mass of doxorubicin released from (compound 44) in water, 37° C.

| Time (hours) | Concentration (mg/mL) | Mass released (mg) |
|---|---|---|
| 1 | 1.25 | 1.87 |
| 2 | 1.18 | 1.78 |

EXAMPLE 30

α,ω-BAL-poly(LDI/PTMO)-p-PHEMA (Compound 23): Methotrexate (Compound 45)

Methotrexate: this compound is a drug used in treatment of cancer and autoimmune diseases. It inhibits the metabolism of folic acid.

Figure 9:
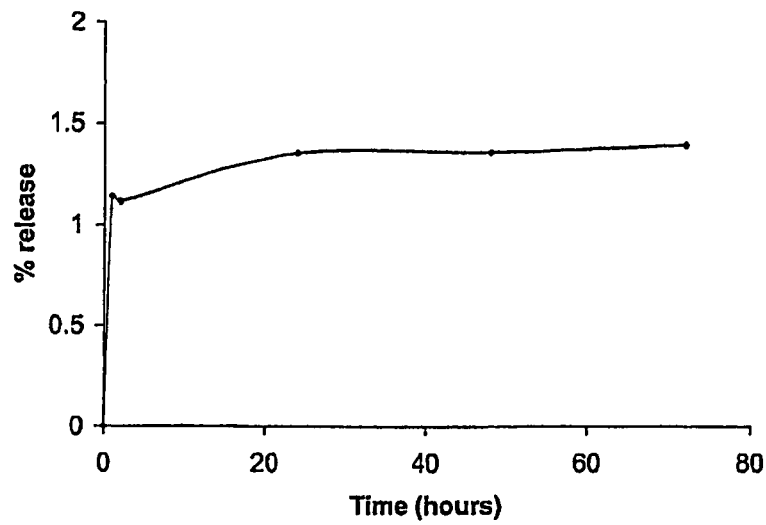
FIG. 9 is a plot of the release of methotrexate from a (compound 45)/Carbothane film indicating a strong interaction between the delivery platform and methotrexate.

Methotrexate (0.0127 g, 2.8×10$^{-5}$ mol) was dissolved in DMSO (1 mL). (Compound 23) (0.048 g, 0.265 mg methotrexate/mg of (compound 23)) was dissolved in DMSO (1 mL) at room temperature under a nitrogen atmosphere. Once completely dissolved, the methotrexate solution was added dropwise, over 15 minutes, to the (compound 23) solution. The reaction mixture was sealed and left under a nitrogen atmosphere for 24 hours. The excess solvent was removed and the final product (compound 45) was isolated and dried. Film preparation: the isolated product (29 mg) was dissolved in a 10% DMAc solution of Carbothane 85A (6 mL). This solution was pipetted into a 4×4 cm PTFE well and cast into a film. The film was processed in a 60° C. flow oven and a 50° C. vacuum oven. The film was monitored for surface defects and general quality. Release profile: a strip of film (0.071 g) (1.3×0.75 cm) was cut and placed in a glass vial containing PBS (1.5 mL) at 37° C. The UV/Vis absorbance spectrum was measured at various time points (1, 2, 24, 48, and 72 hours) and the release profile plotted in FIG. 9.

EXAMPLE 31

α,ω-BAL-poly(LDI/PTMO)-p-PMAA (Compound 26): Ascorbic Acid (Compound 46)

Ascorbic acid: this compound has antioxidant properties. It acts as an antioxidant by being itself available for energetically favorable oxidation.

Ascorbic acid (0.372 g, 2.1×10$^{-3}$ mol) was dissolved in DMF (2 mL). (Compound 26) (0.048 g, 7.75 mg ascorbic acid/mg of (compound 26)) was dissolved in DMF (2 mL) at room temperature under a nitrogen atmosphere. Once completely dissolved, the ascorbic acid solution was added dropwise, over 75 minutes, to the (compound 26) solution. The reaction mixture was sealed and left under a nitrogen atmosphere for 24 hours. The excess solvent was removed and the final product (compound 46) was isolated and dried. Film preparation: the isolated product (34 mg) was dissolved in a 10% DMF solution of Chronothane 80A (6 mL). This solution was pipetted into a 4×4 cm PTFE well and cast into a film. The film was processed in a 60° C. flow oven and a 50° C. vacuum oven. The film was monitored for surface defects and general quality. Release profile: a strip of film (0.070 g)

Figure 10:
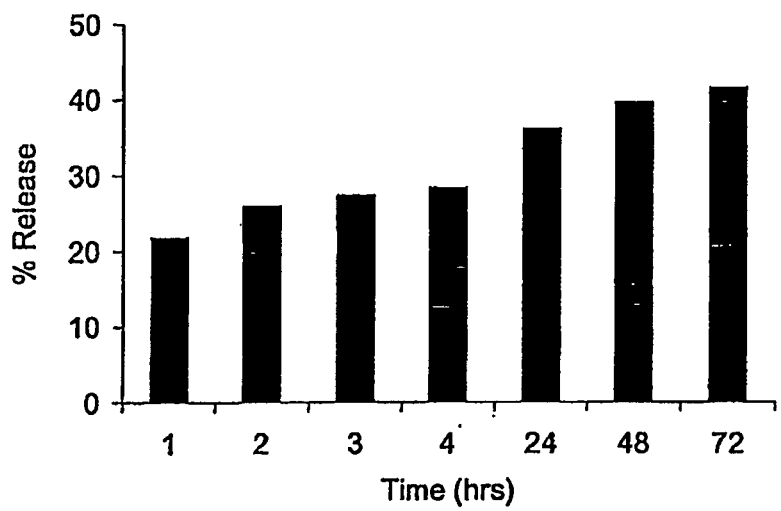
FIG. 10 is a plot of the release of ascorbic acid (vitamin C) from a (compound 46)/Chronothane film showing 40-50% release within 72 hours.

(1.3×0.75 cm) was cut and placed in a glass vial containing PBS (2.5 mL) at 37° C. The UV/Vis absorbance spectrum was measured at various time points (1, 2, 3, 4, 24, 48, and 72 hours), and the release profile plotted in FIG. 10.

EXAMPLE 32

α,ω-BAL-poly(LDI/PTMO)-p-PHEMA (Compound 23): Salicylic Acid (Compound 47)

Salicylic Acid: this compound is the key additive in many skin-care products. It treats acne by causing skin cells to slough off more readily, preventing pores from clogging up.
Salicylic acid (0.009 g, $6.5 \times 10^{-5}$ mol) was dissolved in methanol (1 mL). (Compound 23) (0.104 g, 0.086 mg salicylic acid/mg of (compound 23)) was dissolved in DMF (1 mL) at room temperature under a nitrogen atmosphere. Once completely dissolved, the salicylic acid solution was added dropwise, over 45 minutes, to the (compound 23) solution. The reaction mixture was sealed and left under a nitrogen atmosphere for 24 hours. The excess solvent was removed and the final product (compound 47) was isolated and dried. (Compound 47) was also isolated from methanol. Film preparation: the isolated product (21 mg) was dissolved in a 10% DMAc solution of Carbothane 85A (6 mL). This solution was pipetted into 4×4 cm PTFE wells and cast into films. Films were processed in a 60° C. flow oven and a 50° C. vacuum oven. Films were monitored for surface defects and general quality. Release profile: a strip of film (0.081 g) (1.3×0.75 cm) was cut and placed in a glass vial containing PBS (1.5 mL) at 37° C. The UV/Vis absorbance spectrum was measured at various time points (1, 2, and 3 hours), and the release profile plotted in FIG. 11. The surfaces of the films after 3 hours of incubation were characterized by SEM. The SEM image of (compound 47) film isolated from methanol showed no crystallization of the drug at the surface (FIG. 12). Likewise, (compound 47) film isolated from DMF showed a homogeneous platform with no phase separation (FIG. 13).

EXAMPLE 33

α,ω-BAL-poly(LDI/PTMO)-p-PMAA (Compound 26): Chlorhexidine (Compound 48)

Figure 14:
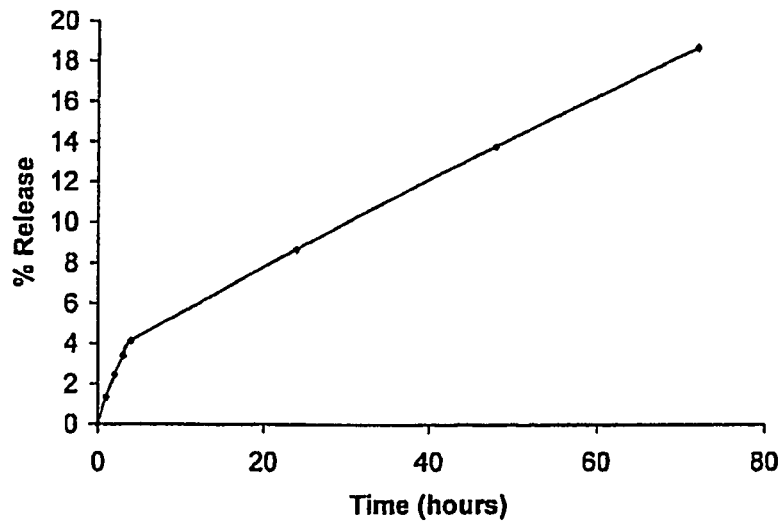
FIG. 14 is a plot of the release of chlorhexidine from a (compound 48)/Carbothane film showing 18-20% release within 80 hours.

Chlorohexidine is a biguanide compound used as an antiseptic agent with topical antibacterial activity. Chlorhexidine is positively charged and reacts with the negatively charged microbial cell surface, thereby destroying the integrity of the cell membrane. Subsequently, chlorhexidine penetrates into the cell and causes leakage of intracellular components leading to cell death. Since gram positive bacteria are more negatively charged, they are more sensitive to this agent.
Chlorhexidine (0.513 g, $1.01 \times 10^{-3}$ mol) was dissolved in DMF (21 mL). (Compound 26) (0.049 g, 10.47 mg chlorhexidine/mg (compound 26)) was dissolved in DMF (5 mL) at room temperature under a nitrogen atmosphere. Once completely dissolved, the chlorhexidine solution was added dropwise, over 160 minutes, to the (compound 26) solution. The reaction mixture was sealed and left under a nitrogen atmosphere for 72 hours. The excess solvent was removed and the final product (compound 48) was isolated and dried. Film preparation: the isolated product (37 mg) was dissolved in a 10% DMAc solution of Carbothane 85A (6 mL). This solution was pipetted into a 4×4 cm PTFE well and cast into a film. The film was processed in a 60° C. flow oven and a 50° C. vacuum oven. The film was monitored for surface defects and general quality. Release profile: a strip of film (0.070 g) (1.3×0.75 cm) was cut and placed in a glass vial containing water (1.5 mL) at 37° C. The UV/Vis absorbance spectrum was measured at various time points (1, 2, 3, 4, 24, 48, and 72 hours), and the release profile plotted in FIG. 14.

EXAMPLE 34

α,ω-BAL-poly(LDI/PTMO)-p-PMAA (Compound 26): Oxybutynin (Compound 49)

Figure 15:
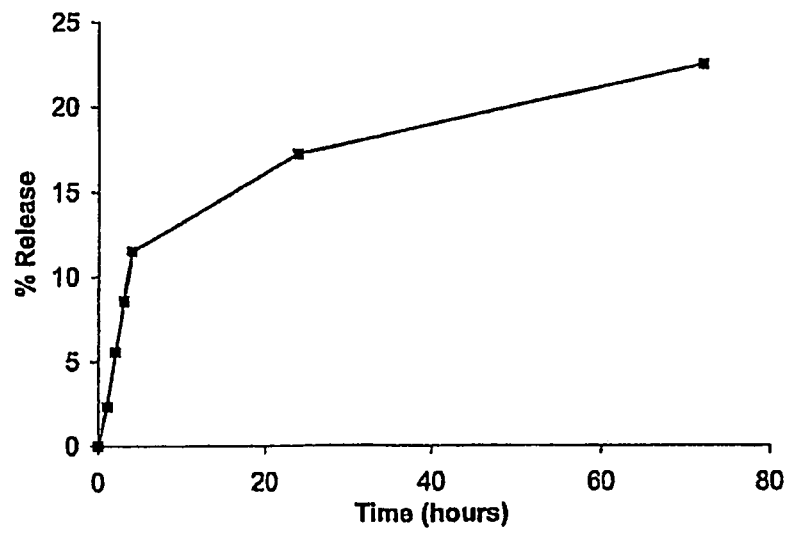
FIG. 15 is a plot of the release of oxybutynin from a (compound 49)/Chronothane film in artificial urine showing 20-25% release within 70 hours.

Oxybutynin is an anticholinergic compound and used to relieve urinary and bladder difficulties, including frequent urination and inability to control urination. Its mechanism of action is by decreasing muscle spasms of the bladder. It competitively antagonizes the M1, M2, and M3 subtypes of the muscarinic acetylcholine receptor.
Oxybutynin hydrochloride was desalted prior to use in this example. Oxybutynin (0.351 g, $8.9 \times 10^{-4}$ mol) was dissolved in methanol (2 mL). (Compound 26) (0.053 g, 6.62 mg oxybutynin/mg of (compound 26)) was dissolved in methanol (2 mL) at room temperature under a nitrogen atmosphere. When completely dissolved, the oxybutynin solution was added dropwise, over 30 minutes, to the (compound 26) solution. The reaction mixture was sealed and left under a nitrogen atmosphere for 72 hours. The excess solvent was removed and the final product (compound 49) was isolated and dried. Film preparation: the isolated product (32 mg) was dissolved in a 10% DMF solution of Chronothane 80A (6 mL). This solution was pipetted into a 4×4 cm PTFE well and cast into a film. The film was processed in a 60° C. flow oven and a 50° C. vacuum oven. The film was monitored for surface defects and general quality. Release profile from urine: a strip of film (0.052 g) (1.3×0.75 cm) was cut and placed in a glass vial containing artificial urine solution (2 mL) at 37° C. The UV/Vis absorbance spectrum was measured at various timepoints (1, 2, 3, 4, 24, and 72 hours), and the release profile plotted in FIG. 15. A one inch segment of Carbothane catheter tubing containing barium sulphate was cut. (Compound 49) (101 mg) was dissolved in methanol (1 mL) and transferred into a glass tube. The catheter segment was dipcoated in the (compound 49) solution for 5 seconds, and dried in a 50° C. flow oven. Surface characteristics were examined by SEM (FIGS. 16 and 17).

EXAMPLE 35

α,ω-BAL-poly(LDI/PTMO)-p-PHEMA (Compound 23): Vitamin K1 (Compound 50)

Vitamin K1: This compound belongs to a group of lipophilic and hydrophobic vitamins that are needed for the post-translational modification of certain proteins, mostly required for blood coagulation.
Vitamin K1 (0.022 g, $4.9 \times 10^{-5}$ mol) was dissolved in DMF (1 mL). (Compound 23) (0.097 g, 0.23 mg vitamin K1/mg of (compound 23)) was dissolved in DMF (1 mL) at room temperature under a nitrogen atmosphere. Once completely dissolved, the vitamin K1 solution was added dropwise, over 60 minutes, to the (compound 23) solution. The reaction mixture was sealed and left under a nitrogen atmosphere for 24 hours. The excess solvent was removed and the final product (compound 50) was isolated and dried. (Compound 50) was also prepared using DMAc. Film preparation: the isolated product (29 mg) was dissolved in a 10% DMAc solution of Carbothane 85A (6 mL). This solution was pipetted into 4×4 cm PTFE wells and cast into films. Films were processed in a 60° C. flow oven and a 50° C. vacuum oven. Films were monitored for surface defects and general quality. Release profile: a strip of film (0.058 g) (1.3×0.75 cm) was cut and placed in a glass vial containing PBS with Tween (1.5 mL) at 37° C. The UV/Vis absorbance spectrum was measured at various time points (1, 2, 24, 48, and 72 hours) and the release profile plotted in FIG. 18. The release profile was also monitored for (compound 50) when isolated from DMAc. The differences between two matrices were noted based on data in Table 3.

TABLE 3

Concentration and mass of Vitamin K1 released from (compound 50)/Carbothane films in PBS with Tween, 37° C.

| | DMF preparation | | DMAc preparation | |
| --- | --- | --- | --- | --- |
| Time (hours) | Concentration (mg/mL) | Mass released (mg) | Concentration (mg/mL) | Mass released (mg) |
| 1 | 0.007 | 0.010 | 0.010 | 0.014 |
| 2 | 0.002 | 0.003 | 0.003 | 0.004 |
| 24 | 0.015 | 0.022 | 0.019 | 0.028 |
| 48 | 0.005 | 0.008 | 0.005 | 0.008 |
| 72 | 0.002 | 0.003 | 0.002 | 0.003 |

EXAMPLE 36

α,ω-BAL-poly(LDI/PTMO)-p-PVP (Compound 22): Vitamin K1 (Compound 51)

Vitamin K1 was (0.0234 g, 5.2×10$^{-5}$ mol) was dissolved in DMF (1 mL). (Compound 22) (0.0992 g, 0.236 mg vitamin K1/mg of (compound 22)) was dissolved in DMF (1 mL) at room temperature under a nitrogen atmosphere. Once completely dissolved, the vitamin K1 solution was added dropwise, over 60 minutes, to the (compound 22) solution. The reaction mixture was sealed and left under nitrogen for 24 hours. The excess solvent was removed and the final product (compound 51) was isolated and dried. Film preparation: the isolated product (30.6 mg) was dissolved in a 10% DMAc solution of Carbothane 85A (6 mL). This solution was pipetted into 4×4 cm PTFE wells and cast into a film. The film was processed in a 60° C. flow oven and a 50° C. vacuum oven. The film was monitored for surface defects and general quality. Release profile: a strip of film (0.051 g) (1.3×0.75 cm) was cut and placed in a glass vial containing PBS with Tween (1.5 mL) at 37° C. The W/V is absorbance spectrum was measured at various time points (1, 2, 3, and 4 hours) and the absorbances tabulated in Table 4.

TABLE 4

Absorbance of vitamin K1 released from a (compound 51)/Carbothane film in PBS with Tween, 37° C.

| Time (hours) | Absorbance |
| --- | --- |
| 1 | 1.4578 |
| 2 | 0.5834 |
| 3 | 0.3159 |
| 4 | 0.2444 |

EXAMPLE 37

α,ω-BAL-poly(LDI/PTMO)-p-PHEMA (Compound 23): Aspirin (Compound 52)

Aspirin: Aspirin or acetasal is often used as an analgestic, antipyretic and anti-inflammatory. It also has an antiplatelet "blood-thinning" effect and is used in long-term low-doses to prevent heart attacks. Low-dose long-term aspirin irreversibly blocks the formation of thromboxane $A_2$ in platelets, preventing platelet aggregation.

Aspirin (0.011 g, 6.1×10$^{-5}$ mol) was dissolved in DMF (1 mL). (Compound 23) (0.103 g, 0.10 mg aspirin/mg of (compound 23)) was dissolved in DMF (1 mL) at room temperature under a nitrogen atmosphere. Once completely dissolved, the aspirin solution was added dropwise, over 45 minutes, to the (compound 23) solution. The reaction mixture was sealed and left under a nitrogen atmosphere for 24 hours. The excess solvent was removed and the final product (compound 52) was isolated and dried. Film preparation: the isolated product (21 mg) was dissolved in a 10% DMAc solution of Carbothane 85A (6 mL). This solution was pipetted into a 4×4 cm PTFE well and cast into a film. The film was processed in a 60° C. flow oven and a 50° C. vacuum oven. The film was monitored for surface defects and general quality, and characterized by SEM (FIG. 19). The SEM image of the film showed a homogenous film with no phase separation.

Covalent Conjugation

EXAMPLE 38

Covalent Conjugation of (Compound 26) to Paclitaxel (Compound 53)

Figure 21:
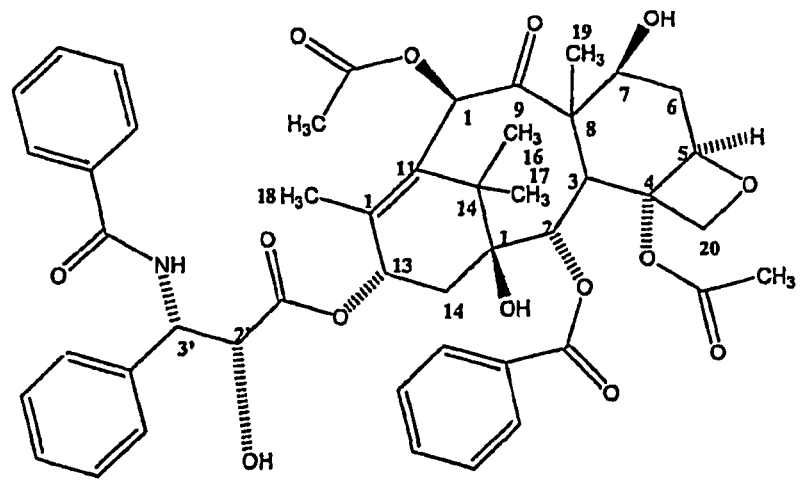
FIG. 21 is the chemical structure of paclitaxel. Numbers on the diagram are referenced in the proton NMR analysis of (compound 53). Once the drug is covalently conjugated to (compound 53) a clear shift in NMR spectra is noted.

(Compound 26) (0.1 gram, 0.845 mmol acid) was weighed into a 50 mL flask equipped with a septum port, placed under a nitrogen atmosphere, dissolved in anhydrous DMF (10 mL), and was chilled to 0° C. DIC (0.312 gram, 1.690 mmol) was added to the (compound 26) solution via syringe transfer, and the flask was kept well stirred for two hours with gradual warming to room temperature. DMAP (0.309 gram, 2.535 mmol) was added to the flask via powder transfer. Paclitaxel (PTX) (0.072 gram, 0.085 mmol) was dissolved in anhydrous DMF (1 mL) and transferred into the (compound 26) solution via syringe transfer. The solution was kept well stirred at room temperature for three days. Spectro/Por dialysis tubing (RC MWCO 1000) was presoaked in water for 1 hour, followed by rinsing with DMF. The reaction solution was loaded into the conditioned dialysis tubing and dialyzed against DMF. The solution of purified (compound 53) was recovered by rotary-evaporation. GPC analysis was performed using DMF/0.05 M LiBr mobile phase on a polystyrene column. Acidic polymers cannot be analyzed using DMP mobile phase, but GPC analysis can detect free paclitaxel, no unconjugated free paclitaxel was detected. (Compound 26) and (compound 53) were dissolved separately in DMSO (0.1 mg/mL) and analyzed by UV/VIS spectroscopy. (Compound 53) has a strong UV absorbance, whereas (compound 26) has a minimal W absorbance (FIG. 20). $^1$H NMR (300 MHz, DMSO) δ (ppm) 7.1-8.1 (aromatic H), 6.26 (C10), 5.74 (C3'), 5.44 (C2' conjugated), 5.37 (C2), 4.87 (C5), 4.52 (C7), 4.06 (C20), 3.54 (C3), 3.28 (PTMO H), 2.25 (C6), 2.13 (OAc, C4), 2.06 (OAc, C10), 1.78 (CH MMA), 1.70 (C18), 1.46 (PTMO H), 0.98 (CH$_2$ MMA). Refer to FIG. 21 for paclitaxel hydrogen assignments.

EXAMPLE 39

Covalent Conjugation of (Compound 23) to Methotrexate (Compound 54)

Figure 22:
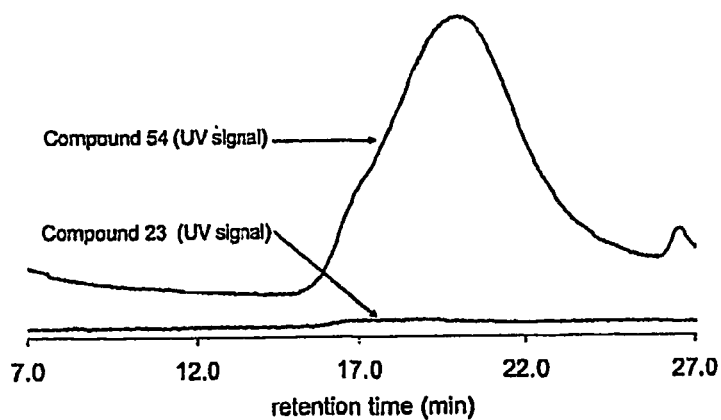
FIG. 22 is a plot of the GPC UV profiles of (compound 23) and (compound 54) showing compound 23 with no GPC UV characteristics and the methotrexate conjugated polymer with GPC UV characteristics.
Figure 23:
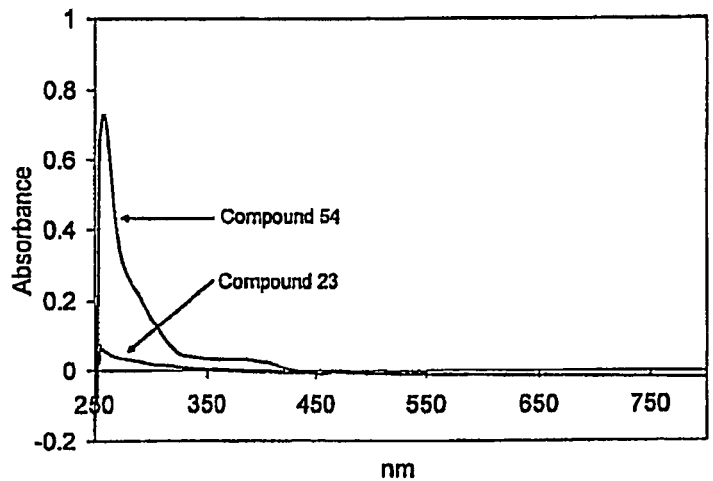
FIG. 23 is the UV/VIS profile of (compound 23) and (compound 54) showing compound 23 with no UV/VIS characteristics and the methotrexate conjugated polymer with UV/VIS characteristics.

Methotrexate (MIX) (14.7 mg, 0.032 mmol) was weighed into a 50 mL flask equipped with a septum port, placed under a nitrogen atmosphere, dissolved in anhydrous DMF (5 mL)

and chilled to 0° C. DIC (8.2 mg, 0.065 mmol) was added to the chilled MTX solution via syringe transfer and the solution was stirred with gradual warming over 2 hours. (Compound 23) (0.3 gram, 0.032 mmol OH) was weighed into a 25 mL flask equipped with a septum port, placed under a nitrogen atmosphere, and dissolved in anhydrous DMF (5 mL). DMAP (9.10 mg, 0.075 mmol) was added to the (compound 23) solution via powder transfer, and once dissolved, the (compound 23) solution was added to the activated MIX solution via syringe transfer. The reaction was kept well stirred under a nitrogen atmosphere for 60 hours. The DMF in the reaction solution was rotary-evaporated at 40° C., the residue was re-suspended in DMF (0.8 mL), and this solution was passed over the conditioned fluorous SPE columns to extract non-fluorinated compounds. The SPE eluent was rotary-evaporated at 40° C. to yield a yellow resinous material (compound 54). GPC analysis was performed using a DMF/0.05 M LiBr mobile phase on a polystyrene column. (Compound 23): Mn=$4\times10^4$, (compound 54): Mn=$4\times10^4$. The GPC 370 nm absorbance of (compound 23) and (compound 54) is displayed in FIG. 22, and the UV/VIS absorbance spectrum of (compound 23) and (compound 54) displayed in FIG. 23.

Drug Addition Pre-ATRP

EXAMPLE 40

ATRP Reaction in the Presence of Paclitaxel (Compound 55)

The ATRP addition of HEMA to (compound 11) to produce (compound 23) is described in example 13. The reaction described in this example introduces the atom transfer radical polymerization in the presence of a potent compound.

Figure 24:
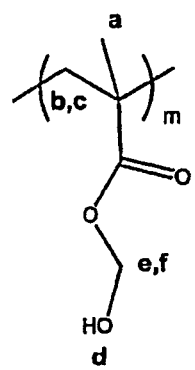
FIG. 24 shows the chemical repeat segment of HEMA in (compound 55), indicating NMR assignments by using protons labeled as e, f, b, and c.

(Compound 11) (0.100 gram, $1.7\times10^{-4}$ mol Br) was weighed into a 25 mL flask equipped with a septum port, degassed overnight at 30° C., and placed under a nitrogen atmosphere. Anhydrous DMF (4 mL) was added to the flask by syringe transfer. Paclitaxel (0.146 gram, $1.7\times10^{-4}$ mol) was dissolved in anhydrous DMF (1 mL), added to the (compound 11) solution, and the combined solution was deoxygenated using three freeze-pump-thaw cycles. The inhibitor in the HEMA monomer was removed by passing the reagent over a basic alumina column. In a 50 mL flask equipped with a septum port, Cu(I)Br (0.024 gram, $1.7\times10^{-4}$ mol), HMTETA (0.043 gram, $1.9\times10^{-4}$ mol), initiator free HEMA (0.489 gram, $3.8\times10^{-3}$ mol) and anhydrous DMF (1 mL) were combined, and the solution was deoxygenated using three freeze-pump-thaw cycles. The (compound 11)-PTx solution was transferred to the Cu(I)Br solution via syringe transfer, the flask was immersed in a 50° C. bath, and the combined solution was stirred well for 2 hours. The reaction was terminated by cooling the flask and opening it to air. The DMF was removed from the reaction solution by rotary-evaporation, and the reaction mixture was suspended in THF (20 mL) and passed through conditioned Phenomenex SCX SPE tubes to extract the catalyst. The product was recovered by evaporating the SPE eluent to dryness, followed by vacuum drying. The product (compound 55) (20 mg) was suspended in dioxane (1 mL), and the solution was centrifuged at 12 000 rpm for 5 minutes. The supernatant was analyzed by GPC (Dioxane mobile phase, PS columns, PS calibration). Free paclitaxel was detected at the 30 minute retention time. Similarly, 40 mg (compound 55) was suspended in THF (1.5 mL) and centrifuged at 12 000 rpm for 5 minutes. The supernatant was discarded, the pellet was dried under vacuum, and dissolved in DMSO (1 mL), and analyzed using proton NMR spectroscopy. Signals characteristic of free HEMA (4 peaks between 4.0 and 6.0 ppm) or paclitaxel were not noted in the extracted sample, but signals attributable to polymerized HEMA (FIG. 24) were clear. $^1$H NMR (300 MHz, DMSO) δ (ppm) 0.9-1.0 (a), 1.9-2.0 (b, c), 3.5 (f), 3.8 (e), 4.8 (d).

In a control reaction, the same reagents and conditions described above were applied, except that paclitaxel was excluded from the reaction mixture. In proton NMR analysis, the same spectra as reported for (compound 23), was recorded, indicating that the paclitaxel did not negatively influence the polymerization of the HEMA.

Synthesis of Grafted Polymer Using Dendritic Strategies

Figure 25:
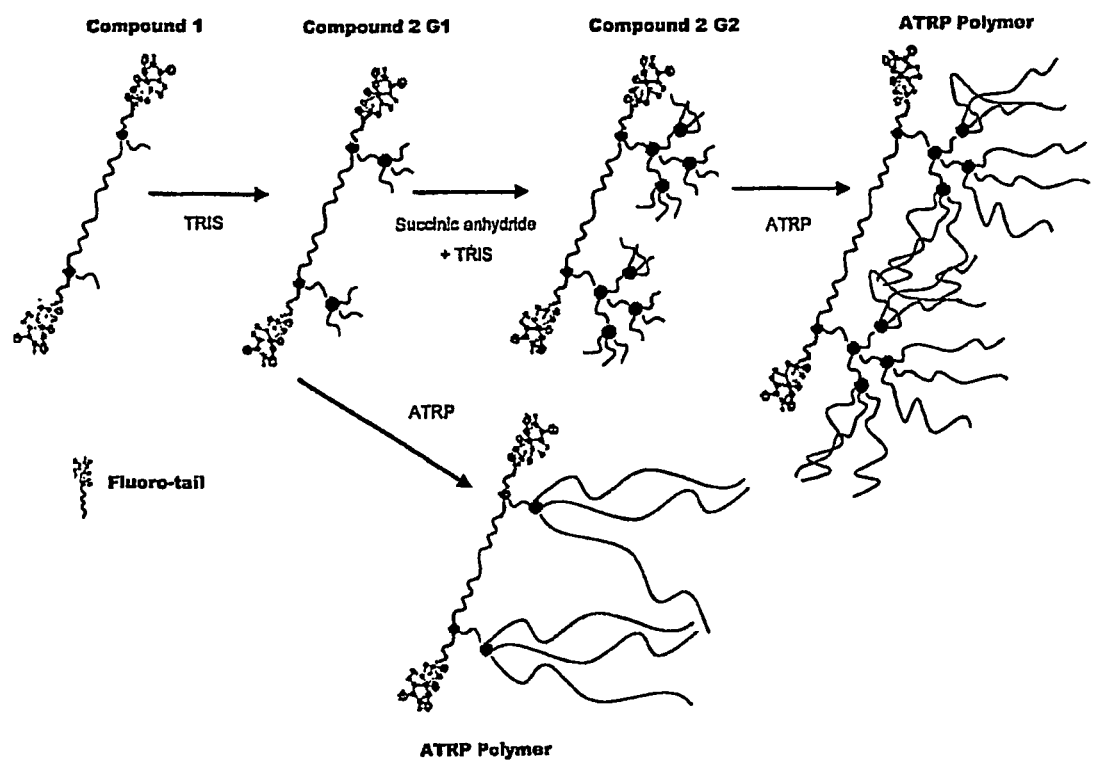
FIG. 25 is a schematic of dendron structures derived from (compound 2) showing dendron active functional group that can be used to initiate the ATRP synthesis.

The synthetic strategy to build cascade or regularly branched molecules introduces architectural features, with specific properties, into the polymer structure. In this section the design of oligomeric platforms with fluorinated backbones and dendron like wedges is described. The dendritic wedges increase the number of active sites for complexation of potent compounds, and/or introduces the polyvalency concept in the synthesis of the ATRP graft polymers (FIG. 25). It is important to note that dendritic ATRP introduces new architectural features and related properties to the final polymeric compounds.

EXAMPLE 41

Synthesis of Grafted Polymer with Dendritic Structures (Compound 56)

Method A: Synthesis of (Compound 56a)

(Compound 2b) (0.539 g) was weighed into a 50 mL flask and dissolved in anhydrous DMF (19 ml) under a nitrogen atmosphere. Succinic anhydride (0.094 g, 0.94 mmol), TEA (0.007 g, 0.07 mmol) and DMAP (0.008 g, 0.06 mmol) were added to the solution of (compound 2b) and the solution was stirred under a nitrogen atmosphere for 12 hours at 40° C. The solvent was removed by rotary-evaporation, the product (compound 56a) was dissolved in DMF (0.8 mL) and purified by fluorous SPE. $^1$H NMR (300 MHz, CDCl$_3$) δ (ppm) 3.64-3.69 (CH$_2$—CH$_2$ Tris), 2.64 (succinic CH$_2$—CH$_2$). HPLC analysis: retention time shifted from 34.6 minutes (compound 2b) to 32.7 minutes (compound 56a) under reversed phase HPLC, C18 column, methanol and pH 9 PBS mobile phase (gradient). Each of the carboxylic acid functional groups in (compound 56a) was further reacted with Tris molecules to increase the number of terminal groups. This stepwise reaction introduced two classes of functional groups suitable for increasing the number of terminal groups (compound 2b).

Method B: Synthesis of (compound 56b)

tBOC-Tris (0.509 g, 6.8 mmol) was weighed into a 100 mL flask and was dissolved in anhydrous DMF (26 mL) under a nitrogen atmosphere. Succinic anhydride (0.950 g, 9.5 mmol), TEA (0.069 g, 0.7 mmol) and DMAP (0.080 g, 0.65 mmol) were added to the solution of tBOC-Tris and the solution was stirred under a nitrogen atmosphere for 12 hours at 40° C. The reaction mixture was reduced to dryness by rotary-evaporation and the product (compound 57) was purified by extraction, with successive ethyl acetate/water extractions. (Compound 57) was reacted with Tris using the same reaction conditions as described for (compound 2a-2b) to yield (compound 58). (Compound 58) was dissolved in anhydrous DCM (10 mL), chilled to 0° C., and deprotected with CF$_3$COOH (3.3 mL) and purified by a silica gel column to yield (compound 59). $^1$H NMR (300 MHz, DMSO) δ (ppm) 2.64 (CH$_2$, succinic), 4.20 (Tris CH$_2$), 8.63 (NH$_2$), 12.2 (COOH). ESI MS (+ve mode) 422.1. (Compound 1-acid)

(0.245 g, 0.221 mmol acid) was weighed into a 50 mL flask and dissolved in anhydrous DMF (5 mL) under a nitrogen atmosphere. TEA (0.022 g, 0.22 mmol), DIC (0.028 g, 0.22 mmol) and (compound 59) (0.084 mg, 0.22 mmol) were added to the (compound 1-acid) solution and kept well stirred under a nitrogen atmosphere for seven days. The product (compound 56b) was purified by fluorous SPE. $^1$H NMR (300 MHz, DMSO) δ (ppm) 2.64 (CH$_2$, succinic), 4.20 (Tris CH$_2$), 12.2 (COOH).

ATRP Grafted and Base Polymer Admixtures

| Example No. | Description |
|---|---|
| 42 | Blending of (compounds 22, 27, and 59) into Tecoflex to reduce friction |
| 43 | Blending of (compounds 22 and 27) into Carbothane and extrusion of tubing. |
| 44 | Blending of (compounds 23 and 26) into Carbothane and surface analysis |

TABLE 5

Friction coefficients of Tecoflex films and blends with additives.

| | Components (wt. %) | | | | | | |
|---|---|---|---|---|---|---|---|
| Specimen | Tecoflex | -p-PVP (22) | L2PTNa (59) | -p-PNaMA (27) | $f_S$ | $f_K$ | σ |
| A | 100 | | | | 1.003 | 0.698 | 0.019 |
| B | 90 | 2.5 | 7.5 | | 0.894 | 0.189 | 0.043 |
| C | 90 | 5.0 | 5.0 | | 0.486 | 0.224 | 0.032 |
| D | 90 | 7.5 | 2.5 | | 0.631 | 0.178 | 0.038 |
| E | 95 | 2.6 | | 2.4 | 0.354 | 0.095 | 0.011 |

Compound numbers located in brackets ( ).

EXAMPLE 42: α,ω-BAL-poly(LDI/PTMO) pendent macrosoap (compound 59), pendent PVP (compound 22) and pendent MAA (compound 27), enhancing the surface lubricity of plastic film.

59

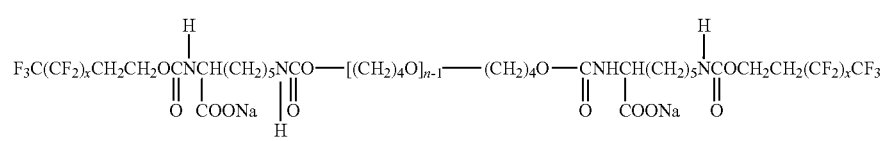

This example highlights the use of two polymers from the invention (compounds 22 and 27) incorporated into a biomedical polyurethane, Tecoflex (Noveon Corp., a common medical grade polymer used in catheter production): these two compounds were blended with Tecoflex in order to demonstrate a greater reduction in friction when compared to a mixture of the mono-ionic analog (compound 59) and (compound 22). This example effectively highlights the importance of having a multiplicity of ionic groups (compound 27) located in the same site as that of the mono-ionic groups of the sodium salt (compound 59), as well as demonstrating the use of the invention with commercial polymers.

Figure 26:
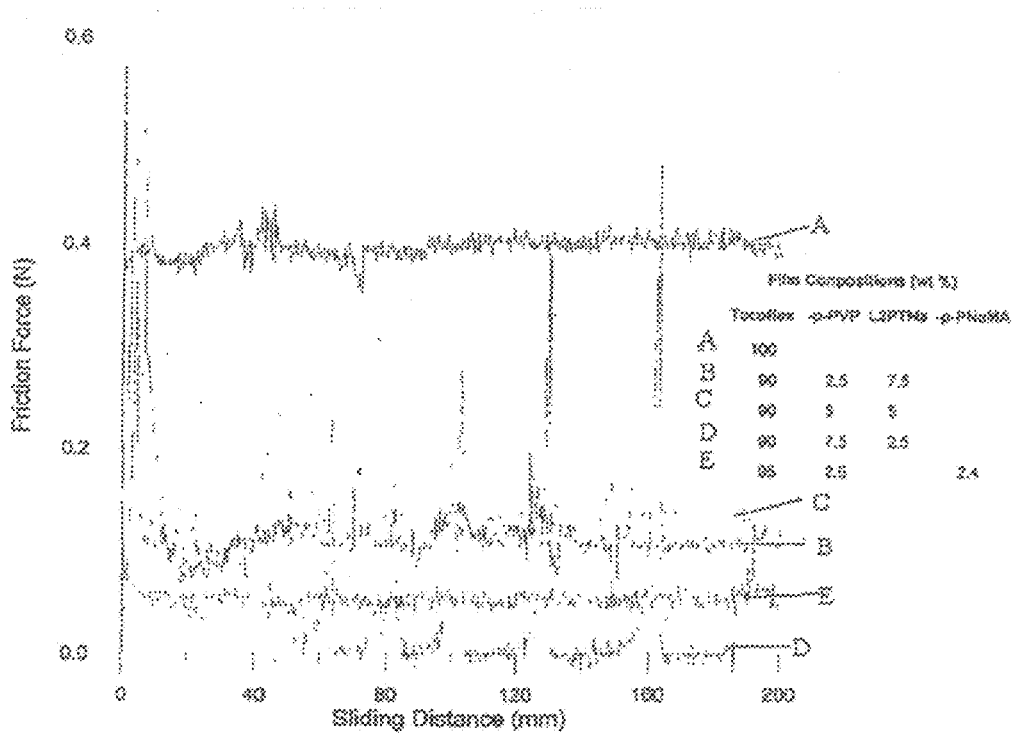
FIG. 26 is a plot of the friction coefficient analyses of Tecoflex films blended with (compounds 22, 59, and 27). A synergic combination of Tecoflex with compound 22 and 27 indicates a lower friction coefficient in comparison to when Tecoflex and compound 59 are used.

Tecoflex (EA80) (0.475 g) was dissolved in 7.5 ml of DMF. (Compound 22) (0.013 g) and (compound 27) (0.012 g) were dissolved in 2 ml of methanol The Tecoflex solution was added into a 5 5 cm Teflon dish and left drying in a fume hood for 1 hour. The (compound 22)/(compound 27) solution was added to the un-dried Tecoflex solution. The final mixture was left in the fume hood until all solvents were removed. The film was further dried under vacuum at 40° C. for 24 hours. The Tecoflex films blended with (compound 22) and (compound 59) (mono-ionic system) were made using the same procedure. (Compound 59) is an intermediate product of the (compound 1) precursor hydrolysis. FIG. 26 shows the friction tested according to ASTM D1894-01 and ASTM G115-98. Table 5 shows the static friction coefficient ($f_s$), kinetic friction coefficient ($f_K$), and standard deviation (σ) of the results. The data indicated the polyanionic material of the current invention to have a dramatic reduction in both kinetic and static friction coefficients in comparison to the commercial Tecoflex and the mono-ionic form of the additive. This example highlights the advantage of having the multiplicity of sodium carboxylate function on the additive.

EXAMPLE 43

α,ω-BAL-Poly(LDI/PTMO) Pendent Macrosoap (Compound 27) and Pendent PVP (Compound 22) Used for Compounding and Extrusion into Hollow Polyurethane (Carbothane) Tubing for Catheter Production An example of a formed biomedical article that integrates the incorporation of the polymers from the current invention into extruded medical grade components is described in this section. While many processing methods are exemplified in the medical device literature, the use of extrusion is an important one for polymers and is used to make many intermediate components of medical devices including but not limited the following shaped articles that are in whole or in part made of polyurethane components, namely, cardiac assist devices, tissue engineering polymeric scaffolds and related devices, cardiac replacement devices, cardiac septal patches, intra aortic balloons, percutaneous cardiac assist devices, extra-corporeal circuits, A-V fistual, dialysis components (tubing, filters, membranes, etc.), aphoresis units, membrane oxygenator, cardiac by-pass components (tubing, filters, etc.), pericardial sacs, contact lens, cochlear ear implants, sutures, sewing rings, cannulas, contraceptives, syringes, o-rings, bladders, penile implants, drug delivery systems, drainage tubes, pacemaker lead insulators, heart valves, blood bags, coatings for implantable wires, catheters, vascular stents, angioplasty balloons and devices, bandages, heart massage cups, tracheal tubes, mammary implant coatings, artificial ducts, craniofacial and maxillofacial reconstruction applications, ligaments, fallopian tubes, biosensors and bio-diagnostic substrates.

In this example we demonstrated that (compound 22) and (compound 27) (0.012 g) could be compounded with medical grade Carbothane 85A (containing 20% barium sulfate) and extruded to form hollow fiber tubing. Thermogravimetric analysis of the polymers indicated that the degradation temperature of (compound 22) was greater than 195° C. and that this material lost less than 10% of its weight between 195-295° C., suggesting that the material had good thermal stability. Thermogravimetric analysis of the poly-anionic polymer indicated that the degradation temperature of (compound 27) was greater then 225° C. and that this material lost less than 20% of its weight between 225-410° C., suggesting that the material had excellent thermal stability. It was noted that the latter material was significantly hygroscopic, showing 14% moisture uptake in ambient room conditions and that this moisture could be eliminated by drying the polymer and storing in anhydrous conditions.

Figure 27:
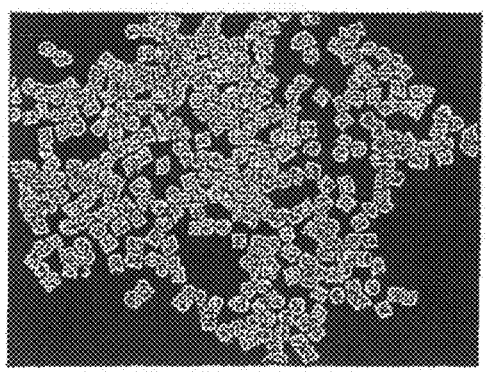
FIG. 27 is a picture of the compounded pellets of Carbothane with (compound 22) and (compound 27). This demonstrates suitable material properties for compounding.
Figure 28:
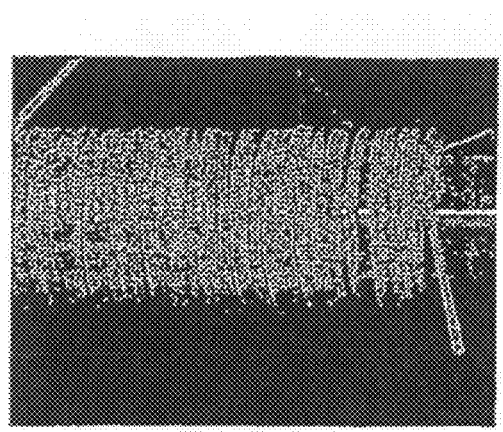
FIG. 28 is a picture of extruded hollow tubing made with pellets from Carbothane compounded with (compound 22) and (compound 27). This demonstrates suitable thermal stability for extrusion.

(Compound 27) (2.2 wt %) and (compound 22) (2.8 wt %) were compounded with (95 wt %) Carbothane (PC3585A-120) containing 20 wt % barium sulfate to form resin pellets. Compounding proceeded well, passing quality assurance inspection for color, size and appearance of the pellets (FIG. 27). Melt flow was 40.23 under test conditions of 230° C./2.16 kg. All data, as per received from vendor (Compounding Solutions). The resin pellets were then extruded to form the tubing seen in FIG. 28.

EXAMPLE 44

α,ω-BAL-poly(LDI/PTMO) with Pendent pHEMA (Compound 23) and pMAA (Compound 26) Blended into Carbothane (Compound 23) surface analysis: (compound 23) (9.8 mg) was dissolved in a 10% DMAc solution of Carbothane 85A (2 mL) and cast into a 2 cm×2 cm PTFE well. The film was processed in a 60° C. flow oven and a 50° C. vacuum oven. XPS analysis (90°): C, 59.8%; N, 2.6%; O, 15.8%; F, 21.5%. XPS analysis of control Carbothane film (90°): C, 87.0%; N, 4.3%; O, 7.5%; F, 0.0%. Excellent quality films were produced when (compound 23) was processed to obtain solution casted films.

(Compound 26) surface analysis: (compound 26) (10.0 mg) was dissolved in a 10% DMAc solution of Carbothane 85A (2 mL) and cast into a 2 cm×2 cm PTFE well. The film was processed in a 60° C. flow oven and a 50° C. vacuum oven. XPS analysis (90°): C, 67.5%; N, 2.4%; O, 14.8%; F, 14.1%. XPS analysis of control Carbothane film (90°): C, 87.0%; N, 4.3%; O, 7.5%; F, 0.0%.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:
1. A grafted polymer having the formula:

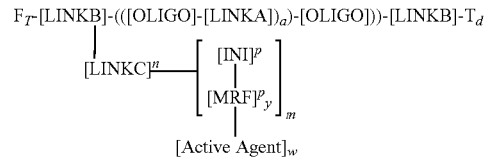

wherein
[OLIGO] is an oligomeric polymeric segment;
[LINKA] is a first coupling segment linking at least two [OLIGO] groups to form ((([OLIGO]-[LINKA]) a)-[OLIGO])) having a theoretical molecular weight of less than 15,000 Da;
T is a terminal group;
$F_T$ is a polyfluoroorgano group;
[MRF] is a polyolefin;
[INI] is a functional group having the capacity to initiate ATRP, atom transfer radical addition (ATRA), or atom transfer radical cyclization (ATRC);
[LINKB] is a second coupling segment linking ((([OLIGO]-[LINKA])a)-[OLIGO])) to $F_T$, to T, and/or to [LINKC];
[LINKC] is a third coupling segment linking [LINKB] to [INI] or, in the absence of [INI], [LINKC] is a dendron of n generations;
[Active Agent] is one or more active agents, and wherein the line between [Active Agent] and
[MRF] in the formula represents an interaction that is a covalent bond or a non-covalent interaction;
a and d are integers greater than 0;
n is an integer from 1 to 150;
p is an integer from 1 to 20;
m is an integer from 1 to 20;
y is an integer from 1 to 20;
w is an integer from 1 to 20; and
with the provisos that
m≦n; and
w≦y.

2. The grafted polymer of claim 1, wherein said ((([OLIGO]-[LINKA]) a)-[OLIGO])) comprises a polycondensate selected from polyurethane, polyurea, polyamides, polyaklylene oxide, polycarbonate, polyester, polylactone, polysilicone, polyethersulfone, polypeptide, polysaccharide, polysiloxane, polydimethylsiloxane, polypropylene oxide, polyethylene oxide, polytetramethyleneoxide, and combinations thereof.

3. The grafted polymer of claim 1, wherein said [MRF] is selected from polyacrylic acid, polymethacrylic acid, poly (hydroxyethylmethacrylate), poly(hydroxyethylacrylate), poly(methylalkylsulfoxide methacrylate), poly(methylalkylsulfoxide acrylate), polyacrylamide, poly(methacrylamide), poly(dimethylacrylamide), poly(N-isopropyl-acrylamide), poly(vinyl alcohol), poly(vinyl pyrrolidone), poly(N-vinyl caprolactam), and copolymers thereof.

4. The grafted polymer of claim 1, wherein said FT comprises from about 0.01 to 50 weight % of said grafted polymer.

5. The grafted polymer of claim 1, wherein said active agent is selected from proteins, peptides, carbohydrates, antibiotics, antiproliferative agents, rapamycin macrolides, analgesics, anesthetics, antiangiogenic agents, antithrombotic agents, vasoactive agents, anticoagulants, immunomodulators, cytotoxic agents, antiviral agents, antibodies, neurotransmitters, psychoactive drugs, oligonucleotides, vitamins, lipids, and prodrugs thereof.

6. The grafted polymer of claim 1, wherein said (([OLIGO]-[LINKA]) a)-[OLIGO])) has an absolute molecular weight of less than 10 kDa.

7. A shaped article formed from a grafted polymer of claim 1.

8. The grafted polymer of claim 1, wherein said non-covalent interaction is selected from the group consisting of: hydrogen-bonding, ionic interactions, inclusion complexes, clathration, van der Waals interactions, and coordination to a metal center, and combinations thereof.

* * * * *